US012686699B2

(12) United States Patent
Kinney et al.

(10) Patent No.: US 12,686,699 B2
(45) Date of Patent: Jul. 21, 2026

(54) CRYSTALLINE FORMS OF SQUALAMINE

(71) Applicant: Enterin, Inc., Philadelphia, PA (US)

(72) Inventors: William A. Kinney, Newtown, PA (US); Anil Kumar, Skillman, NJ (US); Qi Gao, South Plainfield, NJ (US); Giovanna Brancatelli, Amsterdam (NL)

(73) Assignee: Enterin, Inc., Philadelphia, PA (US)

( * ) Notice: Subject to any disclaimer, the term of this patent is extended or adjusted under 35 U.S.C. 154(b) by 777 days.

(21) Appl. No.: 17/912,025

(22) PCT Filed: Sep. 25, 2020

(86) PCT No.: PCT/US2020/052608

§ 371 (c)(1),
(2) Date: Sep. 15, 2022

(87) PCT Pub. No.: WO2021/188148

PCT Pub. Date: Sep. 23, 2021

(65) Prior Publication Data

US 2023/0159582 A1 May 25, 2023

Related U.S. Application Data

(60) Provisional application No. 62/991,855, filed on Mar. 19, 2020.

(51) Int. Cl.
*C07J 41/00* (2006.01)
*A61K 31/575* (2006.01)
(Continued)

(52) U.S. Cl.
CPC ......... *C07J 41/0005* (2013.01); *A61K 31/575* (2013.01); *C07B 2200/13* (2013.01)

(58) Field of Classification Search
CPC .... C07J 41/0005; A61K 31/575; A61K 45/06; C07B 2200/13; A61P 25/28; A61P 9/10; C07F 9/02
See application file for complete search history.

(56) References Cited

U.S. PATENT DOCUMENTS 5,721,226 A 2/1998 Frye et al.
7,981,876 B2 * 7/2011 Chellquist ............ C07J 41/0005 552/521

(Continued)

FOREIGN PATENT DOCUMENTS

JP 2003-519698 A 6/2003
WO WO-2011/066260 A1 6/2011
WO WO-2019/089365 A1 5/2019

OTHER PUBLICATIONS

Bhattacharya et al., "Thermoanalytical and Crystallographic Methods." Polymorphism in Pharmaceutical Solids, 2nd edition, Editor Brittain, Publ. Informa Healthcare USA, pp. 318-346 (Year: 2009).*

(Continued)

*Primary Examiner* — Jeffrey S Lundgren
*Assistant Examiner* — Alexander K. Showalter
(74) *Attorney, Agent, or Firm* — Foley & Lardner LLP

(57) ABSTRACT

This disclosure provides crystalline polymorphs of squalamine phosphate, methods of making the same, and methods of treatment using the same.

31 Claims, 14 Drawing Sheets

(51) Int. Cl.

| | |
|---|---|
| ***A61K 45/06*** | (2006.01) |
| ***A61P 9/10*** | (2006.01) |
| ***A61P 25/28*** | (2006.01) |
| ***C07F 9/02*** | (2006.01) |

(56) References Cited

U.S. PATENT DOCUMENTS

| | | | | |
|---|---|---|---|---|
| 10,040,817 | B2 * | 8/2018 | Zasloff | A61P 25/24 |
| 11,066,438 | B2 * | 7/2021 | Barbut | A61P 25/28 |
| 2007/0010504 | A1 | 1/2007 | Chellquist et al. | |
| 2010/0209497 | A1 * | 8/2010 | Thornthwaite | A61K 45/06 424/94.1 |
| 2011/0123624 | A1 | 5/2011 | Zasloff | |
| 2019/0127416 | A1 | 5/2019 | Barbut et al. | |

OTHER PUBLICATIONS

Chadha et al., An Insight into Thermodynamic Relationship Between Polymorphic Forms of Efavirenz, J. Pharm. & Pharmaceut. Sci., pp. 234-251 (Year: 2012).*

Chitkul, et al., "A new bio-compatible pH cleavable linker for solid-phase synthesis of a squalamine analogue," *Tetrahedron Letters*, vol. 42, pp. 6211-6214 (2001).

International Search Report issued in International Patent Application No. PCT/US2020/052608, dated Jan. 12, 2021.

Braak et al., "Idiopathic Parkinson's disease: possible routes by which vulnerable neuronal types may be subject to neuroinvasion by an unknown pathogen," *J. Neural. Transm.* (Vienna), 110:517-36 (2003).

Braak et al., "Staging of brain pathology related to sporadic Parkinson's disease," *Neurobiol. Aging*, 24:197-211 (2003).

McKhann, et al., "The diagnosis of dementia due to Alzheimer's disease: recommendations from the National Institute on Aging-Alzheimer's Association workgroups on diagnostic guidelines for Alzheimer's disease," Alzheimer's Dement., May 2011;7(3):263-269.

Zasloff, et al., "A spermine-coupled cholesterol metabolite from the shark with potent appetite suppressant and antidiabetic properties," *Int J Obes Relat Metab Disord*., May 2001; 25(5):689-697.

Zhao et al., "A comparative study of the amount of α-synuclein in ischemic stroke and Parkinson's disease," Neurol. *Sci*. 37(5):749-754 (2016).

Byrn et al., "Pharmaceutical Solids: A Strategic Approach to Regulatory Considerations", Pharmaceutical Research, vol. 12, No. 7, pp. 945-954 (1995).

Kawaguchi, et al. "Drug and crystal polymorphism", Journal of Human Environmental Engineering vol. 4, pp. 310-317 (2002).

Ooshima; "Crystallization of Polymorphs and Pseudo-polymorphs and Its Control"; Pharm Stage, 6(10):48-53 (Jan. 2007).

Pharmaceutical Affairs Bureau Notification No. 568, 45 pages (2001).

Takata, API Form Screening and Selection at Drug Development Stage, Pharm Stage, vol. 6, No. 10, pp. 20-25 (Jan. 2007).

Yamano, "Approach to Crystal Polymorph in Process Research of New Drug", Journal of Synthetic Organic Chemistry, vol. 65, No. 9, pp. 907-913 (2007).

JP Notice of Reasons for Refusal on JP Appl. Ser. No. 2022-555862 Dated Nov. 12, 2024.

* cited by examiner

CRYSTALLINE FORMS OF SQUALAMINE

CROSS REFERENCE TO RELATED APPLICATION

This application is the U.S. National Stage of International Patent Application No. PCT/US2020/052608, filed Sep. 25, 2020, which claims the benefit of priority from U.S. Provisional Patent Application No. 62/991,855, filed Mar. 19, 2020. The contents of these applications are incorporated herein by reference in their entirety.

FIELD

The present application relates generally to a novel aminosterol compounds and polymorphs thereof for the treatment of disease.

BACKGROUND

Aminosterols are amino derivatives of a sterol. Squalamine is the most abundant member of a larger aminosterol family comprising at least 12 related compounds. Exemplary aminosterols include squalamine and aminosterol 1436 (also known as trodusquemine and MSI-1436). Aminosterol 1436 exhibits pharmacology in vertebrates causing weight loss and adipose tissue mobilization. Squalamine has antiviral, antibiotic, antifungal, and anticancer activity, and inhibits aggregation of the α-synuclein (αS) protein characteristic in Parkinson's disease (PD).

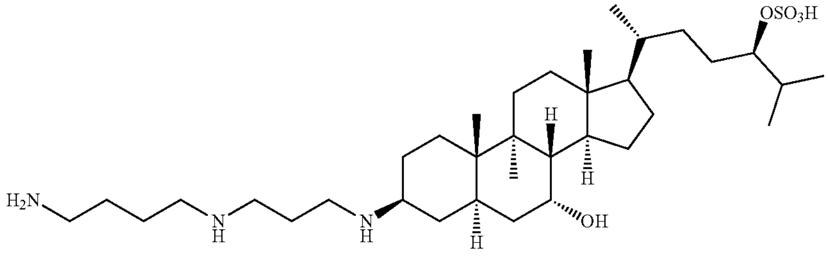

squalamine

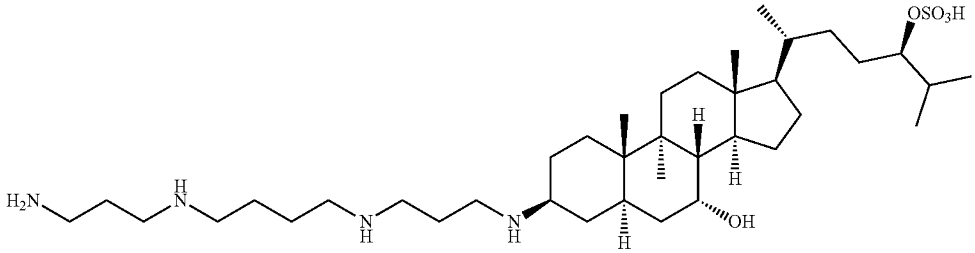

aminosterol 1436

There is a need in the art for new aminosterol compounds and the present disclosure satisfies this need.

SUMMARY

In one aspect, a crystalline hydrate of Compound I is provided:

Compound I

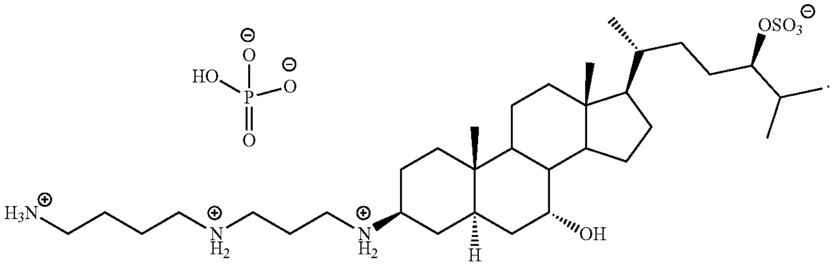

In some embodiments, the crystalline hydrate comprises Form A1 and/or Form C, wherein: (a) Form A1 is characterized by at least one X-ray powder diffraction (XRPD) peak (Cu $K_{\alpha 1}$ radiation) selected from 3.96°, 8.59°, 10.84°, 11.49°, 13.27°, 13.89°, 15.27°, 15.52°, 15.78°, 15.98°, 17.72°, 17.91°, 18.76°, 19.18°, 19.37°, 20.44°, 20.58°, 20.80°, 21.24°, 21.76°, 22.18°, 23.09°, 23.35°, 23.83°, 24.02°, 24.53°, 25.10°, 25.48°, 25.81°, 26.14°, and 26.67° (each ±0.01°2θ); and (b) Form C is characterized by at least one X-ray powder diffraction (XRPD) peak (Cu $K_{\alpha 1}$ radiation) selected from 3.82°, 8.22°, 10.55°, 11.19°, 11.45°, 11.99°, 13.35°, 13.77°, 14.05°, 14.59°, 15.14°, 15.63°, 16.39°, 16.89°, 17.28°, 17.94°, 18.57°, 18.92°, 19.39°, 19.75°, 20.71°, 21.16°, 21.45°, 21.99°, 22.49°, 22.98°, 23.26°, 23.79°, 24.11°, 24.59°, and 24.91° (each ±0.01°2θ).

In some embodiments, (a) Form A1 is characterized by the XRPD pattern substantially as shown in FIG. 1; and (b) and Form C is characterized by the XRPD pattern substantially as shown in FIG. 5.

In some embodiments, the crystalline hydrate comprises Form A1. In some embodiments, the crystalline hydrate is a tetrahydrate. In some embodiments, the crystalline hydrate has a differential scanning calorimetry thermogram comprising an endotherm at about 40° C. to about 120° C.

In some embodiments, the crystalline hydrate has a differential scanning calorimetry thermogram substantially as shown in FIG. 4. In some embodiments, the crystalline hydrate comprises Form C. In some embodiments, the crystalline hydrate is a hexahydrate.

In some embodiments, the crystalline hydrate has a differential scanning calorimetry thermogram comprising an endotherm at about 40° C. to about 120° C. In some embodiments, the crystalline hydrate has a differential scanning calorimetry thermogram substantially as shown in FIG. 9.

In another aspect, a composition comprising the crystalline hydrate is provided. In some embodiments, the composition comprises one or more of the following: (a) an aqueous carrier; (b) a buffer; (c) a sugar; and/or (d) a polyol compound.

In some embodiments, the composition further comprises at least one additional active agent. In some embodiments, the composition is formulated: (a) for administration selected from the group consisting of oral, pulmonary, rectal, colonic, parenteral, intracisternal, intravaginal, intraperitoneal, intravenous, subcutaneous, intramuscular, nebulization, inhalation, ocular, otic, local, buccal, nasal, and topical administration; (b) into a dosage form selected from the group consisting of liquid dispersions, gels, aerosols, ointments, creams, lyophilized formulations, tablets, and capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

In some embodiments, the composition is formulated for oral administration. In some embodiments, the composition is formulated as an oral tablet or capsule. In some embodiments, the composition is formulated for intranasal administration.

In another aspect a method of preparing the crystalline hydrate or the composition is provided, the method comprising contacting Compound II:

Compound II

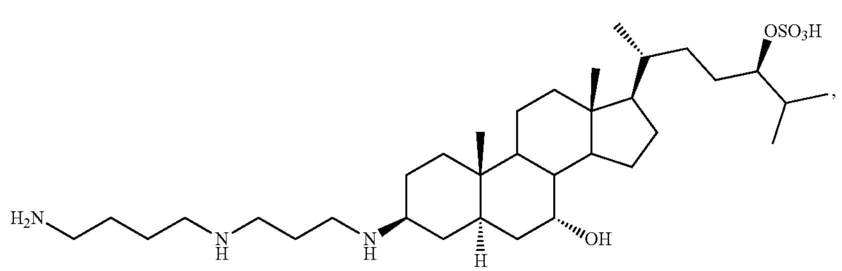

or a pharmaceutically acceptable salt thereof, with phosphoric acid to form the crystalline hydrate.

In some embodiments, a lactate salt of Compound II is contacted with phosphoric acid. In some embodiments, a lactate salt of Compound II having the formula:

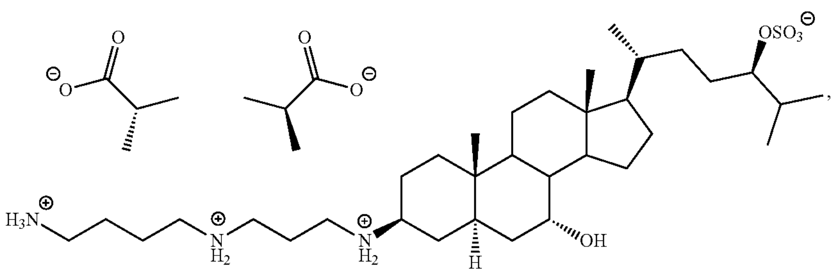

is contacted with phosphoric acid.

In some embodiments, Compound II, or a pharmaceutically acceptable salt thereof, is in water and ethanol prior to contacting with phosphoric acid. In some embodiments, the ratio of water to ethanol is about 1 to about 1. In some embodiments, the water and ethanol further comprise sodium hydroxide (NaOH).

In another aspect, a method of treating a subject in need having a condition susceptible to treatment with an aminosterol is provided, the method comprising administering a therapeutically effective amount of the composition to the subject. In some embodiments, the condition is correlated with abnormal alpha-synuclein pathology and/or dopaminergic dysfunction.

In another aspect, a method of treating, preventing, and/or slowing the onset or progression of a condition or disorder, or a related symptom, correlated with abnormal alpha-synuclein pathology and/or dopaminergic dysfunction, in a subject in need is provided, the method comprising administering a therapeutically effective amount of a composition disclosed herein.

In some embodiments: (a) the symptom is selected from the group consisting of constipation, hallucinations, cognitive impairment, and inflammation; (b) the symptom is correlated with a synucleopathy, a neurodegenerative disease, a neurological disease or disorder, a psychological and/or behavior disorder, or a cerebral or general ischemic disorder or condition; or (c) the condition or disorder is a synucleopathy, neurodegenerative disease, or neurological disease or disorder; (d) the condition or disorder is a psychological and/or behavior disorder; or (e) the condition or disorder is a cerebral or general ischemic disorder or condition.

In some embodiments: (a) the synucleopathy, neurodegenerative disease, or neurological disease or disorder is selected from the group consisting of Parkinson's disease, Alzheimer's disease, schizophrenia, multiple system atrophy, Lewy body dementia, dementia with Lewy bodies, Huntington's Disease, Multiple Sclerosis, Amyotorphic Lateral Sclerosis, Friedreich's ataxia, vascular dementia, spinal muscular atrophy, supranuclear palsy, progressive nuclear palsy, frontotemporal dementia, progressive nuclear palsy, Guadeloupian Parkinsonism, spinocerebellar ataxia, parkinsonism, traumatic brain injury, degenerative processes associated with aging, and dementia of aging; (b) the psychological or behavior disorder is selected from the group consisting of depression, autism, autism spectrum disorder, Down syndrome, Gaucher's disease, Krabbe's disease, lysosomal conditions affecting glycosphingolipid metabolism, ADHD, agitation, anxiety, delirium, irritability, illusion and delusions, amnesia, apathy, bipolar disorder, disinhibition, aberrant motor and obsessive-compulsive behaviors, addiction, cerebral palsy, epilepsy, major depressive disorder, and sleep disorders such as REM sleep behavior disorder (RBD), sleep fragmentation, REM behavior disorder, circadian rhythm dysfunction, sleep apnea, and cognitive impairment; or (c) the cerebral or general ischemic disorder or condition is selected from the group consisting of microangiopathy, intrapartum, cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects, high blood pressure, low blood pressure, and pulmonary edema.

In another aspect, a method of treating, preventing, and/or slowing the onset or progression a cerebral or general ischemic disorder and/or a related symptom, correlated with abnormal alpha-synuclein pathology and/or dopaminergic dysfunction, in a subject in need, is provided, the method comprising administering a therapeutically effective amount of a composition disclosed herein, to the subject.

In some embodiments, the cerebral or general ischemic disorder and/or a related symptom is selected from the group consisting of microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, low blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects (CCDs) and/or a related symptom, and pulmonary edema.

In another aspect, a method of inhibiting protein tyrosine phosphatase 1B (PTP1B) in a subject is provided, the method comprising administering to the subject a therapeutically effective amount of a composition disclosed herein.

In some embodiments, the method of administration comprises oral, nasal, sublingual, buccal, rectal, vaginal, intravenous, intra-arterial, intradermal, intraperitoneal, intrathecal, intramuscular, epidural, intracerebral, intracerebroventricular, transdermal, or any combination thereof.

In some embodiments, the method of administration is nasal administration, oral administration, or a combination thereof. In some embodiments, the therapeutically effective amount of the composition comprises: (a) about 0.1 to about 20 mg/kg body weight of the subject; (b) about 0.1 to about 15 mg/kg body weight of the subject; (c) about 0.1 to about 10 mg/kg body weight of the subject; (d) about 0.1 to about 5 mg/kg body weight of the subject; or (e) about 0.1 to about 2.5 mg/kg body weight of the subject.

In some embodiments, the therapeutically effective amount of the composition comprises: (a) about 0.001 to about 500 mg/day; (b) about 0.001 to about 250 mg/day; (c) about 0.001 to about 125 mg/day; (d) about 0.001 to about 50 mg/day; (e) about 0.001 to about 25 mg/day; (f) about 0.001 to about 10 mg/day; (g) about 0.001 to about 6 mg/day; (h) about 0.001 to about 4 mg/day; or (i) about 0.001 to about 2 mg/day.

In some embodiments, the method of administration comprises oral administration and wherein the therapeutically effective amount of the composition comprises: (a) about 1 to about 300 mg/day; or (b) about 25 to about 500 mg/day. In some embodiments, the composition is administered in combination with at least one additional active agent to achieve either an additive or synergistic effect.

In some embodiments, the additional active agent is administered via a method selected from the group consisting of: (a) concomitantly; (b) as an admixture; (c) separately and simultaneously or concurrently; and (d) separately and sequentially.

In some embodiments, the additional active agent is a second aminosterol having a different structure from Compound I. In some embodiments, administration of the composition comprises administration on an empty stomach, optionally within two hours of the subject waking.

In some embodiments, no food is consumed by the subject after about 60 to about 90 minutes from administration of the composition. In some embodiments, the composition is of pharmaceutically acceptable grade. In some embodiments, the subject is a mammal. In some embodiments, the subject is a human.

In some embodiments the method further comprises: (a) determining a dosage of the composition for the subject, wherein the composition dosage is determined based on the effectiveness of the composition dosage in improving or resolving a symptom being evaluated, (b) followed by administering the composition dosage to the subject for a period of time, wherein the method comprises: (i) identifying a symptom to be evaluated, wherein the symptom is susceptible to treatment with an aminosterol; (ii) identifying a starting dosage of composition for the subject; (iii) administering an escalating composition dosage to the subject over a period of time until an effective dosage for the symptom being evaluated is identified, wherein the effective dosage is composition dosage where improvement or resolution of the symptom is observed, and fixing the composition dosage at that level for that particular symptom in that particular subject. In some embodiments, improvement or resolution of the symptom is measured using a clinically recognized scale or tool.

In some embodiments, the composition is administered orally and: (a) the starting composition dosage ranges from about 10 mg up to about 150 mg/day; (b) the dosage of the composition for the subject following escalation is fixed at a range of from about 25 mg up to about 500 mg/day; and/or (c) the dosage of composition is escalated in about 25 mg increments.

In some embodiments, the composition is administered intranasally and: (a) the starting composition dosage ranges from about 0.001 mg to about 3 mg/day; (b) the dosage of the composition for the subject following escalation is fixed at a range of from about 0.001 mg up to about 6 mg/day; (c) the dosage of the composition for the subject following escalation is a dosage which is subtherapeutic when given orally or by injection; and/or (d) the dosage of the composition is escalated in increments of about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

In some embodiments, the dosage of the composition is escalated every about 3 to about 5 days. In some embodiments, the starting composition dosage is higher if the symptom being evaluated is severe. In some embodiments, the symptom is correlated with abnormal alpha-synuclein pathology and/or dopaminergic dysfunction.

In some embodiments, the symptom to be evaluated is selected from the group consisting of: (a) at least one non-motor aspect of experiences of daily living as defined by Part I of the Unified Parkinson's Disease Rating Scale selected from the group consisting of cognitive impairment, hallucinations and psychosis, depressed mood, anxious mood, apathy, features of dopamine dysregulation syndrome, sleep problems, daytime sleepiness, pain, urinary problems, constipation problems, lightheadedness on standing, and fatigue; (b) at least one motor aspect of experiences of daily living as defined by Part II of the Unified Parkinson's Disease Rating Scale selected from the group consisting of speech, saliva and drooling, chewing and swallowing, eating tasks, dressing, hygiene, handwriting, turning in bed, tremors, getting out of a bed, a car, or a deep chair, walking and balance, and freezing; (c) at least one motor symptom identified in Part III of the Unified Parkinson's Disease Rating Scale selected from the group consisting of speech, facial expression, rigidity, finger tapping, hand movements, pronation-supination movements of hands, toe tapping, leg agility, arising from chair, gait, freezing of gait, postural stability, posture, body bradykinesia, postural tremor of the hands, kinetic tremor of the hands, rest tremor amplitude, and constancy of rest tremor; (d) at least one motor complication identified in Part IV of the Unified Parkinson's Disease Rating Scale selected from the group consisting of time spent with dyskinesias, functional impact of dyskinesias, time spent in the off state, functional impact of fluctuations, complexity of motor fluctuations, and painful off-state dystonia; (e) constipation; (f) depression; (g) cognitive impairment; (h) sleep problems or sleep disturbances; (i) circadian rhythm dysfunction; (j) hallucinations; (k) fatigue; (l) REM disturbed sleep; (m) REM behavior disorder; (n) erectile dysfunction; (o) apnea; (p) postural hypotension; (q) correction of blood pressure or orthostatic hypotension; (r) nocturnal hypertension; (s) regulation of temperature; (t) improvement in breathing or apnea; (u) correction of cardiac conduction defect; (v) amelioration of pain; (w) restoration of bladder sensation and urination; (x) urinary incontinence; and/or (y) control of nocturia.

In some embodiments, the symptom to be evaluated is constipation, and wherein: (a) the fixed escalated composition dosage for constipation is defined as the composition dosage that results in a complete spontaneous bowel movement (CSBM) within 24 hours of dosing on at least 2 of 3 days at a given dosage; (b) if average complete spontaneous bowel movement (CSBM) or average spontaneous bowel movement (SBM) is greater than or equal to 1 per week, then the starting composition dosage prior to escalation is 75 mg/day; and/or (c) if average CSBM or SBM is less than 1 per week, then the starting composition dosage prior to escalation is 150 mg/day.

In one aspect, a method of increasing gene transcription in the gut of a subject is provided, the method comprising administering to the subject a therapeutically effective amount of the crystalline hydrate or the composition.

In some embodiments, the increase in gene transcription is for one or more genes selected from the group consisting of caspase 14, collagen type XVII alpha 1, corneodesmosin, cornifelin, cystatin E/M, dermokine, desmocollin 1, desmoglein 1 beta, filaggrin, gap junction protein beta 4, gap junction protein beta 6, H19 imprinted maternally expressed transcript, hornerin, kallikrein related-peptidase 7 chymotryptic stratum, keratin 1, keratin 10, keratinocyte differentiation associated protein, keratinocyte expressed proline-rich, late cornified envelope 1A1, late cornified envelope 1A2, late cornified envelope 1, late cornified envelope 1C, late cornified envelope 1E, late cornified envelope 1F, late cornified envelope 1G, late cornified envelope 1H, late cornified envelope 1I, late cornified envelope 1J, late cornified envelope 1L, late cornified envelope 1M, late cornified envelope 3C, late cornified envelope 3E, late cornified envelope 3F, lectin galactose binding soluble 7, loricrin, sciellin, myoglobin, myosin binding protein C slow-type, myosin heavy polypeptide 1 skeletal muscle, myosin heavy polypeptide 8 skeletal muscle, myosin light chain phosphorylatable fast ske, myosin light polypeptide 3, myozenin 1, myozenin 2, and titin-cap.

In some embodiments, the increase in gene transcription is selected from about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, about 250% to about 300%, about 300% to about 350%, about 350% to about 400%, about 400% to about 450%, about 500% to about 600%, about 600% to about 700%, about 700% to about 800%, about 800% to about 900%, about 900% to about 1000%, or about 1000% to about 1500%.

DETAILED DESCRIPTION

I. Overview

Figure 1:
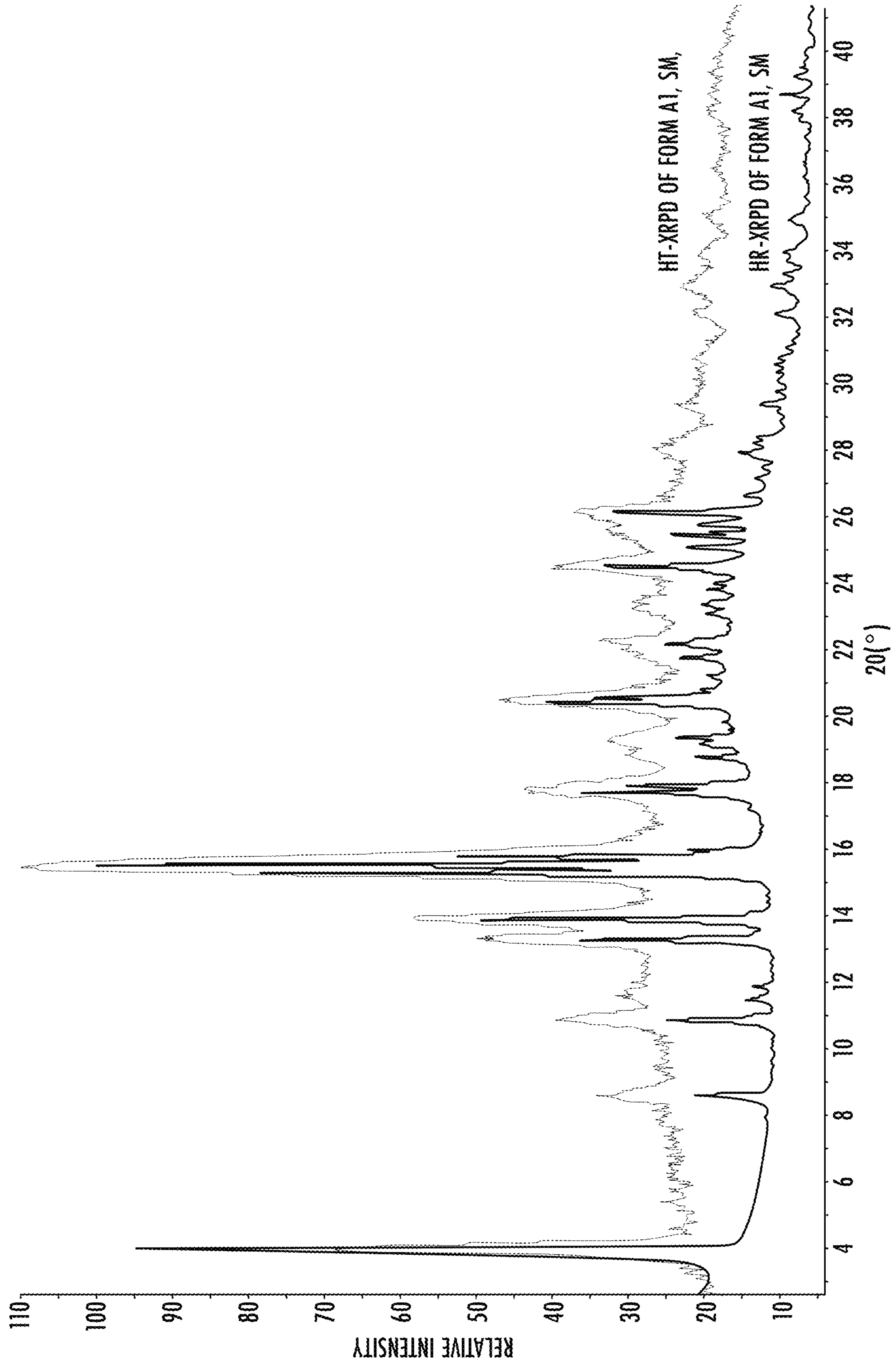
FIG. 1: Overlay of High Throughput (HT, top line) and High Resolution (HR, bottom line) X-ray Powder Diffraction (XRPD) patterns of the Form A1.

The present disclosure is directed to novel crystalline polymorphs of squalamine. Methods for the production of such polymorphs have been developed and are also disclosed herein.

Squalamine is a compound with pharmacological properties implicating its use in the treatment of disease. Squalamine targets neurotoxic aggregates of α-synuclein (αS) in the gastrointestinal tract to restore function of the enteric nerve cells and treat disease. Pharmaceutical use of squalamine salts requires the identification and characterization of specific polymorphic crystal forms of squalamine. Ideal polymorphs should be tested to have stability against moisture and heat and solubility in biorelevant media.

Polymorphism is important in the development of pharmaceutical ingredients. Polymorphic purity of drug samples can be checked using techniques such as powder X-ray diffraction. Many drugs receive regulatory approval for only a single crystal form or polymorph. Polymorphism in drugs can also have direct medical implications. Medicine is often administered orally as a crystalline solid and dissolution rates depend on the exact crystal form of a polymorph. Different polymorphs of the same compound can vary in properties important with regard to storage, such as stability and hygroscopicity. Thus, identification of the most commercially practical polymorph of squalamine phosphate is important and this disclosure addresses this need.

A. Summary of Experimental Results

The polymorphic behavior of squalamine phosphate (ENT-01) and the physico-chemical properties of two hydrated phases were investigated. A squalamine tetrahydrate, designated Form A1, was identified. The squalamine polymorphism assessment and hydrate screen allowed identification of several squalamine crystalline phases. Among these phases, four squalamine hydrates (Forms B1, B2, C, D) and three mixed squalamine hydrates/solvates (Forms A2, E, F) were identified. All phases converted to squalamine Form A1 upon exposure to accelerated aging conditions (ACC) (2 days at 40° C./75% RH).

At least three hydrated phases of squalamine phosphate (ENT-01) were isolated: Forms B1, A1 and C, a squalamine sesquihydrate, a squalamine tetrahydrate and a squalamine hexahydrate, respectively. The hydrate screen performed on squalamine phosphate (ENT-01) revealed that in ethanol/water systems the switch of crystalline phases occurs around $a_w$~0.7. For $a_w$<0.7 the squalamine tetrahydrate Form A1 is the crystalline phase favored at 5 and 25° C., whereas the squalamine hexahydrate Form C crystallizes at $a_w \geq 0.7$. At 50° C., Form C appeared at $a_w \geq 0.8$.

The investigation under variable RH levels by both DVS and XRPD revealed that both squalamine Forms A1 and C started to release water at RH levels below 20%, converting to an unknown lower degree hydrate (or anhydrous) phase. This novel squalamine phase converted to Form A1 when exposed to RH levels >20%.

The physical stability test performed on squalamine Forms A1, B1 and C revealed that squalamine Form A1 was stable under all investigated conditions (80° C., 60° C./29% RH and 40/75% RH). In contrast, squalamine Forms B1 and C were more sensitive to the tested storage conditions. The low-degree squalamine hydrate, Form B1, absorbed water already at 29% RH converting to squalamine Form A1, and the hexahydrate Form C released water at low RH levels or at high temperature, converting to Form A1. The drying conditions affected the squalamine solid phase composition. Squalamine Form B1 can be easily produced by drying squalamine Form A1 under vacuum at 50° C. for 24 hours.

The squalamine crystalline phase A1 is preferred over squalamine Form C mainly because it has a larger range of stability in terms of temperature and RH levels (between 35 to 65% RH, squalamine Form A1 can absorb 0.7% of water). Squalamine Form C showed conversion to squalamine Form A1 by exposure to low RH levels and to high temperatures.

From a solubility perspective, squalamine Forms A1 and C showed similar behavior in biorelevant media. Both squalamine Forms A1 and C were insoluble in Fasted State Simulated Intestinal Fluid (FaSSIF) (pH 6.8), whereas a solubility close to 1 mg/mL was determined in Fed State Simulated Intestinal Fluid (FeSSIF) for both phases. In Fasted State Simulated Gastric Fluid (FaSSGF), differences were observed between squalamine Forms A1 and C. Squalamine Form C appears to be more soluble than squalamine Form A1, with a solubility of ~17 mg/mL vs ~9 mg/mL, respectively.

The dissolution rate determination in FaSSGF supports the selection of squalamine Form A1 as a favored candidate for pharmaceutical manufacture and use, given that squalamine Form A1 showed a slightly higher dissolution rate than Form C.

B. Background Regarding Squalamine and Disease

Not to be bound by theory, it is believed that aminosterols, including the squalamine polymorphs described herein, work by targeting neurotoxic aggregates of αS in the gastrointestinal tract (GIT) to restore function of the enteric nerve cells, thereby treating and/or preventing brain-gut disorders such as those described herein. This effect of aminosterols is highly unexpected given that aminosterols have a very low bioavailability; e.g., squalamine appears to work locally rather than via absorption into the blood stream. Following squalamine administration, the now-functional enteric nerve cells prevent retrograde trafficking of proteins, such as αS, to the brain. In addition to restoring GI function, this effect is believed to slow and possibly reverse disease progression of brain-gut disorders such as Parkinson's Disease (PD), as well as other related brain-gut diseases and conditions as described herein.

C. Alpha-Synuclein (αS) and Disease

PD correlates with the formation of toxic αS aggregates within the enteric nervous system (ENS) (Braak et al. 2003 (a); Braak et al. 2003 (b)). αS aggregates to form insoluble fibrils in pathological conditions characterized by Lewy bodies, such as PD, dementia with Lewy bodies (DLB), and multiple system atrophy (MSA). These disorders are known as synucleinopathies. Thus, one indicator of αS pathology is the formation of αS aggregates.

At the molecular level, protein misfolding, accumulation, aggregation and subsequently the formation of amyloid deposits are common features in many neurological disorders including Alzheimer's disease (AD) and PD. The existence of a common mechanism suggests that neurodegenerative disorders likely share a common trigger and that the nature of the pathology is determined by the type of the aggregated protein and the localization of the cell affected.

Examples of conditions associated with abnormal αS pathology, and/or dopaminergic dysfunction, also referred to as "brain-gut" disorders, include, but are not limited to, synucleinopathies, neurodiseases, psychological and/or behavior disorders, cerebral and general ischemic disorders, and/or disorders or conditions. Examples of synucleinopathies, neurodegenerative disease and/or neurological diseases include, for example, AD, PD, Lewy body dementia (LBD) or dementia with Lewy bodies (DLB), multiple system atrophy (MSA), Huntington's Disease, Multiple Sclerosis (MS), Amyotorphic Lateral Sclerosis (ALS), schizophrenia, Friedreich's ataxia, vascular dementia, spinal muscular atrophy (SMA), progressive nuclear palsy, supranuclear palsy, frontotemporal dementia (FTD), progressive supranuclear palsy, Guadeloupian Parkinsonism, parkinsonism, spinocerebellar ataxia, stroke, traumatic brain injury, degenerative processes associated with aging, and dementia of aging. Examples of psychological or behavior disorders include for example depression, autism, Down syndrome, Gaucher's disease (GD), Krabbe's disease (KD), lysosomal conditions affecting glycosphingolipid metabolism, ADHD, agitation, anxiety, delirium, irritability, illusion and delusions, amnesia, apathy, bipolar disorder, disinhibition, aberrant motor and obsessive-compulsive behaviors, addiction, cerebral palsy, epilepsy, major depressive disorder, and sleep disorders such as REM sleep behavior disorder (RBD), sleep fragmentation, REM behavior disorder, circadian rhythm dysfunction, sleep apnea, and cognitive impairment. Examples of general ischemic or cerebral ischemic disorders include for example microangiopathy, intrapartum, cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects, high blood pressure, low blood pressure and pulmonary edema.

Constipation serves as an early indicator of many neurodiseases such as PD to the extent that it is suspected to correlate with the formation of toxic αS aggregates within the enteric nervous system (ENS). As a result of the normal trafficking of αS aggregates from the ENS to the central nervous system (CNS) via afferent nerves such as the vagus, neurotoxic aggregates accumulate progressively within the brainstem and more rostral structures. Inhibiting αS aggregation in the ENS may therefore reduce the continuing neuro disease process in both the ENS and CNS. This relationship between the ENS and CNS is sometimes described herein as "brain-gut" in relation to a class of disorders or the axis of aminosterol activity.

Not to be bound by theory, it is believed that aminosterols improve bowel function by acting locally on the GIT (as supported by the low oral bioavailability, e.g., less than about 0.3%). It is theorized that nerve impulses initiated from the ENS following administration of an aminosterol augments afferent neural signaling to the CNS. This may stimulate the clearance of αS aggregates within the afferent neurons themselves as well as the secondary and tertiary neurons projecting rostrally within the CNS, since it is known that neural stimulation is accompanied by increased neuronal autophagic activity. It is believed that after cessation of aminosterol administration, the neurons of the CNS gradually re-accumulate an αS burden either locally or via trafficking from αS re-aggregation within the gut.

II. Polymorphs of Squalamine Phosphate (ENT-01) and Methods of Preparation

In one aspect, a crystalline polymorph of Compound I is provided:

Compound I

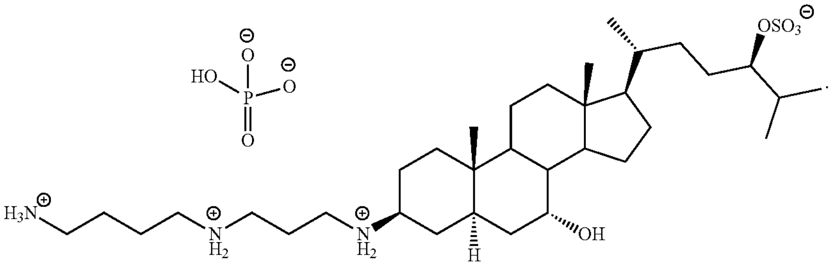

In some embodiments, the crystalline polymorph is of Form A1, A2, B1, B2, C, D, E, or F and characterized by at least one X-ray powder diffraction (XRPD) peak (Cu $K_{\alpha1}$ radiation) selected from Table 2 (squalamine Form A1), Table 3 (squalamine Form B1), Table 4 (squalamine Form C), Table 5 (squalamine Form A2), Table 6 (squalamine Form B2), Table 7 (squalamine Form D), Table 8 (squalamine Form E), or Table 9 (squalamine Form F), where each value ±0.01°2θ), respectively.

In some embodiments, the crystalline polymorph is a crystalline hydrate. The crystalline hydrate may comprise Form A1 and/or Form C, wherein (a) Form A1 is characterized by at least one X-ray powder diffraction (XRPD) peak (Cu $K_{\alpha1}$ radiation) selected from 3.96°, 8.59°, 10.84°, 11.49°, 13.27°, 13.89°, 15.27°, 15.52°, 15.78°, 15.98°, 17.72°, 17.91°, 18.76°, 19.18°, 19.37°, 20.44°, 20.58°, 20.80°, 21.24°, 21.76°, 22.18°, 23.09°, 23.35°, 23.83°, 24.02°, 24.53°, 25.10°, 25.48°, 25.81°, 26.14°, and 26.67° (each ±0.01°2θ); and (b) Form C is characterized by at least one X-ray powder diffraction (XRPD) peak (Cu $K_{\alpha1}$ radiation) selected from 3.82°, 8.22°, 10.55°, 11.19°, 11.45°, 11.99°, 13.35°, 13.77°, 14.05°, 14.59°, 15.14°, 15.63°, 16.39°, 16.89°, 17.28°, 17.94°, 18.57°, 18.92°, 19.39°, 19.75°, 20.71°, 21.16°, 21.45°, 21.99°, 22.49°, 22.98°, 23.26°, 23.79°, 24.11°, 24.59°, and 24.91° (each ±0.01°2θ).

Differential scanning colorimetry (DSC) may be used to ascertain the water content of the hydrate. The method is based on the hypothesis that the enthalpy of binding of n moles of water molecules in the hydrate (enthalpy of dehydration, $\Delta H_d$) is the same as that of n moles of water molecules in liquid water ($n\Delta H_v$), where $\Delta H_v$ is the enthalpy of vaporization of water. From the literature value of $\Delta H_v$ and the $\Delta H_d$ value for each dehydration endotherm the number of moles of water associated with each endotherm may be calculated.

In some embodiments, the crystalline hydrate is a mono, di, tri, tetra, penta, hexa, septa, octa, nona, or decahydrate. In some embodiments, the crystalline hydrate is a tetrahydrate. In some embodiments, the crystalline hydrate is a hexahydrate. The crystalline hydrate may have a differential scanning calorimetry thermogram comprising an endotherm at about 40° C. to about 120° C.

In one aspect, a method of preparing the crystalline hydrate disclosed herein is provided, comprising contacting Compound II:

Compound II

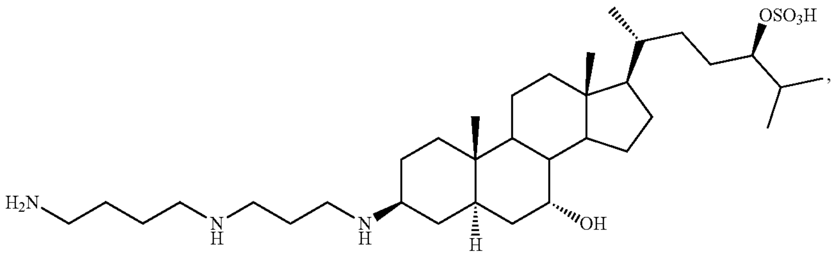

or a pharmaceutically acceptable salt thereof, with phosphoric acid to form the crystalline hydrate. In some embodiments, a lactate salt of Compound II is contacted with phosphoric acid. In some embodiments, the lactate salt of Compound II having the formula:

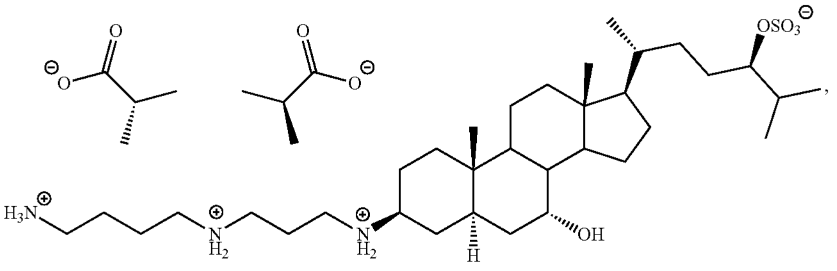

is contacted with phosphoric acid.

III. Compositions

In another aspect, provided herein are compositions comprising a squalamine crystalline polymorph or hydrate disclosed herein and one or more pharmaceutically acceptable carriers and/or excipients.

A. Pharmaceutical Carriers

While it is possible for squalamine or a polymorph thereof to be administered alone, it is preferable to administer it as a pharmaceutical formulation, together with one or more pharmaceutically acceptable carriers. The carrier(s) must be "acceptable" in the sense of being compatible with the squalamine polymorph thereof and not deleterious to the recipients thereof.

Generally, the formulations are prepared by contacting the squalamine crystalline polymorph described herein uniformly and intimately with liquid carriers or finely divided solid carriers or both. Then, if necessary, the product is shaped into the desired formulation. Non-aqueous vehicles such as fixed oils and ethyl oleate are also useful herein, as well as liposomes.

The carrier suitably comprises minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as gelatin, serum albumin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In instances where aerosol administration is appropriate, the squalamine polymorph can be formulated as an aerosol using standard procedures. The term "aerosol" includes any gas-borne suspended phase of a compound described herein which is capable of being inhaled into the bronchioles or nasal passages, and includes dry powder and aqueous aerosol, and pulmonary and nasal aerosols. "Aerosol" also includes a dry powder composition of a composition of the present technology suspended in air or other carrier gas, which may be delivered by insufflation from an inhaler device, for example.

B. Dosage Forms

The squalamine polymorph compositions may be presented in unit dosage forms and may be prepared by any of the methods well known in the art of pharmacy. Exemplary dosage forms include, but are not limited to, oral, intranasal, and injectable (IP, IV, or IM). Preferably, the squalamine polymorph formulation is administered orally, intranasally, or a combination thereof. In yet another embodiment, administration comprises non-oral administration.

Formulations or compositions of the present technology may be packaged together with, or included in a kit with, instructions or a package insert. "Pharmaceutically acceptable carrier" refers to a non-toxic solid, semisolid or liquid filler, diluent, encapsulating material or formulation auxiliary of any type.

Pharmaceutical compositions according to the present technology may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener such as sucrose, xylitol, sodium saccharin, cyclamate, aspartame, and acesulfame. Examples of flavoring agents are Magnasweet® (trademark of MAFCO), bubble gum flavor, fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride. Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose. Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

C. Dosages & Dosing Period

Dosage of squalamine polymorph compositions described herein can range from about 1 to about 500 mg/day, or any amount in between these two values. In some embodiments, a subject is administered a therapeutically effective dose of the squalamine polymorph composition described herein. The therapeutically effective amount of the squalamine polymorph composition can be, for example, about 0.1 to about 20 mg/kg, about 0.1 to about 15 mg/kg, about 0.1 to about 10 mg/kg, about 0.1 to about 5 mg/kg, or about 0.1 to about 2.5 mg/kg body weight of the subject. In another aspect, the therapeutically effect amount of the squalamine polymorph composition can be, for example, about 0.001 to about 500 mg/day, about 0.001 to about 250 mg/day, about 0.001 to about 125 mg/day, about 0.001 to about 50 mg/day, about 0.001 to about 25 mg/day, or about 0.001 to about 10 mg/day.

Oral dosage of a squalamine polymorph composition described herein can range from about 1 to about 500 mg/day, or any amount in between these two values. In one embodiment, the method of administration comprises oral administration and the therapeutically effective amount of the squalamine polymorph composition comprises (i) about 1 to about 300 mg/day; (ii) about 25 to about 300 mg/day; (iii) about 50 to about 300 mg/day; or (iv) about 75 to about 300 mg/day. Other exemplary dosages of orally crystalline include, but are not limited to, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, or about 500 mg/day.

Intranasal dosages of squalamine polymorph compositions are much lower than oral dosages of the composition. Examples of such intranasal composition low dosages include, but are not limited to, about 0.001 to about 6 mg/day, or any amount in between these two values. In some embodiments, the method of administration comprises nasal administration and the therapeutically effective amount of the squalamine polymorph composition comprises (i) about 0.001 to about 6 mg/day; (ii) about 0.001 to about 4 mg/day; (iii) about 0.001 to about 2 mg/day. For example, the low dosage of an intranasally administered composition can be about 0.001, about 0.005, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, or about 6 mg/day.

For intranasal (IN) administration, it is contemplated that the squalamine polymorph composition dosage may be selected such that the same dosage would not provide any pharmacological effect if administered by any other route—e.g., a "subtherapeutic" dosage, and, in addition, does not result in negative effects. For example squalamine has the pharmacological effects of a reduction in food intake and weight loss. Therefore, in the intranasal (IN) methods of the disclosure, if the squalamine polymorph composition is delivered intranasally (IN), then if the same IN dosage is administered via another route, such as oral, IP, or IV, then the dosage will not result in a noticeable reduction in food intake or noticeable weight loss. Similarly, squalamine may produce the pharmacological effects of nausea, vomiting and/or reduced blood pressure. Thus, in the IN methods of the disclosure, if the squalamine polymorph composition has this effect when given IN, then if the same IN dosage is administered via another route, such as oral, IP, or IV, then the composition dosage will not result in noticeable nausea, vomiting, and/or a reduction in blood pressure. In some embodiments, intranasal administration comprises delivery of squalamine to the brain.

Squalamine polymorph doses can be de-escalated (reduced) if any given dose induces a persistent undesirable side effect, such as diarrhea, vomiting, or nausea. In another embodiment, a squalamine polymorph dose can be varied plus or minus a defined amount to enable a modest reduction in a dose to eliminate adverse events, or a modest increase in a dose if clinical results suggest this is desirable—e.g., no or minimal adverse events and potential increased efficacy with a modest increase in dose. For example, in one embodiment a squalamine polymorph dose can be increased or decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

The pharmaceutical composition comprising a squalamine polymorph can be administered for any suitable period of time, including as a maintenance dose for a prolonged period of time. Dosing can be done on an as-needed basis using any pharmaceutically acceptable dosing regimen. Dosing can be no more than once per day, once every other day, once every three days, once every four days, once every five days, once every six days, once a week, or divided over multiple time periods during a given day (e.g., twice daily). In an exemplary embodiment, dosing is once a day.

In other embodiments, the squalamine polymorph composition can be administered (1) as a single dose, or as multiple doses over a period of time; (2) at a maintenance dose for an indefinite period of time; (3) once, twice or multiple times; (4) daily, every other day, every 3 days, weekly, or monthly; (5) for a period of time such as about 1, about 2, about 3, or about 4 weeks, about 1, about 2, about 3, about 4, about 5, about 6, about 7, about 8, about 9, about 10, about 11, or about 12 months, about 1 year, about 1.5 years, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, or about 25 years, or (6) any combination of these parameters, such as daily administration for 6 months, weekly administration for 1 or more years, etc.

Yet another exemplary squalamine polymorph dosing regimen includes periodic dosing, where an effective dose can be delivered once every about 1, about 2, about 3, about 4, about 5, about 6 days, or once weekly.

In an exemplary embodiment, the squalamine polymorph dose is taken in the morning, i.e., on an empty stomach preferably within about two hours of waking up and may be followed by a period without food, such as for example about 60 to about 90 minutes. In other embodiments, the squalamine polymorph dose is taken within about 15 min, about 30 min, about 45 min, about 1 hour, about 1.25 hours, about 1.5 hours, about 1.75 hours, about 2 hours, about 2.25 hours, about 2.5 hours, about 2.75 hours, about 3 hours, about 3.25 hours, about 3.5 hours, about 3.75 hours, or about 4 hours within waking up. In yet further embodiments, the squalamine polymorph dose is followed by about period without food, wherein the period is at least about 30 minutes, about 45 minutes, about 60 minutes, about 1.25 hours, about 1.5 hours, about 1.75 hours, or about 2 hours.

Not to be bound by theory, it is believed that since squalamine has an impact on circadian rhythms, likely due to ENS signaling, taking the squalamine polymorph dose in the morning enables the synchronization of all the autonomic physiological functions occurring during the day. In other embodiments of the disclosure, the squalamine polymorph dosage is taken within about 15 minutes, about 30 minutes, about 45 minutes, about 1 hour, about 1.25 hours, about 1.5 hours, about 1.75 hours, about 2 hours, about 2.25 hours, about 2.5 hours, about 2.75 hours, about 3 hours, about 3.25 hours, about 3.5 hours, about 3.75 hours, or about 4 hours of waking up. In addition, in other embodiments of the disclosure, following the squalamine polymorph dosage the subject has a period of about 15 minutes, about 30 minutes, about 45 minutes, about 1 hours, about 1.25 hours, about 1.5 hours, about 1.75 hours, about 2 hours, about 2.25 hours, about 2.5 hours, about 2.75 hours, or about 3 hours without food.

D. "Fixed Dose"

In one aspect, the present application relates to the discovery of a method to determine a "fixed dose" of a squalamine polymorph composition described herein that is not age, size, or weight dependent but rather is individually calibrated. The "fixed dose" obtained through this method yields highly effective results in treating the symptom(s) based on which the "fixed dose" was determined, related symptoms along the "brain-gut" axis, and the underlying disorder. Further, contemplated herein are methods of leveraging this same "fixed dose" method for methods of prevention of the underlying disorder. The present disclosure is not limited to methods whereby a fixed squalamine polymorph composition dosage is determined for a specific patient.

A squalamine polymorph "fixed dose," also referred to as a "fixed escalated dose," which will be therapeutically effective is determined for each patient by establishing a starting dose of a squalamine polymorph composition and a threshold for improvement of a particular symptom which is used as a tool or marker for evaluating the effectiveness of the squalamine polymorph composition dosage. Following determining a squalamine polymorph dosage for a particular patient, the composition dose is then progressively escalated by a consistent amount over consistent time intervals until the desired improvement is achieved; this composition dosage is the "fixed escalated composition dosage" for that particular patient for that particular symptom. In exemplary embodiments, an orally administered squalamine polymorph composition dose is escalated every about 3 to about 5 days by about 25 mg until the desired improvement is reached. Symptoms evaluated, along with tools for measuring symptom improvement, may be specifically described below, including but not limited to constipation, hallucinations, sleep disturbances (e.g., REM disturbed sleep or circadian rhythm dysfunction), cognitive impairment, depression, or α-synuclein aggregation.

This therapeutically effective squalamine polymorph "fixed dose" is then maintained throughout treatment and/or prevention. Thus, even if the patient goes "off drug" and ceases taking the composition, the same squalamine polymorph "fixed dose" is taken with no ramp up period following re-initiation of treatment.

Not to be bound by theory, it is believed that the squalamine polymorph dose is dependent on the severity of nerve damage relating to the symptom establishing the "fixed dose" threshold—e.g., for constipation, the dose may be related to the extent of nervous system damage in the patient's gut.

Dose escalation: When determining a squalamine polymorph "fixed dosage" for a particular patient, a patient is started at a lower dose and then the dose is escalated until a positive result is observed for the symptom being evaluated. An exemplary symptom to be evaluated can be constipation, but any symptom associated with the disease or disorder to be treated can be used as a marker for evaluating dosage. Doses can also be de-escalated (reduced) if any given dose induces a persistent undesirable side effect, such as diarrhea, vomiting, or nausea.

The starting squalamine polymorph composition dose is dependent on the severity of the symptom—e.g., for a patient experiencing severe constipation, defined as less than one spontaneous bowel movement (SBM) a week, the starting oral squalamine polymorph composition dose can be about 150 mg/day or greater. In contrast, for a patient having moderate constipation, e.g., defined as having more than one SBM a week, the starting oral squalamine polymorph composition dose can be about 75 mg/day.

In other embodiments, a patient experiencing moderate symptoms (for the symptom being used to calculate a fixed escalated composition dose) can be started at an oral squalamine polymorph composition dosage of from about 10 mg/day to about 75 mg/day, or any amount in between these values. For example, the starting oral squalamine polymorph composition dosage for a moderate symptom can be about 10, about 15, about 20, about 25, about 30, about 35, about 40, about 45, about 60, about 65, about 70, or about 75 mg/day.

In yet further embodiments, when the patient is experiencing severe symptoms (for the symptom being used to calculate the fixed escalated composition dose), the patient can be started at an oral squalamine polymorph composition dosage ranging from about 75 to about 175 mg/day, or any amount in between these two values. For example, the starting oral squalamine polymorph composition dosage for a severe symptom can be about 75, about 80, about 85, about 90, about 95, about 100, about 105, about 110, about 115, about 120, about 125, about 130, about 135, about 140, about 145, about 150 about 155, about 160, about 165, about 170, or about 175 mg/day.

In some embodiments, the starting oral squalamine polymorph composition dose may be about 125 mg or about 175 mg/day, again dependent on the severity of the symptom, such as constipation.

Starting IN squalamine polymorph composition dosages prior to dose escalation can be, for example, about 0.001 mg to about 3 mg/day, or any amount in between these two values. For example, the starting squalamine polymorph composition dosage for IN administration, prior to dose escalation, can be, for example, about 0.001, about 0.005, about 0.01, about 0.02, about 0.03, about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 1.0, about 1.1, about 1.25, about 1.3, about 1.4, about 1.5, about 1.6, about 1.7, about 1.75, about 1.8, about 1.9, about 2.0, about 2.1, about 2.25, about 2.3, about 2.4, about 2.5, about 2.6, about 2.7, about 2.75, about 2.8, about 2.9, or about 3 mg/day.

In exemplary embodiments, the squalamine polymorph composition dose is given periodically as needed. For example, the squalamine polymorph composition dose can be given once per day. The composition dose can also be given every other day, 2, 3, 4, or 5 times per week, once a week, or twice a week. In another embodiment, the squalamine polymorph composition dose can be given every other week, or it can be given for a few weeks, followed by skipping a few weeks (as the effects persist following treatment), followed by restarting treatment.

When calculating a fixed escalated squalamine polymorph composition dose, the dose can be escalated following any suitable time period. In one embodiment, the squalamine polymorph composition dose is escalated every about 3 to about 7 days by about a defined amount until a desired improvement is reached. For example, when the symptom being treated/measured is constipation, threshold improvement can be an increase of one SBM per week or at least a total of three bowel movements per week. In other embodiments, the squalamine polymorph composition dose can be escalated every about 1, about 2, about 3, about 4, about 5, about 6, about 7, about 8, about 9, about 10, about 11, about 12, about 13, or about 14 days. In other embodiments, the squalamine polymorph composition dose can be escalated by about once a week, about twice a week, about every other week, or about once a month.

During dose escalation, the squalamine polymorph composition dosage can be increased by a defined amount. For example, when the composition is administered orally, the squalamine polymorph dose can be escalated in increments of about 5, about 10, about 15, about 20, about 25, about 30, about 35, about 40, about 45, or by about 50 mg. When the squalamine polymorph composition is administered intranasally, then the dosage can be increased in increments of, for example, about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

Other symptoms that can be used as an endpoint to determine squalamine polymorph composition dosage for a patient's fixed escalated composition dosage are any symptom known to be associated with the disease, disorder, or condition intended to be treated. For example, neurodisease symptoms described herein and include, but are not limited to, (a) at least one non-motor aspect of experiences of daily living as defined by Part I of the Unified Parkinson's Disease Rating Scale (UPDRS), such as, for example, cognitive impairment, hallucinations and psychosis, depressed mood, anxious mood, apathy, features of dopamine dysregulation syndrome, sleep problems, daytime sleepiness, pain, urinary problems, constipation problems, lightheadedness on standing, and fatigue; (b) at least one motor aspect of experiences of daily living as defined by Part II of the UPDRS, such as, for example, speech, saliva and drooling, chewing and swallowing, eating tasks, dressing, hygiene, handwriting, turning in bed, tremors, getting out of a bed, a car, or a deep chair, walking and balance, and freezing; (c) at least one motor symptom identified in Part III of the UPDRS, such as, for example, speech, facial expression, rigidity, finger tapping, hand movements, pronation-supination movements of hands, toe tapping, leg agility, arising from chair, gait, freezing of gait, postural stability, posture, body bradykinesia, postural tremor of the hands, kinetic tremor of the hands, rest tremor amplitude, and constancy of rest tremor; (d) at least one motor complication identified in Part IV of the UPDRS, such as for example, dyskinesias, functional impact of dyskinesias, time spent in the off state, functional impact of fluctuations, complexity of motor fluctuations, and painful off-state dystonia; (e) constipation; (f) depression; (g) cognitive impairment; (h) sleep problems or sleep disturbances; (i) circadian rhythm dysfunction; (j) hallucinations; (k) fatigue; (l) REM disturbed sleep; (m) REM behavior disorder; (n) erectile dysfunction; (o) apnea; (p) postural hypotension; (q) correction of blood pressure or orthostatic hypotension; (r) nocturnal hypertension; (s) regulation of temperature; (t) improvement in breathing or apnea; (u) correction of cardiac conduction defect; (v) amelioration of pain; (w) restoration of bladder sensation and urination; (x) urinary incontinence; and/or (y) control of nocturia.

IV. Methods of Treatment

Aspects of this disclosure relate to methods of treating certain symptoms and/or methods of treating and/or preventing diseases or disorders associated with one or more of these symptoms by administration of a therapeutically effective amount of a squalamine polymorph composition disclosed herein optionally present with one or more pharmaceutically acceptable carriers. The therapeutically effective amount can be as described herein, which includes but is not limited to a "fixed composition dosage" determined as described herein.

In one embodiment, the symptoms, diseases, and/or disorders are generally correlated with abnormal αS pathology and/or dopaminergic dysfunction, which means they are amenable to treatment with squalamine polymorph compositions described herein. The compositions of the present technology can be administered using any pharmaceutically acceptable method, including but not limited to oral, pulmonary, nasal, and nebularization administration. In yet another embodiment, administration comprises non-oral administration.

In some embodiments, provided herein are methods for treating a subject in need having a condition or symptom susceptible to treatment with a squalamine polymorph composition, comprising administering to the subject a therapeutically effective amount of a squalamine polymorph composition described herein, which optionally additionally comprises one or more pharmaceutically acceptable carriers and/or excipients. Non-limiting examples of symptoms amenable to treatment with compositions of the disclosure include but are not limited to constipation, hallucinations, sleep disorders, cognitive impairment, depression, and inflammation.

Examples of diseases amenable to treatment with squalamine polymorph compositions of the disclosure are described herein and include but are not limited to those described herein, such as neurological diseases, e.g., PD, AD, MSA, schizophrenia, Huntington's disease (HD), progressive supranuclear palsy, frontotemporal dementia (FTD), vascular dementia, amyotrophic lateral sclerosis (ALS), multiple sclerosis (MS), spinal muscular atrophy (SMA), Friedreich's ataxia. In another embodiment, the compositions can be used in methods of treating, preventing, and/or slowing the onset or progression of psychological or behavior disorder and/or a related symptom in a subject in need is provided. In one embodiment, the psychological or behavior disorder can be, for example, depression, anxiety, delirium, irritability, illusion and delusions, amnesia, autism, apathy, bipolar disorder, disinhibition, aberrant motor and obsessive-compulsive behaviors, sleep disorders, sleep fragmentation, REM behavior disorder, circadian rhythm dysfunction, sleep apnea, and cognitive impairment. In another embodiment, a method of treating, preventing, and/or slowing the onset or progression of a cerebral or general ischemic disorder and/or a related symptom in a subject in need is provided. The cerebral or general ischemic disorder can be, for example, microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, and pulmonary edema.

In one embodiment, a method of inhibiting protein tyrosine phosphatase 1B (PTP1B) is provided, comprising contacting PTP1B with at least one composition disclosed herein. In addition, as it has been shown that squalamine can increase transcription in the gut of old mice thus having a rejuvenating effect on the gut, in another aspect provided is a method of increasing transcription in the gut of a subject, the method comprising administering to the subject a therapeutically effective amount of a squalamine polymorph composition described herein.

A. Exemplary Symptoms Correlated with Abnormal αS Pathology and/or Dopaminergic Dysfunction and Amenable to Treatment (1) Constipation In one embodiment, a method of treating, preventing, and/or slowing the onset or progression of constipation and/or a related symptom in a subject in need is provided, comprising administering to the subject a therapeutically effective amount of at least one squalamine polymorph composition disclosed herein.

Constipation is defined as a lower than normal frequency of bowel movements in a fixed duration of time (e.g., less than 3 bowel movements per week). While often dismissed as strictly a gastrointestinal symptom, constipation is believed to be an early indicator of neurodegenerative disease to the extent that ENS degeneration can be indicative of later CNS degeneration. There is substantial evidence that the neurodegenerative process associated with PD, namely the accumulation of toxic aggregates of αS, occurs within the ENS years before they appear within the brain. Although the function of αS is not known, inflammation within the nervous system leads to an increase in its intracellular levels. In individuals with PD, the increase in αS leads to the formation of neurotoxic aggregates, perhaps because of a failure by the neuron (due to genetic factors) to effectively dispose of them. The aggregates of αS then traffic along the vagal nerve to the dorsal motor nucleus within the brainstem, and from there to more rostral structures. Accordingly, method embodiments disclosed herein relate to the treatment of constipation or the treatment and/or prevention of an underlying disorder associated with constipation using a squalamine polymorph.

Examples of characteristics of constipation that can be positively affected by squalamine polymorph treatment include, but are not limited to, frequency of constipation, duration of constipation symptoms, bowel movement frequency, stool consistency, abdominal pain, abdominal bloating, incomplete evacuation, unsuccessful attempts at evacuation, pain with evacuation, and straining with evacuation. Potentially all of these characteristics can be positively impacted by the methods of the disclosure. Further, assessments of these characteristics are known in the art, e.g., spontaneous bowel movements (SBMs)/week, stool consistency (Bristol Stool Form Scale), ease of passage (Ease of Evacuation Scale), rescue medication use and symptoms and quality of life related to bowel function (PAC-SYM and PAC-QOL).

The methods of using a therapeutically effective dose of a squalamine polymorph composition according to the disclosure to treat and/or prevent constipation preferably results in an increase in the number of spontaneous bowel movements per week and/or an improvement in other stool conditions. The increase can be, for example, an increase of between about 1 to about 3 spontaneous bowel movements in a week, or, optionally, full restoration of regular bowel function.

In one embodiment of the disclosure, treatment of a subject having constipation with a squalamine polymorph composition in a method described herein results in an improvement of one or more characteristics of constipation. The improvement can be, for example, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375 or about 400%.

(2) Hallucinations

In one embodiment, a method of treating, preventing, and/or slowing the onset or progression of hallucinations and/or a related symptom in a subject in need is provided, comprising administering to the subject a therapeutically effective amount of at least one squalamine polymorph composition disclosed herein (e.g., a crystalline hydrate).

A hallucination is a sensory impression or perception of an object or event, in any of the 5 senses (sight, touch, sound, smell, or taste) that has no basis in external stimulation. Examples of hallucinations include "seeing" someone not there (visual hallucination), "hearing" a voice not heard by others (auditory hallucination), "feeling" something crawling up your leg (tactile hallucination), "smelling" (olfactory), and "tasting" (gustatory). Other examples of hallucination types include hypnagogic hallucination (a vivid, dreamlike hallucination occurring at sleep onset), hypnopompic hallucination (a vivid, dreamlike hallucination occurring on awakening), kinesthetic hallucination (a hallucination involving the sense of bodily movement), and somatic hallucination (a hallucination involving the perception of a physical experience occurring within the body).

In some cases, hallucination is the result of a psychiatric or neurological disorder. The squalamine polymorph composition can, for example, reverse the dysfunction of the psychiatric or neurological disorder and treat the hallucination. The psychiatric disorder can be, for example, selected from the group consisting of bipolar disorder, borderline personality disorder, depression (mixed), dissociative identity disorder, generalized anxiety disorder, major depression, obsessive compulsive disorder, post-traumatic stress disorder, psychosis (NOS), schizoaffective disorder, and schizophrenia. The neurodegenerative disorder can be, for example, PD, supranuclear palsy, multi-system atrophy, Parkinsonism, Alzheimer's disease, frontotemporal dementia, amyotrophic lateral sclerosis (ALS), Huntington's disease, schizophrenia, Friedreich's ataxia, multiple sclerosis (MS), Lewy body dementia or disease, spinal muscular atrophy, frontotemporal dementia, progressive nuclear palsy, Guadeloupian Parkinsonism, spinocerebellar ataxia, or vascular dementia. In a preferred embodiment, the compositions of the disclosure reverse the dysfunction of the neurodegenerative disorder and treat the hallucination. The neurological disorder can also be, for example, the result of (a) a brain tumor, a sleep disorder such as narcolepsy, or a focal brain lesion, such as occipital lobe lesions or temporal lobe lesions. In an exemplary embodiment, the temporal lobe lesion can be lesions of the uncinate gyrus, cerebral peduncles, or substantia nigra. The neurological disorder can be, for example, the result of (d) a diffuse involvement of the cerebral cortex, such as that caused by a viral infectious disease.

In addition, the hallucinations may be caused by a sensory loss, which can be for example visual, auditory, gustatory, tactile, or olfactory. In a preferred embodiment, the compositions of the disclosure reverse the dysfunction of the sensory loss and treat the hallucination. In another preferred embodiment, the compositions of the disclosure reverse the dysfunction of the enteric nervous system and treat the hallucination.

The methods of using a therapeutically effective amount of a squalamine polymorph composition according to the disclosure to treat and/or prevent hallucinations preferably result in a decrease in hallucinations. The decrease can be, for example, a reduction in occurrences of hallucinations by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The methods of the disclosure may also result in the subject being hallucination-free. The hallucination can comprise, for example, a visual, auditory, tactile, gustatory or olfactory hallucination. The improvement can be measured using any clinically recognized assessment or tool.

(3) Inflammation Related to Abnormal αS Pathology and/or Dopaminergic Dysfunction and Amenable to Treatment In one embodiment, provided is a method of treating, preventing, and/or slowing the onset or progression in a subject of inflammation and/or a related symptom related to αS pathology. The method comprises administering to the subject a therapeutically effective amount of at least one squalamine polymorph composition disclosed herein (e.g., a crystalline hydrate).

The inflammatory disease or condition caused by excessive expression of neuronal αS can be a neurodegenerative disorder (NDD), such as an alpha-synucleinopathy. Exemplary alpha-synucleinopathies include, but are not limited to, PD, Lewy body dementia, multiple system atrophy, amyotrophic lateral sclerosis, Huntington's chorea, multiple sclerosis or schizophrenia. In other embodiments, the inflammatory disease or condition caused by excessive expression of neuronal α-synuclein can be an autoimmune disease, a chronic inflammatory disease, or an autoinflammatory disease. In other embodiments, the inflammatory disease or condition caused by excessive expression of neuronal αS can be selected from the group consisting of asthma, chronic peptic ulcer, tuberculosis, chronic periodontitis, chronic sinusitis, chronic active hepatitis, psoriatic arthritis, gouty arthritis, acne vulgaris, osteoarthritis, rheumatoid arthritis, lupus, systemic lupus erythematosus, multiple sclerosis, ankylosing spondylitis, Crohn's disease, psoriasis, primary sclerosing cholangitis, ulcerative colitis, allergies, inflammatory bowel diseases, Celiac disease, chronic prostatitis, diverticulitis, dermatomyositis, polymyositis, systemic sclerosis, glomerulonephritis, hidradenitis suppurativa, hypersensitivities, interstitial cystitis, otitis, pelvic inflammatory disease, reperfusion injury, rheumatic fever, sarcoidosis, transplant rejection, and vasculitis.

In some embodiments of the disclosure, patient populations particularly susceptible to excessive production or secretion of αS can benefit from the methods of the disclosure and are targeted for therapy, including for example preventative therapy. For example, a patient population having a mutated form of αS resulting in increased amounts of αS in tissues can be treated using the methods of the disclosure. Another example of a patient population susceptible for high levels of αS are patients having chronic inflammatory conditions or diseases. A still further example is a patient population having elevated levels of αS aggregation in their enteric nerve cells, manifesting as a constipation.

The methods of the disclosure can result in a decrease in intensity of inflammation, blood levels of inflammatory markers, inflammatory markers in tissue, or number of inflammatory cells in tissue, or a combination thereof, as compared to a control or as compared to the qualitative or quantitative amount from the same patient or subject prior to treatment. For example, the decrease can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

In addition, an individual with an inflammatory condition appropriate for treatment or prophylaxis with the methods targeting αS described herein can be identified by determination of the tissue concentrations of αS at sites of inflammation, with high levels of αS, as compared to a control or healthy subject, correlating with patients appropriate for treatment with a method of the disclosure.

It is theorized that administration of a squalamine polymorph composition reduces the formation of neurotoxic αS aggregates in vivo, and stimulates gastrointestinal motility in patients with neurodiseases such as PD and constipation. It is also hypothesized that the greater the burden of αS impeding neuronal function, the higher the dose of composition required to restore normal bowel function as well as address other symptoms of αS aggregation.

B. Exemplary Diseases or Disorders Correlated with Abnormal αS Pathology and/or Dopaminergic Dysfunction and Amenable to Treatment The squalamine polymorph compositions described herein can be used in methods of treating and/or preventing a variety of diseases and disorders, which are generally correlated with abnormal αS pathology and/or dopaminergic dysfunction, as described herein.

In one embodiment, provided is a method of treating, preventing, and/or slowing the onset or progression in a subject of a disease or disorder correlated with abnormal αS pathology and/or dopaminergic dysfunction and/or a related symptom related to αS pathology. The method comprises administering to the subject a therapeutically effective amount of at least one squalamine polymorph composition disclosed herein (e.g., a crystalline hydrate).

(1) Neurological or Neurodegenerative Disorders or Diseases

The methods and compositions of the disclosure can be used to treat and/or prevent neurological disorders or diseases such as those described herein, examples of which include but are not limited to AD, PD, Huntington's Disease, Multiple Sclerosis, Amyotorphic Lateral Sclerosis (ALS), multiple system atrophy (MSA), schizophrenia, Friedreich's ataxia, vascular dementia, Lewy Body dementia or disease, spinal muscular atrophy, supranuclear palsy, frontotemporal dementia, progressive nuclear palsy, Guadeloupian Parkinsonism, spinocerebellar ataxia, and autism.

A variety of neuroimaging techniques may be useful for the early diagnosis and/or measurement of progression of neurodegenerative disorders. Examples of such techniques include but are not limited to neuroimaging, functional MRI, structural MRI, diffusion tensor imaging (DTI) (including for example diffusion tensor measures of anatomical connectivity), [18F]fluorodeoxyglucose (FDG) PET, agents that label amyloid, [18F]F-dopa PET, radiotracer imaging, volumetric analysis of regional tissue loss, specific imaging markers of abnormal protein deposition (e.g., for AD progression), multimodal imaging, and biomarker analysis.

In one embodiment, the progression or onset of a neurodegenerative disorder is slowed or prevented over a defined time period, following administration of a therapeutically effective amount of a squalamine polymorph composition to a subject in need, as measured by a medically-recognized technique. For example, the progression or onset of a neurodegenerative disorder can be slowed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The period of time over which the progression or onset of a neurodegenerative disorder is measured can be for example, one or more months or one or more years, e.g., about 6 months, about 1 year, about 18 months, about 2 years, about 36 months, about 3, about 4, about 5, about 6, about 7, about 8, about 9, about 10, about 11, about 12, about 13, about 14, about 15, about 16, about 17, about 18, about 19, or about 20 years, or any amount of months or years in between the values of about 6 months to about 20 years or more.

In another embodiment, a neurodegenerative disorder may be positively impacted by administration of a therapeutically effective amount of a squalamine polymorph composition according to the disclosure. A "positive impact" includes for example slowing advancement of the condition, improving one or more symptoms, etc.

(i) Parkinson's Disease

In one embodiment, a method of treating, preventing, and/or slowing the onset or progression of PD and/or a related symptom in a subject in need is provided, comprising administering to the subject a therapeutically effective amount of at least one squalamine polymorph composition disclosed herein (e.g., a crystalline hydrate).

PD is divided into three stages: preclinical (in which neurodegenerative process is started without evident symptoms or signs); prodromal (in which symptoms and signs are present but insufficient to define a full clinical PD diagnosis); and clinical (in which the diagnosis is achieved based on the presence of classical motor signs).

PD may also be assessed using the Unified Parkinson's Disease Rating Scale (UPDRS), which consists of 42 items in four subscales: (1) Part I, Non-Motor Aspects of Experiences of Daily Living (nM-EDL): cognitive impairment (section 1.1), hallucinations and psychosis (section 1.2), depressed mood (section 1.3), anxious mood (section 1.4), apathy (section 1.5), features of dopamine dysregulation syndrome (section 1.6), sleep problems (section 1.7), daytime sleepiness (section 1.8), pain and other sensations (section 1.9), urinary problems (section 1.10), constipation problems (section 1.11), light headedness on standing (section 1.12), and fatigue (section 1.13); (2) Part II, Motor Aspects of Experiences of Daily Living (M-EDL): speech (section 2.1), saliva & drooling (section 2.2), chewing and swallowing (section 2.3), eating tasks (section 2.4), dressing (section 2.5), hygiene (section 2.6), handwriting (section 2.7), doing hobbies and other activities (section 2.8), turning in bed (section 2.9), tremor (section 2.10), getting out of bed, a car, or a deep chair (section 2.11), walking and balance (section 2.12), and freezing (section 2.13); Part III, Motor Examination: speech (section 3.1), facial expression (section 3.2), rigidity (section 3.3), finger tapping (section 3.4), hand movements (section 3.5), pronation-supination movements of hands (section 3.6), toe tapping (section 3.7), leg agility (section 3.8), arising from chair (section 3.9), gait (3.10), freezing of gait (section 3.11), postural stability (section 3.12), posture (section 3.13), global spontaneity of movement (body bradykinesia) (section 3.14), postural tremor of the hands (section 3.15), kinetic tremor of the hands (section 3.16), rest tremor amplitude (section 3.17), and constancy of rest tremor (section 3.18); Part IV, Motor Complications: time spent with dyskinesias (section 4.1), functional impact of dyskinesias (section 4.2), time spent in the off state (section 4.3), functional impact of fluctuations (section 4.4), complexity of motor fluctuations (section 4.5), and painful off-state dystonia (section 4.6).

Further, symptom-based endpoints can be assessed using known scales. For example, (1) depression can be assessed using the Beck Depression Inventory (BDI-II), cognition can be assessed using the Mini Mental State Examination (MMSE), sleep and REM-behavior disorder (RBD) can be assessed using a daily diary and an RBD questionnaire (RBDQ), and hallucinations can be assessed using the PD hallucinations questionnaire (PDHQ) and direct questioning. Circadian system status can also be assessed by continuously monitoring wrist skin temperature (Thermochron iButton DS1921H; Maxim, Dallas) following published procedures.

In another embodiment, administration of a therapeutically effective amount of a squalamine polymorph composition described herein to a PD patient results in improvement of one or more symptoms of PD or on one or more clinically accepted scoring metrics, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

PD progression and treatment is particularly difficult in view of patients' development of resistance to dopamine and subsequent dose escalation until no response can be elicited. Not to be bound by theory, it is believed that prior or co-administration of a squalamine polymorph composition according to the disclosure (e.g., a crystalline hydrate) may reduce the dopamine dosage required to elicit a therapeutic effect for Parkinson's symptoms and/or increase the period during which the patient is sensitive to dopamine. It is also theorized that prior or co-administration of a composition according to the disclosure may delay the time period when a patient is advised to begin dopamine therapy. This is significant, as currently patients are encouraged to delay initiation of dopamine treatment as long as possible, as after a period of time subjects become resistant to dopamine.

(ii) Alzheimer's Disease

In one embodiment, a method of treating, preventing, and/or slowing the onset or progression of AD and/or a related symptom in a subject in need is provided, comprising administering to the subject a therapeutically effective amount of at least one squalamine polymorph composition disclosed herein (e.g., a crystalline hydrate).

Unambiguous diagnosis of AD requires clinical findings of cognitive deficits consistent with AD and post-mortem identification of brain pathologies consistent with AD. The term AD dementia is used to describe dementia that is due to the pathophysiologies of AD. The term "probable Alzheimer's disease" is used in life when a subject demonstrates clinical characteristics of AD and when other possible biological causes of dementia (e.g., PD or stroke) are excluded. The criteria for 'probable AD' are described a National Institute of Aging-Alzheimer's Association workgroup (McKhann et al. 2011). Cognitive ability/impairment may be determined by art-accepted methods, including, but not limited to, validated instruments that assess global cognition (e.g., the Modified Mini Mental State Examination (3MS-E)), and specific domains such as visual and verbal memory (e.g., the Brief Visuospatial Memory Test (Revised) (BVMT-R) and the Hopkins Verbal Learning Test (Revised) (HVLT-R), respectively), language (e.g., the Generative Verbal Fluency Test (GVFT)) and executive function and attention (e.g., the Digit Span Test (DST)). Dementia due to AD is also defined by insidious onset and a history of worsening cognitive performance.

In another embodiment, administration of a therapeutically effective amount of a squalamine polymorph composition to an AD patient results in improvement of one or more symptoms of AD or on one or more clinically accepted scoring metrics, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

(iii) Multiple System Atrophy

In one embodiment, a method of treating, preventing, and/or slowing the onset or progression of multiple system atrophy (MSA) and/or a related symptom in a subject in need is provided, comprising administering to the subject a therapeutically effective amount of at least one squalamine polymorph composition disclosed herein (e.g., a crystalline hydrate).

Multiple system atrophy (MSA) is a progressive neurodegenerative disorder characterized by a combination of symptoms that affect both the autonomic nervous system (the part of the nervous system that controls involuntary action such as blood pressure or digestion) and movement. MSA, also known as Shy-Drager syndrome, is a neurodegenerative disorder characterized by tremors, slow movement, muscle rigidity, and postural instability (collectively known as parkinsonism) due to dysfunction of the autonomic nervous system, and ataxia. Progression of neurodegeneration can be measured using well known techniques.

In another embodiment, administration of a therapeutically effective amount of a squalamine polymorph composition to an MSA patient results in improvement of one or more symptoms of MSA, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Improvement can be measured using any clinically recognized tool or assessment.

(iv) Schizophrenia

In one embodiment, a method of treating, preventing, and/or slowing the onset or progression of schizophrenia (SZ) and/or a related symptom in a subject in need is provided, comprising administering to the subject a therapeutically effective amount of at least one squalamine polymorph composition disclosed herein (e.g., a crystalline hydrate).

Schizophrenia is a chronic progressive disorder that has at its origin structural brain changes in both white and gray matter. It is likely that these changes begin prior to the onset of clinical symptoms in cortical regions. Later, they can be detected by progressive ventricular enlargement. A 2013 study of schizophrenia patients documented brain changes seen in MRI scans from more than 200 patients beginning with their first episode and continuing with scans at regular intervals for up to 15 years. The scans showed that people at their first episode had less brain tissue than healthy individuals. The findings suggest that those who have schizophrenia are being affected by something before they show outward signs of the disease. The mainstay of treatment is antipsychotic medication. However, the 2013 study found that in general, the higher the anti-psychotic medication doses, the greater the loss of brain tissue.

While not wishing to be bound by theory, it is theorized that administration of a therapeutically effective amount of a composition to a schizophrenia patient may treat and/or prevent schizophrenia or any one or more symptoms thereof. In some embodiments, the administration may be oral, resulting in absorption in the ENS. In some embodiments, the administration may be intranasal, resulting in stimulation of neurogenesis, which has a positive impact on the loss of brain tissue characteristic of schizophrenia subjects.

In one embodiment, administration of a therapeutically effective amount of a composition to a schizophrenia patient results in improvement of one or more symptoms as determined by a clinically recognized psychiatric symptom rating scale. In another embodiment, administration of a therapeutically effective amount of a composition disclosed herein to a schizophrenia patient results in improvement of one or more symptoms as determined by a clinically recognized psychiatric symptom rating scale, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Improvement can be measured using any clinically recognized tool, scale, or assessment.

(v) Other Neurodiseases

The methods and compositions of the disclosure may also be useful in treating and/or preventing a variety of other neurodiseases. In one embodiment, provided is a method of treating, preventing, and/or slowing the onset or progression of a neurodisease described herein, and/or a related symptom, in a subject in need, comprising administering to the subject a therapeutically effective amount of at least one squalamine polymorph composition disclosed herein (e.g., a crystalline hydrate). Examples of exemplary neurodiseases include but are not limited to Huntington's disease (HD), progressive supranuclear palsy, also called Steele-Richardson-Olszewski syndrome, Frontotemporal dementia (FTD), vascular dementia, also known as multi-infarct dementia (MID) and vascular cognitive impairment (VCI), Amyotrophic lateral sclerosis (ALS), also known as motor neuron disease (MND) or Lou Gehrig's disease, Multiple sclerosis (MS), spinal muscular atrophy (SMA), and Friedreich's ataxia.

(2) Psychological or Behavior Disorders and/or a Related Symptom

In one embodiment, a method of treating, preventing, and/or slowing the onset or progression of psychological or behavior disorder and/or a related symptom in a subject in need is provided, comprising administering to the subject a therapeutically effective amount of at least one squalamine polymorph composition disclosed herein (e.g., a crystalline hydrate). In one embodiment, the psychological or behavior disorder is depression, anxiety, delirium, irritability, illusion and delusions, amnesia, autism, apathy, bipolar disorder, disinhibition, aberrant motor and obsessive-compulsive behaviors, sleep disorders, sleep fragmentation, REM behavior disorder, circadian rhythm dysfunction, sleep apnea, or cognitive impairment.

(i) Depression

In one embodiment, a method of treating, preventing, and/or slowing the onset or progression of depression and/or a related symptom in a subject in need is provided, comprising administering to the subject a therapeutically effective amount of at least one squalamine polymorph composition disclosed herein (e.g., a crystalline hydrate).

Clinical depression is characterized by a sad, blue mood that goes above and beyond normal sadness or grief. Major depression is an episode of sadness or apathy along with other symptoms that lasts at least two consecutive weeks and is severe enough to interrupt daily activities. Research shows that the hippocampus is smaller in some depressed people. For example, in one study where investigators studied 24 women who had a history of depression, it was found that on average, the hippocampus was 9% to 13% smaller in depressed women as compared with those who were not depressed. The more bouts of depression a woman had, the smaller the hippocampus. Researchers are exploring possible links between sluggish production of new neurons in the hippocampus and low moods. An interesting fact about antidepressants supports this theory. These medications immediately boost the concentration of chemical messengers in the brain (neurotransmitters). Yet people typically don't begin to feel better for several weeks or longer. Experts have long wondered why, if depression were primarily the result of low levels of neurotransmitters, people don't feel better as soon as levels of neurotransmitters increase. The answer may be that mood only improves as nerves grow and form new connections, a process that takes weeks. In fact, animal studies have shown that antidepressants spur the growth and enhanced branching of nerve cells in the hippocampus. Thus, the real value of these medications may be in generating new neurons, e.g., neurogenesis, strengthening nerve cell connections, and improving the exchange of information between nerve circuits.

In one embodiment, encompassed are methods of treating and/or preventing depression comprising administering therapeutically effective amount of a squalamine polymorph composition according to the disclosure. While not wishing to be bound by theory, it is theorized that the squalamine polymorph compositions of the disclosure trigger neurogenesis, which functions to combat depression. In some embodiments, the methods of the disclosure produce an improvement in a subject's clinical depression. An improvement in a subject's depression can be measured using any clinically-recognized measurement. For example, improvement can be measured using a depression rating scale. In one embodiment of the disclosure, following treatment a subject experiences an about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or an about 100% improvement.

(ii) Cognitive Impairment

In one embodiment, a method of treating, preventing, and/or slowing the onset or progression of cognitive impairment (CI) and/or a related symptom in a subject in need is provided, comprising administering to the subject a therapeutically effective amount of at least one squalamine polymorph composition disclosed herein (e.g., a crystalline hydrate).

CI, including mild cognitive impairment (MCI), is characterized by increased memory or thinking problems exhibited by a subject as compared to a normal subject of the same age. MCI is a clinical diagnosis. A combination of cognitive testing and information from a person in frequent contact with the subject is used to fully assess CI. For example, the Mini Mental State Examination (MMSE) may be used. With the MMSE, a score of 24 or greater (out of 30) may indicate normal cognition, with lower scores indicating severe (less than or equal to 9 points), moderate (10-18 points), or mild (19-23 points) cognitive impairment. Other screening tools include the Informant Questionnaire on Cognitive Decline in the Elderly (IQCODE), the 7-Minute Screener, Abbreviated Mental Test Score (AMTS), Cambridge Cognitive Examination (CAMCOG), Clock Drawing Test (CDT), General Practitioner Assessment of Cognition (GPCOG), Mini-Cog, Memory Impairment Screen (MIS), Montreal Cognitive Assessment (MoCA), Rowland Universal Dementia Assessment (RUDA), Self-Administered Gerocognitive Examination (SAGE), Short and Sweet Screening Instrument (SAS-SI), Short Blessed Test (SBT), St. Louis Mental Status (SLUMS), Short Portable Mental Status Questionnaire (SPMSQ), Short Test of Mental Status (STMS), or Time and Change Test (T&C). Improvements in score on any standardized examination indicate successful treatment of cognitive impairment, whereas obtaining a score comparable to the non-impaired population indicates total recovery.

In some embodiments, administration of a therapeutically effective amount of a squalamine polymorph composition disclosed herein to a patient in need results in improvement of CI as determined by a clinically recognized assessment scale, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

(iii) Sleep Disturbance/Sleep Problems (e.g., REM Disturbed Sleep or Circadian Rhythm Dysfunction)

In one embodiment, a method of treating, preventing, and/or slowing the onset or progression of a sleep disturbance, sleep problem, sleep disorder, circadian rhythm dysfunction, and/or a related symptom in a subject in need is provided, comprising administering to the subject a therapeutically effective amount of at least one squalamine polymorph composition disclosed herein (e.g., a crystalline hydrate).

Sleep disorders and/or sleep disturbances include but are not limited to REM-behavior disorders, disturbances in the Circadian rhythm ("circadian rhythm dysfunction"), delayed sleep onset, sleep fragmentation, REM-behavior disorder (RBD), and hallucinations. Other sleep disorders or disturbances that can be treated and/or prevented according to the disclosed methods include but are not limited to hypersomnia (i.e., daytime sleepiness), parasomnias (such as nightmares, night terrors, sleepwalking, and confusional arousals), periodic limb movement disorders (such as Restless Leg Syndrome), jet lag, narcolepsy, advanced sleep phase disorder, and non-24 hour sleep-wake syndrome.

Normal sleep is critically important for the proper functioning of many organ systems, the most important of which is the brain. Disturbances in normal sleep patterns are closely associated with the normal aging process, with the development of CI, with impaired memory deposition and consolidation and with the occurrence of neurodevelopmental, neuroaffective and neurodegenerative disorders. The alternating pattern of sleep and wakefulness occurring every 24 hours is known as the circadian rhythm. The rhythm is set by the "zeitgeber" (time setter), an entity known as the suprachiasmatic nucleus (SCN) and located in the hypothalamus. The SCN is normally "entrained" or synchronized by the external light-dark cycle. This relationship between external light and dark and the sleep-wake cycle synchronized to it by the SCN can be overridden during periods of hunger by neural signals emanating in the gut and relayed to the hypothalamus. The circadian sleep-wake cycle can also shift in response to changes in external light-dark cycles, such as the desynchronization that occurs during travel from one time zone to another (jet-lag). Under such circumstances, a progressive adjustment occurs until the SCN is resynchronized with the external light-dark cycle. A similar "phase-shift" and adjustment occurs in night-shift workers.

Dysfunction of the circadian rhythm manifests as abnormal sleep patterns. Common symptoms of sleep disorder include a delay in the onset of sleep and sleep fragmentation, meaning that the individual awakens several times during the course of the night. Total sleep time, calculated by subtracting total time of the awake fragments from total time spent in bed, also diminishes with age, from about 14 to about 16 hours a day in newborns, to about 12 hours by one year of age, to about 7 to about 8 hours in young adults, progressively declining to about 5 to about 6 hours in elderly individuals. Total sleep time can be used to calculate an individual's "sleep age" and to compare it to their chronologic age. Significant discrepancies between sleep age and chronologic age are a reflection of the severity of the sleep disorder. "Sleep efficiency," defined as the percentage of the time spent in bed asleep is another index that can be used to determine the severity of the sleep disorder. Sleep efficiency is said to be abnormal when the percentage is below about 70%.

A "normal" or "restful" sleep period is defined as a sleep period uninterrupted by wakefulness. Alternatively, a sleep period can be defined by the recommended or appropriate amount of sleep for the subject's age category, e.g., (i) infants 0-3 months=about 11 to about 19 hours; (ii) infants about 4 to about 11 months=about 12 to about 18 hours; (iii) toddlers about 1 to about 2 years=about 9 to about 16 hours; (iv) preschoolers about 3 to about 5 years=about 10 to about 14 hours; (v) school-aged children about 6 to about 13 years=about 7 to about 12 hours; (v) teenagers about 14 to about 17 years=about 7 to about 11 hours; (vi) young adults about 18 to about 25 years=about 6 to about 11 hours; (vii) adults about 26 to about 64 years=about 6 to about 10 hours; and (viii) older adults ≥65 years=about 5 to about 9 hours. Thus, for treating sleep disturbance in a subject, the treatment can result in a restful sleep period of at least about 4, about 5, about 6, about 7, about 8, about 9, about 10, about 11, or about 12 hours.

In some embodiments, administration of a therapeutically effective amount of a squalamine polymorph composition disclosed herein to a patient with disturbed results in improvement in frequency of normal or restful sleep as determined by a clinically recognized assessment scale for one or more types of sleep dysregulation by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The improvement can be measured using any clinically recognized tool or assessment.

(iv) Autism

In one embodiment, a method of treating, preventing, and/or slowing the onset or progression of autism spectrum disorder (ASD) and/or a related symptom in a subject in need is provided, comprising administering to the subject a therapeutically effective amount of at least one squalamine polymorph composition disclosed herein (e.g., a crystalline hydrate).

Autism, or autism spectrum disorder, refers to a range of conditions characterized by challenges with social skills, repetitive behaviors, speech and nonverbal communication, as well as by unique strengths and differences. There are many types of autism, caused by different combinations of genetic and environmental influences. Autism's most obvious signs tend to appear between 2 and 3 years of age. In some cases, it can be diagnosed as early as 18 months.

Experts are still uncertain regarding the causes of autism. A number of different circumstances, including environmental, biologic, and genetic factors, set the stage for autism and make a child more likely to have the disorder. A recent brain-tissue study suggests that children affected by autism have a surplus of synapses, or connections between brain cells. The excess is due to a slowdown in the normal pruning process that occurs during brain development. During normal brain development, a burst of synapse formation occurs in infancy. This is particularly pronounced in the cortex, which is central to thought and processing information from the senses. However, by late adolescence, pruning eliminates about half of these cortical synapses. In addition, many genes linked to autism are known to affect the development or function of brain synapses. It has also been reported that the brain cells from individuals with autism were filled with damaged parts and deficient in signs of a normal breakdown pathway called "autophagy."

One embodiment is directed to methods of treating autism comprising administering a therapeutically effective amount of a squalamine polymorph composition according to the disclosure. In one embodiment, treatment results in improvement in one or more characteristics of autism. Such characteristics can be, for example, communication skills, social interaction, sensory sensitivity, and behavior. Improvement can be measured using any clinically recognized tool or assessment.

For example, the methods may show an improvement in one or more characteristics of autism, such as behavior, communication, mood, etc., as measured by a medically recognized scale. The improvement may be, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The medically recognized scale may be selected from, for example, Childhood Autism Rating Scale (CARS), Autism Spectrum Rating Scales, or The Michigan Autism Spectrum Questionnaire.

(3) Cerebral or General Ischemic Disorder and/or a Related Symptom

In one embodiment, a method of treating, preventing, and/or slowing the onset or progression of a cerebral or general ischemic disorder and/or a related symptom in a subject in need is provided, comprising administering to the subject a therapeutically effective amount of at least one squalamine polymorph composition disclosed herein (e.g., a crystalline hydrate).

In one embodiment, the cerebral or general ischemic disorder can be microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, or pulmonary edema.

For example, the methods of the disclosure may show an improvement in one or more characteristics of the cerebral or general ischemic disorder as measured by a medically recognized scale. The improvement may be, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Medically recognized scales or techniques to measure improvement include, for example, cholesterol test, high-sensitivity C-reactive protein test, lipoprotein (a), plasma ceramides, natriuretic peptides, low density lipoprotein cholesterol, high density lipoprotein cholesterol, triglycerides, electrocardiogram (EKG), Holter monitor, stress test, echocardiogram, positron emission tomography (PET), thallium scans, myocardial perfusion scans, implantable loop recorder, tilt table test, electrophysiology study, coronary angiogram, magnetic resonance imaging, magnetic resonance angiography, cardiac CT scan, and event recorder.

(i) Erectile Dysfunction

In one embodiment, a method of treating, preventing, and/or slowing the onset or progression of erectile dysfunction (ED) and/or a related symptom in a subject in need is provided, comprising administering to the subject a therapeutically effective amount of at least one squalamine polymorph composition disclosed herein (e.g., a crystalline hydrate).

Erectile dysfunction can be a sign of a physical or psychological condition. The main symptom is a man's inability to get or keep an erection firm enough for sexual intercourse. ED can manifest through different mechanisms. Based on its mechanism, ED can be classified as psychogenic, neurogenic (failure to initiate erection), artereogenic (failure of the penis to fill with blood), or cavernosal (failure of vascular system to retain blood in penis once filled) (Dean et al. 2005).

Many neurodiseases causing ED such as PD are suspected to correlate with the formation of toxic αS aggregates within the enteric nervous system (ENS). ED has been reported to affect in the range of 60-79% of men having PD, while the prevalence of ED in non-Parkinson men is only about 37.5%. As a result of the normal trafficking of αS aggregates from the ENS to the central nervous system (CNS) via afferent nerves such as the vagus, neurotoxic aggregates accumulate progressively within the brainstem and more rostral structures. Inhibiting αS aggregation in the ENS may, thus, reduce the continuing neuro disease process in both the ENS and CNS, and thereby positively impact ED associated with abnormal αS pathology.

It is known that central dopamine is a key neurotransmitter in the control of sexual function including erection. It is thought that dopamine deficiency may be responsible for erectile dysfunction often observed in PD patients. In patients with PD, αS-related pathology develops in serotonergic and cholinergic neurons in parallel with that seen in the nigral dopamine neurons. Thus, regulation of αS may play a role in ED in PD via dopaminergic dysfunction.

In one embodiment, the method results in a decrease in the number of instances in which the subject cannot attain erection, and the decrease in number of instances in which the subject cannot attain erection comprises a reduction in number of instances in which the subject cannot attain erection over a defined period of time. In another aspect, the method results in a decreased severity of ED over a defined period of time, wherein the decreased severity of ED is measured by a medically recognized technique selected from the group consisting of bone-pressed erect length (BPEL) measurement, girth measurement, Erection Hardness Scale (EHS), and International Index of Erectile Function (IIEF).

(ii) Blood Pressure

In one embodiment, a method of treating, preventing, and/or slowing the onset or progression of high blood pressure (HBP) or low blood pressure (LBP) and/or a related symptom in a subject in need is provided, comprising administering to the subject a therapeutically effective amount of at least one squalamine polymorph composition disclosed herein (e.g., a crystalline hydrate).

High blood pressure (HBP) or hypertension is a medical condition in which the blood pressure in the arteries is persistently elevated. Long-term high blood pressure is a major risk factor for coronary artery disease, stroke, heart failure, atrial fibrillation, peripheral vascular disease, vision loss, chronic kidney disease, and dementia. HBP may be characterized as (a) a systolic blood pressure (BP) $\geq 120$ and a diastolic BP$<80$; or (b) a systolic blood pressure (BP) $\geq 130$ or a diastolic BP$\geq 80$; while low blood pressure (LBP) may be characterized as (a) a systolic blood pressure $\leq 80$; or (b) a diastolic blood pressure $\leq 50$.

Low blood pressure (LBP) or hypotension is generally classified as a systolic blood pressure of less than 90 millimeters of mercury (mm Hg) or diastolic of less than 60 mm Hg. Primary symptoms include lightheadedness, vertigo and fainting. Severely low blood pressure can deprive the brain and other vital organs of oxygen and nutrients, leading to a life-threatening condition called shock. For some people who exercise and are in top physical condition, low blood pressure is a sign of good health and fitness.

Many neurodiseases causing HBP or LBP, such as PD, are suspected to correlate with the formation of toxic αS aggregates within the ENS. Studies suggest that a persistent hypertension can cause abnormal accumulation of phosphorylated αS in rats. Also, mice genetically engineered to overexpress human αS showed differing cardiac responses to chemically induced hypotension compared to wildtype mice. Neurodegenerative conditions such as PD may cause damage to brain centers responsible for autonomic processing, essential for regulation of blood pressure. It is believed that aminosterols such as squalamine polymorphs capable of treating or preventing neurodegeneration in PD, may prevent or treat the degeneration of neuronal structure that governs regulation of blood pressure either directly or indirectly via the regulation of hormones.

In one embodiment, in a subject having HBP, the method lowers the systolic and/or diastolic blood pressure by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale or tool.

In one embodiment, in a subject having LBP, the method raises the systolic and/or diastolic blood pressure by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale or tool.

In one embodiments, the clinically recognized scale or tool is selected from the group consisting of sphygmomanometry, arterial penetration, palpitation, asuculatoration, oscillometry, continuous noninvasive arterial pressure (CNAP), pulse wave velocity, and ambulatory monitoring.

(iii) Cardiac Conduction Defects

In one embodiment, a method of treating, preventing, and/or slowing the onset or progression of cardiac conduction defects (CCDs) and/or a related symptom in a subject in need is provided, comprising administering to the subject a therapeutically effective amount of at least one squalamine polymorph composition disclosed herein (e.g., a crystalline hydrate).

Cardiac conduction defects (CCDs) involve an aberration in how electrical impulses travel to and through the heart. The cardiac conduction system transmits electrical signals generated usually by the sinoatrial node to cause contraction of cardiac muscle. Cardiac conduction defect (CCD) is a serious and potentially life-threatening disorder. It belongs to a group of pathologies with an alteration of cardiac conduction through the atrioventricular (AV) node, the His-Purkinje system with right or left bundle branch block, and widening of QRS complexes in the electrocardiogram (EKG). The pathophysiological mechanisms underlying CCD are diverse, but the most frequent form of CCD is a degenerative form also called Lenègre-Lev disease (idiopathic bilateral bundle branch fibrosis).

In one embodiment, the CCD includes or results in (a) QT interval (QTc) ≥440 ms; (b) syncope; (c) presence of delta wave in electrocardiogram (EKG); (d) pseudo-right bundle branch block in EKG; (e) ST elevations in V1-V3 in EKG; (f) a QRS complex >100 ms in EKG; (g) PR interval <120 ms in EKG; (h) heart rate above 100 beats per minute (BPM); (i) heart rate below 60 BPM; (j) PR interval >200 ms in EKG; (k) QRS not following a P wave in EKG; (1) no repeating relation between P wave and QRS complex in EKG; (m) differing atrial and ventricular rates; (n) QS or rS complex in lead V1 in EKG; (o) notched ('M'-shaped) R wave in lead V6; (p) T wave discordance in EKG; (q) left axis deviation between −45° and −60° in EKG; (r) qR pattern (small q, tall R) in the lateral limb leads I and aVL in EKG; (s) rS pattern (small r, deep S) in the inferior leads II, III, and aVF in EKG; (t) delayed intrinsicoid deflection in lead aVL (>0.045 s) in EKG; (u) frontal plane axis between 90° and 180° in EKG; (v) rS pattern in leads I and aVL in EKG; (w) qR pattern in leads III and aVF in EKG; (x) chest pain; (y) palpitations; (z) difficulty breathing; (aa) rapid breathing; (bb) nausea; (cc) fatigue; (dd) sleep problem, sleep disorder, or sleep disturbance; (ee) constipation; and (ff) cognitive impairment.

In one embodiment, progression or onset of CCD is slowed, halted, or reversed over a defined period of time following administration of the squalamine polymorph composition, as measured by a medically-recognized technique. In addition, the CCD can be positively impacted by the dose of the squalamine polymorph composition or a salt or derivative thereof, as measured by a medically-recognized technique. The positive impact and/or progression of CCD can be measured quantitatively or qualitatively by one or more techniques selected from the group consisting of echocardiography, electrocardiography (ECG or EKG), magnetic resonance imaging (MRI), positron-emission tomography (PET); coronary catheterization, intravascular ultrasound, Holter monitoring, stress test, computed tomography angiography (CTA), and coronary CT calcium scan. In addition, the progression or onset of CCD can be slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique.

In another embodiment, the squalamine polymorph composition reverses dysfunction caused by the CCD and treats, prevents, improves, and/or resolves the symptom being evaluated. The improvement or resolution of the CCD symptom is measured using a clinically recognized scale or tool. In addition, the improvement in the CCD symptom can be at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using, for example, the techniques described above.

V. Patient Populations

The disclosed squalamine polymorphs and compositions can be used to treat a range of subjects, including human and non-human animals, including mammals, as well as immature and mature animals, including human children and adults. The human subject to be treated can be an infant, toddler, school-aged child, teenager, young adult, adult, or elderly patient.

In embodiments disclosed herein relating to prevention, particular patient populations may be selected based on being "at risk for" the development of any of the conditions disclosed herein. For example, genetic markers of the condition or family history may be used as signs to identify subjects likely to develop the particular condition. Thus, in some embodiments, prevention may involve first identifying a patient population at risk of developing the condition. Alternatively, certain symptoms are considered early signs of particular disorders. Thus, in some embodiments, a patient population may be selected for being "at risk" for developing the condition based on age and experiencing symptoms associated with the condition. Further genetic or hereditary signs may be used to refine the patient population.

VI. Kits

Squalamine polymorph compositions of the disclosure may be packaged together with or included in a kit along with instructions or a package insert. Such instructions or package inserts may address recommended storage conditions, such as time, temperature and light, taking into account the shelf-life of the composition or derivatives or salts thereof. Such instructions or package inserts may also address the particular advantages of the composition or derivatives or salts thereof, such as the ease of storage for formulations that may require use in the field, outside of controlled hospital, clinic or office conditions.

The disclosure also provides a pharmaceutical pack or kit comprising one or more containers filled with one or more squalamine polymorph pharmaceutical compositions disclosed herein. The kits may include, for instance, containers filled with an appropriate amount of a pharmaceutical composition, either as a powder, a tablet, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the composition or a derivative or salt thereof may be employed in conjunction with other therapeutic compounds.

In other aspects, a kit comprising a nasal spray device as described herein is disclosed. In one aspect, the kit may comprise one or more devices as disclosed herein, comprising a disclosed low dose squalamine polymorph composition, wherein the device is sealed within a container sufficient to protect the device from atmospheric influences. The container may be, for example, a foil, or plastic pouch, particularly a foil pouch, or heat-sealed foil pouch. Suitable containers sufficient to adequately protect the device will be readily appreciated by one of skill in the art.

In one aspect, the kit may comprise one or more devices as disclosed herein, wherein the device may be sealed within a first protective packaging, or a second protective packaging, or a third protective packaging, that protects the physical integrity of the product. One or more of the first, second, or third protective packaging may comprise a foil pouch. The kit may further comprise instructions for use of the device. In one aspect, the kit contains two or more devices.

In one aspect, the kit may comprise a device as disclosed herein, and may further comprise instructions for use. In one aspect, the instructions may comprise visual aid/pictorial and/or written directions to an administrator of the device.

VII. Combination Therapy

In the methods of the disclosure, the squalamine polymorph compositions may be administered alone or in combination with one or more other therapeutic agents. An example of an additional therapeutic agent is one known to treat the condition the composition is being administered to treat.

Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents administered first, followed by the second. The regimen selected can be administered concurrently since activation of the induced response does not require the systemic absorption of the squalamine into the bloodstream and thus eliminates concern over the likelihood systemic of drug-drug interactions between the squalamine and the administered drug.

VIII. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

The terms "pharmacologically effective amount" or "therapeutically effective amount" of a composition, aminosterol, squalamine, crystalline polymorph, crystalline hydrate, or agent, as provided herein, refer to a nontoxic but sufficient amount of the composition, aminosterol, squalamine, crystalline polymorph, crystalline hydrate, or agent, to provide the desired response. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., mass, temperature, time, and concentration, including ranges, are approximations which are varied (+) or (−) by increments of 1, 5, or 10%.

It is to be understood, although not always explicitly stated that all numerical designations are preceded by the term "about."

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

"Optional" or "optionally" means that the subsequently described circumstance may or may not occur, so that the description includes instances where the circumstance occurs and instances where it does not.

"Pharmaceutically acceptable excipient or carrier" refers to an excipient that may optionally be included in the compositions of the disclosure and that causes no significant adverse toxicological effects to the patient.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

As used in the description of the disclosure and the appended claims, the singular forms "a," "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein the term "aminosterol" refers to an amino derivative of a sterol.

The term "administering" as used herein includes prescribing for administration as well as actually administering and includes physically administering by the subject being treated or by another.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

The terms "treatment," "treating," or any variation thereof includes reducing, ameliorating, or eliminating (i) one or more specified symptoms and/or (ii) one or more symptoms or effects of a specified disorder. The terms "prevention," "preventing," or any variation thereof includes reducing, ameliorating, or eliminating the risk of developing (i) one or more specified symptoms and/or (ii) one or more symptoms or effects of a specified disorder.

"Prodrug" a prodrug is a medication or compound that, after administration, is metabolized (i.e., converted within the body) into a pharmacologically active drug, for example, squalamine. In some embodiments, a prodrug comprises a derivative of squalamine, wherein the alcohol and/or the carboxylate has been esterified.

"Optionally substituted" refers to a group selected from that group and a substituted form of that group. A "substituted" group, refers to that group substituted with a chemical substituent, for example be replacement of a C—H bond with a bond between that C and the substituent. In one embodiment, substituents are selected from, for example, $CF_3$, $OCF_3$, halo, haloaryl, $C_1$-$C_6$ alkoxy, acyl, propionyl, butyrl, acylamino, acyloxy, amino, substituted amino, aminocarbonyl, aminothiocarbonyl, aminocarbonylamino, aminothiocarbonylamino, carboxyl ester, carboxyl ester amino, (carboxyl ester)oxy, haloalkyl, aryloxy, haloalkoxy, hydroxyl, thiol, dihydroxy, aminohydroxy, carboxy, amido, sulfoxy, sulfonyl, haloaryloxy, aryl, benzyl, benzyloxy, heteroaryl, nitrile, $C_1$-$C_6$ alkyl, $C_1$-$C_6$ alkenyl, $C_1$-$C_6$ alkynyl, $C_3$-$C_6$ cycloalkyl, $C_1$-$C_6$ haloalkyl, $C_1$-$C_6$ haloalkenyl, $C_1$-$C_6$ haloalkynyl, $C_3$-$C_6$ halocycloalkyl, $C_6$-$C_{10}$ aryl, $C_3$-$C_8$ cycloalkyl, $C_2$-$C_{10}$ heterocyclyl, $C_1$-$C_{10}$ heteroaryl, —$N_3$, nitro, —$CO_2H$ or a $C_1$-$C_6$ alkyl ester thereof, or combinations thereof.

IX. Examples

Example 1: Synthetic Procedures

The phosphate salt was synthesized according to Scheme 1 below.

Scheme 1: Synthesis of ENT-01

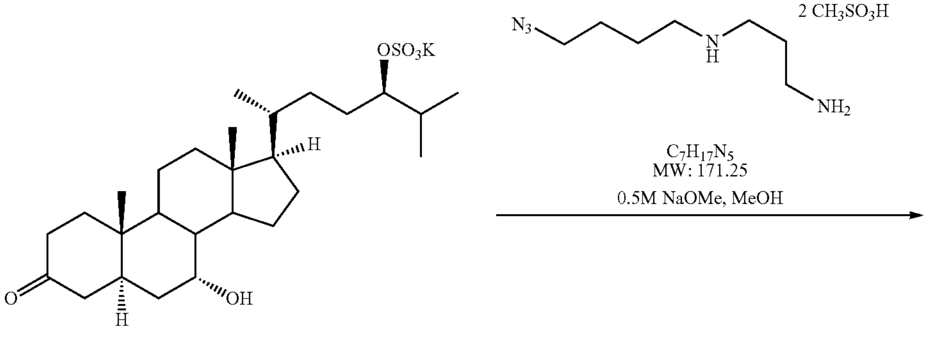

Compound 37
$C_{27}H_{45}KO_6S$
MW: 536.81

-continued
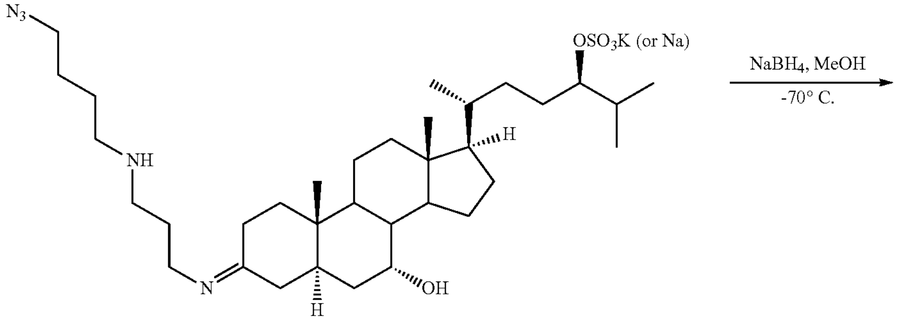
2
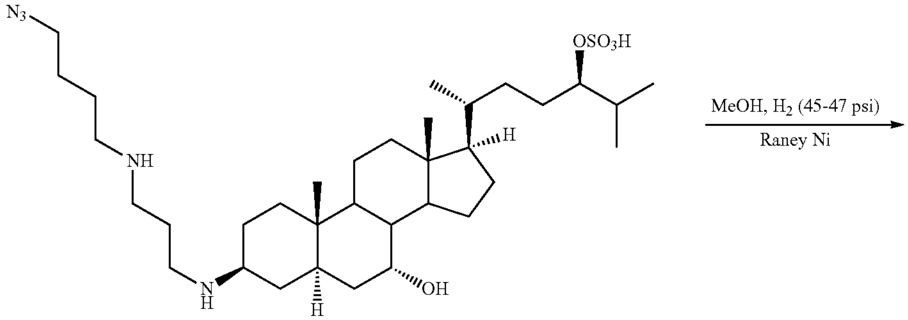
3
$C_{34}H_{63}N_5O_5S$
MWt: 653.97
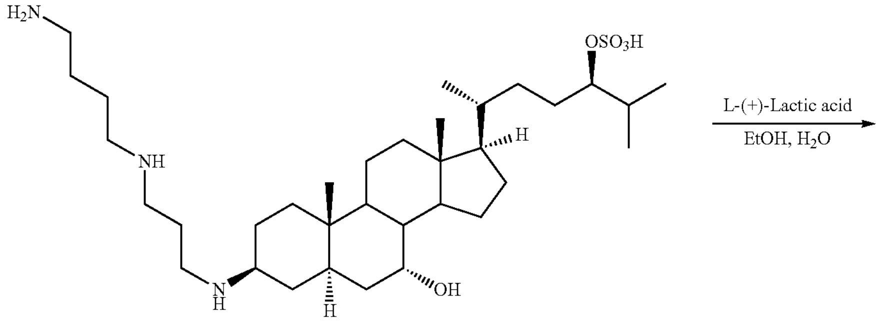
$C_{34}H_{65}N_3O_5S$
MW: 627.97
Squalamine -continued
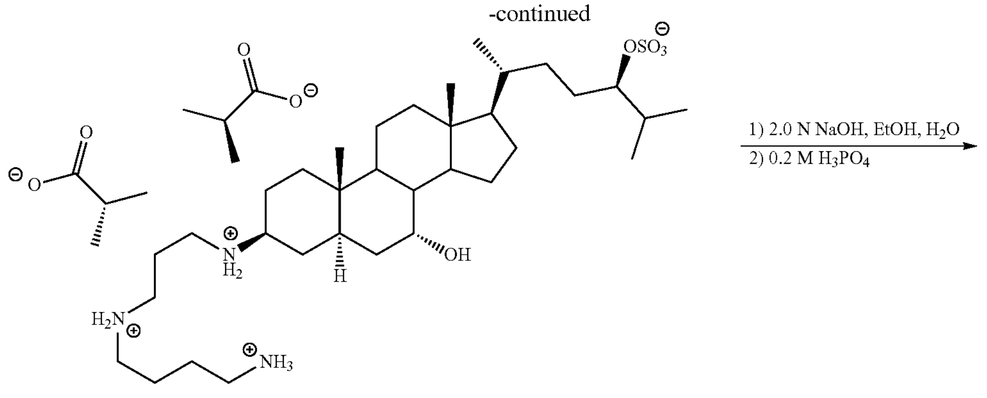
MW: 808.13
Squalamine Lactate
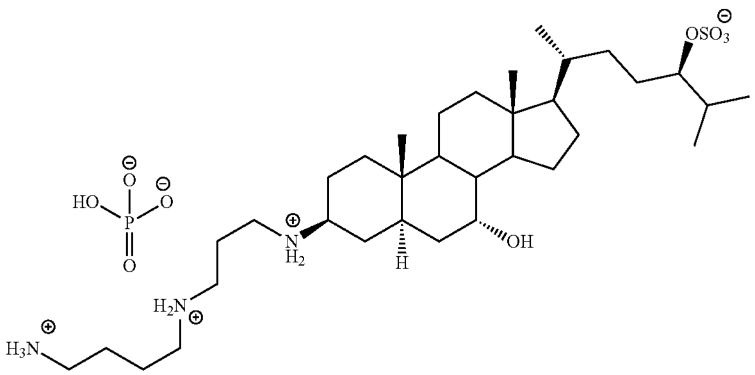
MW: 852.07
Squalamine Phosphate
ENT-01
Step 1: Synthesis of Imine 2
Imine 2 was formed from 37 according to Scheme 2 and the procedure below.
Scheme 2: Imine Formation
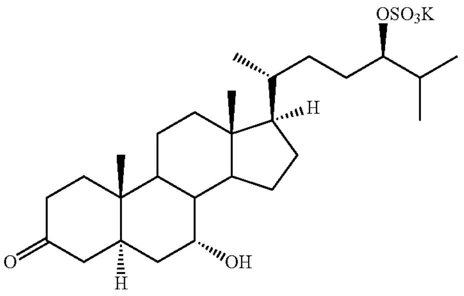
Compound 37
$C_{27}H_{45}KO_6S$
MW: 536.81
+
-continued
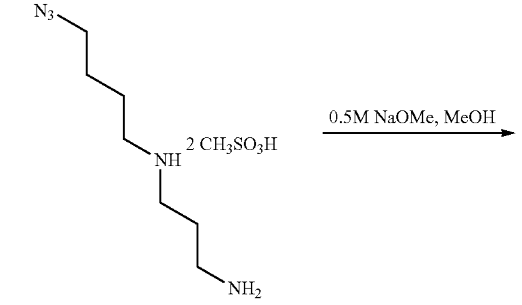
$C_7H_{17}N_5$
MW: 171.25
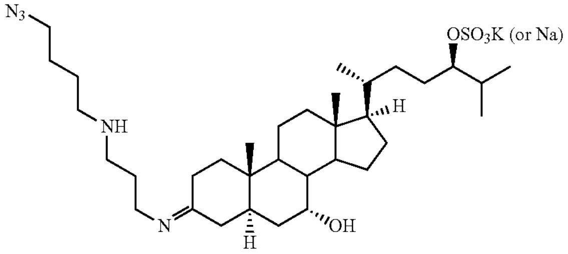
2

Procedure: A dry three-neck 22-L round bottom flask was equipped with an addition funnel, a mechanical stirrer, a thermocouple and a nitrogen inlet and charged with azidospermidine bis-mesylate (211 g, 0.58 mol) and anhydrous methanol (10 L). A solution of 5.4 M NaOMe/MeOH (215.2 mL, 1.16 mol) and methanol (2.0 L) were combined and the resulting ~0.5M NaOMe/MeOH solution was transferred into the addition funnel atop the 22-L flask. The NaOMe/MeOH solution was added to the flask over 15-20 min. A mild exotherm was observed and the reaction temperature rose from 21° C. to 25° C. The resulting clear solution was stirred at ambient temperature for 30-40 min.

Compound 37 (250 g, 0.47 mol, sourced from NCK Pharma) was added in one portion. No exotherm was observed during and after the addition. The resulting suspension was stirred for at least 6 hours at ambient temperature (an overnight stirring is acceptable). After stirring at the ambient temperature, the imine 2 solution was used as-is in the next step.

Step 2: Imine Reduction

Imine 2 was reduced according to Scheme 3 and the procedure below.

The crude imine 2 solution in MeOH, as prepared in Step 1, was cooled to −68° C. to −73° C. with dry ice-acetone bath while maintaining a positive nitrogen atmosphere in the reaction flask. $NaBH_4$ (53 g, 1.4 mol) was added in 2-3 portions. After the addition, the mixture was stirred for at least 2 hours at −68° C. to −73° C. before it was analyzed by HPLC which indicated that imine 2 had been consumed and azide 3 was formed in 81:19 (β:α) selectivity at the 3-position. The mixture was allowed to stir overnight until the batch temperature reached 10-25° C. HPLC analysis of the batch indicated no change in the HPLC profile of the reaction mixtures. Water (1.25 L) was added over 1-1.5 hours and the resulting clear solution was concentrated under reduced pressure (10 mmHg, bath at 45° C.) to give a residue. The residue was stirred (10-15 min) with 2-butanol (6 L), MTBE (1 L) and water (2 L) and layers were separated. The organic layer was stirred with MTBE (1.0 L) and water (3 L) for an additional 5-10 minutes and then layers were separated. Aqueous layers were combined and back-extracted by stirring with 2-butanol (2.0 L). Organic layers were combined and concentrated under reduced pressure (bath at 40° C.) to give ~456 g of crude azide 3 as a Scheme 3: Imine Reduction

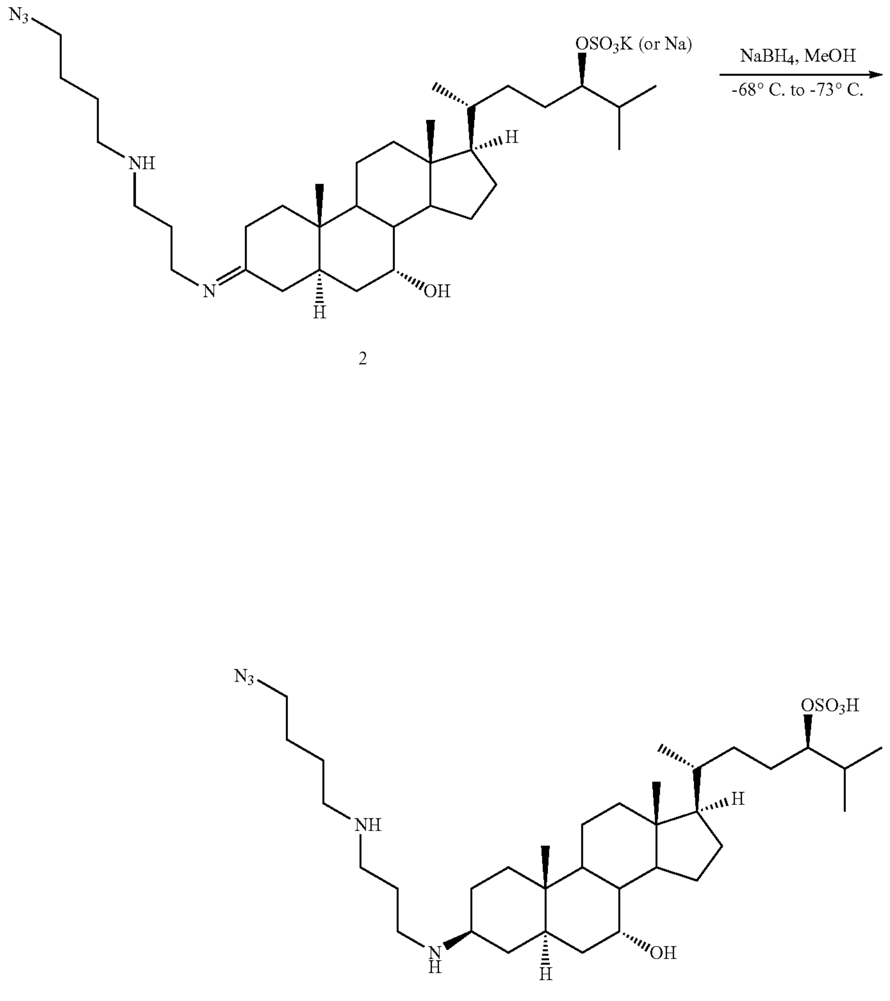

2

3
$C_{34}H_{63}N_5O_5S$
MWt: 653.97 semi-solid. The crude azide 3 was used in Step 3 without further purification. Two more runs were carried out on identical scale which provided two additional batches of crude azide 3, a 444 g batch and a 404 g batch.

Step 3: Azide Reduction to form Squalamine

Azide 3 was reduced according to Scheme 4 and the procedure below.

Scheme 4: Azide Reduction to form Squalamine

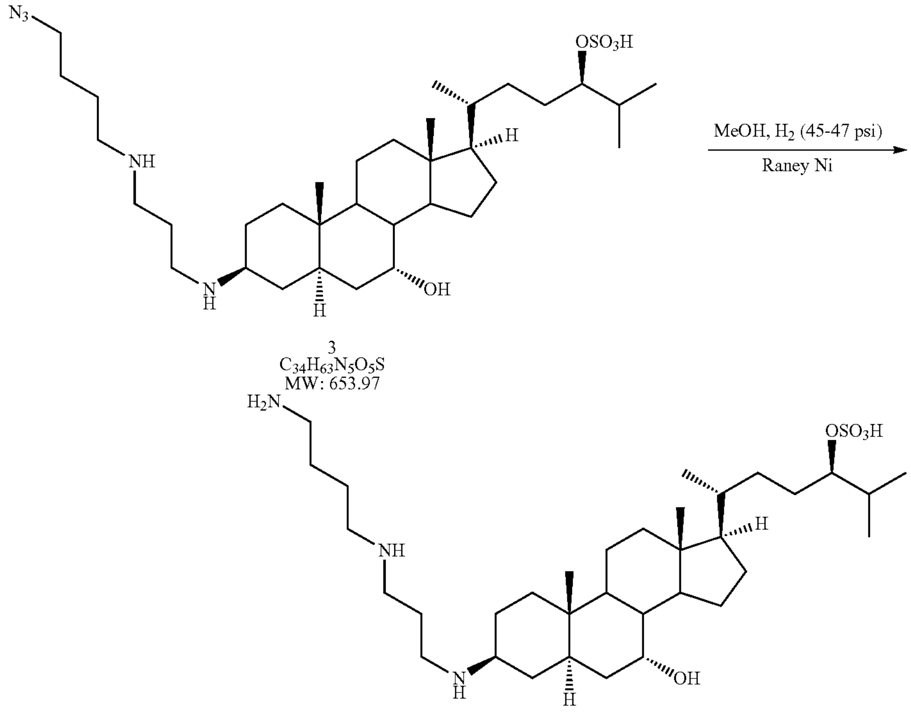

3
$C_{34}H_{63}N_5O_5S$
MW: 653.97

$C_{34}H_{65}N_3O_5S$
MW: 627.97
Squalamine

A 5 L Parr bottle was equipped with an efficient magnetic stirrer. Crude azide 3 from the previous Step 2 was transferred into the Parr bottle with the aid of MeOH (2.2 L) and then Raney® Nickel (42.4 g) was charged. The resulting mixture was stirred under 45-47 psi hydrogen pressure at ambient temperature and the progress of the reaction was monitored by HPLC. After overnight stirring, the reaction was judged complete by HPLC analysis, with complete consumption of azide 3. The mixture was carefully filtered through a 1" pad of filter agent (Solka-Floc 40) on a 600 mL Buchner filter funnel (medium porosity) aided with methanol (250-500 mL). The filter cake was rinsed with additional MeOH (300 mL). Filtrate and washes were combined (ca 3.0 L) to provide the methanol solution of squalamine. The solution was kept under nitrogen and stored at 2-8° C. until it was processed further. Six additional batches of similar squalamine/methanol solutions were prepared on identical 250 g-scale and another was prepared similarly on a 300 g scale.

Step 4: Isolation of Crude Squalamine

Three lots of methanol solutions (~9 L) of squalamine as prepared in Step 3, each from the respective 250 g-scale hydrogenation runs, were combined and filtered using Glass Microfibre Filter paper. The resulting filtrate was filtered again using a 0.45-micron nylon membrane capsule and a transfer pump and then concentrated on a rotavap at 40° C./30 torr to an adjusted weight of 3-5 kg. The resulting residue was co-distilled with 2-BuOH (15 L) under reduced pressure at 40° C. (30-40 torr) until the final weight of the resulting white slurry was ~6.0 kg. The white slurry of squalamine/2-butanol was sealed under nitrogen and stored at 2-4° C. in a cold room until it was ready to be processed in Section B below.

Another three lots of methanol solutions (~9 L) of squalamine each from the respective 250 g-scale hydrogenation runs of Step 3 were combined, twice filtered and processed as above on identical scale to provide 6.12 kg of Squalamine/2-butanol slurry. The slurry of squalamine/2-butanol was also sealed under nitrogen and stored at 2-4° C. in a cold room until it was ready to be processed for squalamine isolation as discussed below.

Another two lots of methanol solutions (~6 L) of squalamine from a 250 g-scale and another from a 300 g scale hydrogenation runs, of Step 3, were combined, twice filtered and then processed as above using 10 L of 2-butanol to provide 4.67 kg of squalamine/2-butanol slurry. The slurry of squalamine/2-butanol was also sealed under nitrogen and stored at 2-4° C. in a cold room until it was ready to be processed for squalamine isolation as follows.

The three lots of squalamine/2-butanol mixtures were transferred to a 75 L reactor equipped with a heater/chiller. The batch was stirred at 175 RPM and MTBE (49.5 L) was charged. The resulting white slurry was stirred at 20-25° C. for at least an hour after which the batch was gradually cooled to 5-7° C. and continued to stir overnight at that temperature maintaining the stir rate at 175 RPM. After overnight stirring, the batch was filtered using three 6 L Buchner funnels (medium porosity). The filtration rate was slow (12-14 h). At the end of the day, the wet cake in each of the filter funnel was placed under a nitrogen tent and vacuum was pulled until no filtrates were observed from the three filter funnels (48 h). Each cake in the filter funnel was broken into smaller pieces using spatula and then washed with MTBE (2x2 L). The MTBE washed wet cakes on three filter funnels were placed under separate nitrogen tents and dried overnight by pulling vacuum. After drying overnight, the cakes were transferred on to drying trays and dried in a vacuum oven at 40° C. until a constant weight was achieved. A total of 2313.8 g of crude squalamine (96.5% crude yield) was obtained as white solid which was found to be 62.7% pure by HPLC analysis and contained 10.38% of 3α isomer. Crude squalamine was obtained in a mixture of two diastereomers (86:14, 3β:3α).

Step 5: Preparation of Squalamine Lactate

Squalamine lactate was prepared according to Scheme 4 and the procedure below.

an in-line 0.45μ filter capsule attached. Additional, anhydrous 200 proof ethanol (4.7 L) was charged into the reactor.

Stirring was adjusted to 270-280 RPM and batch temperature to 20-25° C. A solution of L-(+)-lactic acid (1,291.5 g, 14.34 mol) and water (1.8 L) was prepared. A total of 65% of the lactic acid solution (1.85 L) transferred into the addition funnel atop the reactor and was added over 10 minutes to the stirring solution at 20-25° C. resulting in a cloudy solution. Squalamine lactate seed crystals (3.4 g) were added. The batch was stirred at for 30 minutes after which the remaining lactic acid solution (940 mL) was added over 10-15 minutes. The batch was aged for 1 hour at 20-25° C. and then heated to 35° C. over 40-60 minutes. After stirring for 15 minutes at 35° C., the batch was programmed to cool to 8° C. over a 10 hour period and then held at 8° C. for at least 4 hours. The resulting white slurry was filtered using 12 L and a 6-L medium porosity filter funnels. Filtration of the product was slow and continued overnight under a nitrogen tent. The cake was washed with cold (0-5° C.) anhydrous 200 proof ethanol (20 L). The filtered cake was dried over two days on the filter funnel Scheme 4: Squalamine Lactate Formation

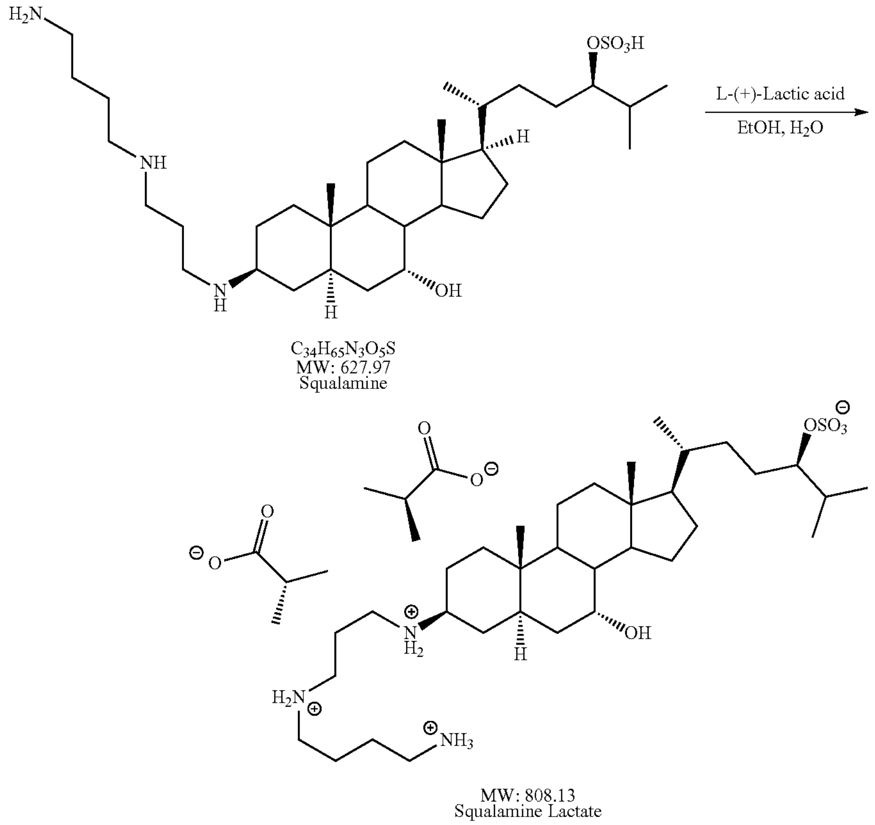

$C_{34}H_{65}N_3O_5S$
MW: 627.97
Squalamine

MW: 808.13
Squalamine Lactate

A 75-L reactor was equipped with an addition funnel, a mechanical stirrer, a thermocouple and a nitrogen inlet. Crude squalamine (2,250 g, 3.58 mol as-is from Step 4) and anhydrous 200 proof ethanol (38 L) were charged. The mixture was stirred and heated to 35-40° C. for 1 hour. The resulting cloudy solution was filtered using two 150 mm glass microfibre filter (GF/F) papers which provided a clear solution. The filtration rate was slow and required ~1.5 hours to complete the filtration. The clear solution was transferred back into the reactor using a pump and a transfer line with under a nitrogen tent by pulling vacuum on the cake and then dried in a vacuum oven at 40° C. with a nitrogen bleed until at constant weight, providing 1,493 g (overall 49.6% yield from Compound 37) of squalamine lactate as white solid. The isolated product was found to be >98% pure by HPLC analysis and contained 0.48% of the 3α-isomer.

The squalamine lactate was then purified as follows. A 75-L reactor was equipped with an addition funnel, a mechanical stirrer, a thermocouple and a nitrogen inlet. The squalamine lactate (1.475 kg, 1.82 mol) and anhydrous 200 proof ethanol (14.75 L) were charged. The mixture was stirred and heated to 50° C. for 1.5 h. The resulting solution, nearly clear, was filtered using a pump and a transfer line with an in-line attached 0.2$\mu$ filter device (40 min). The filtered clear solution was returned to the reactor. The temperature of the solution was adjusted to 40° C. and squalamine lactate seed crystals (2.17 g) were added. The rate of the stirring was adjusted to 200 RPM. The resulting thin slurry was aged at 40° C. for 15 minutes and then programmed to cool to 5-8° C. over a 4 hour period after which it was allowed to stir overnight at that temperature. The resulting white slurry was filtered using a 12-L medium porosity filter funnel over 18 hours. The reactor was rinsed with the mother liquors to retrieve the residual product. The rinse was then transferred onto the cake on the filter funnel. The filtered cake was dried overnight on the filter funnel under a nitrogen tent by pulling vacuum on it. The semi-wet cake was washed with cold (5-8° C.) anhydrous ethanol (2 L) and then again dried overnight on the filter funnel under a nitrogen tent by pulling vacuum on it. The filter cake was broken into smaller pieces and further dried in a vacuum oven at 40° C. with a nitrogen bleed to provide 1.4 kg (95.05% yield) of purified squalamine lactate as white solid. The purified product was found to be 97.5% pure by HPLC analysis and contained 0.21% of the 3$\alpha$-isomer.

Step 6: Formation of ENT-01

ENT-01 was formed according to Scheme 5 and the procedure below.

A 75-L reactor was equipped with an addition funnel, a mechanical stirrer, a thermocouple and a nitrogen inlet. Purified squalamine lactate from Step 5 (1.375 kg, 1.7 mol), water (27.5 L) and anhydrous 200 proof ethanol (27.5 L) were charged. The mixture was stirred at 20±5° C. and the stirring rate was adjusted to 200-225 RPM. 2N NaOH solution (1.865 L, 1.63 mol) was added over 10-15 minutes at 25±5° C. The resulting clear solution was heated to 35° C. The 0.2 M phosphoric acid solution was added in three portions. The first portion of 0.2 M phosphoric acid (3.67 L, 46% of the total amount) was added over 10-15 minutes at 35-37° C. After the addition was over, the batch was heated to 45° C. over a period of 30-40 min. The second portion of 0.2 M phosphoric acid (0.92 L) was added at 45° C. at a slower rate, over 30 min, resulting in a cloudy solution (additional phosphoric acid solution was added until a cloudy solution (saturation point) was obtained). Squalamine phosphate (ENT-01) seed crystals (2.3 g) were added after which the addition of the remaining final portion of 0.2 M phosphoric acid was resumed and was added over 2 hours at 45° C. After the addition was over, the batch was cooled to 20° C. over 2 hours and allowed to stir overnight at that temperature resulting in a white slurry.

The batch was filtered using 12-L and 6-L medium porosity filter funnels. The filtration rate of the product was slightly faster than observed before but it still took 8 hours to complete the filtration. The filtration was continued overnight under a nitrogen tent by pulling vacuum on the Scheme 5: ENT-01 Formation

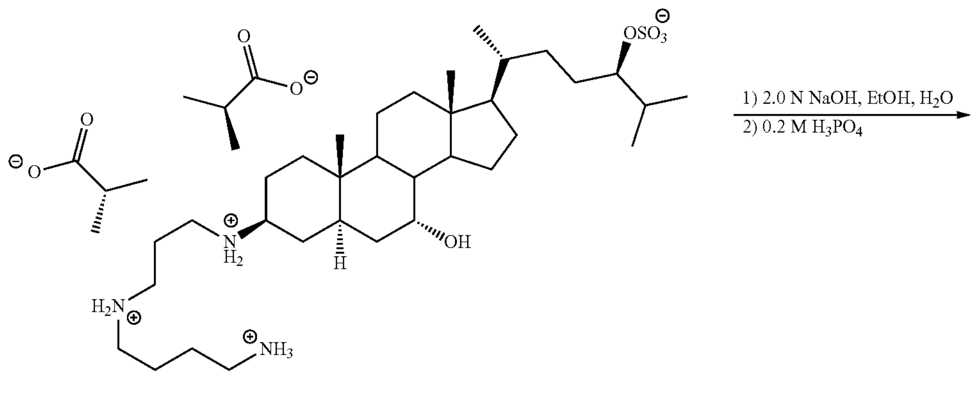

MW: 808.13
Squalamine Lactate

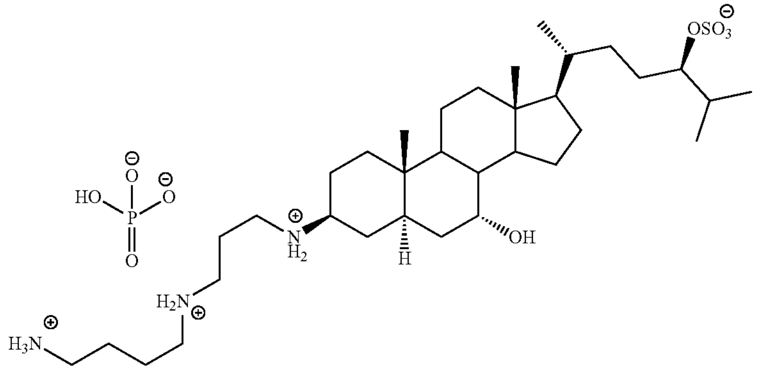

MW: 852.07
Squalamine Phosphate
ENT-01 wet filter cake until no more filtrates were observed. The filter cake was washed with acetone (2×12.5 L) and the cake was dried on the filter funnels for 6 hours then in a vacuum oven at room temperature with a nitrogen bleed to provide 1.051 kg (72.6% yield) of squalamine phosphate (ENT-01) as white solid. The isolated product was found to be 98.4% pure by HPLC.

Example 2: X-Ray Powder Diffraction Analysis of Polymorphic Forms

Figure 2:
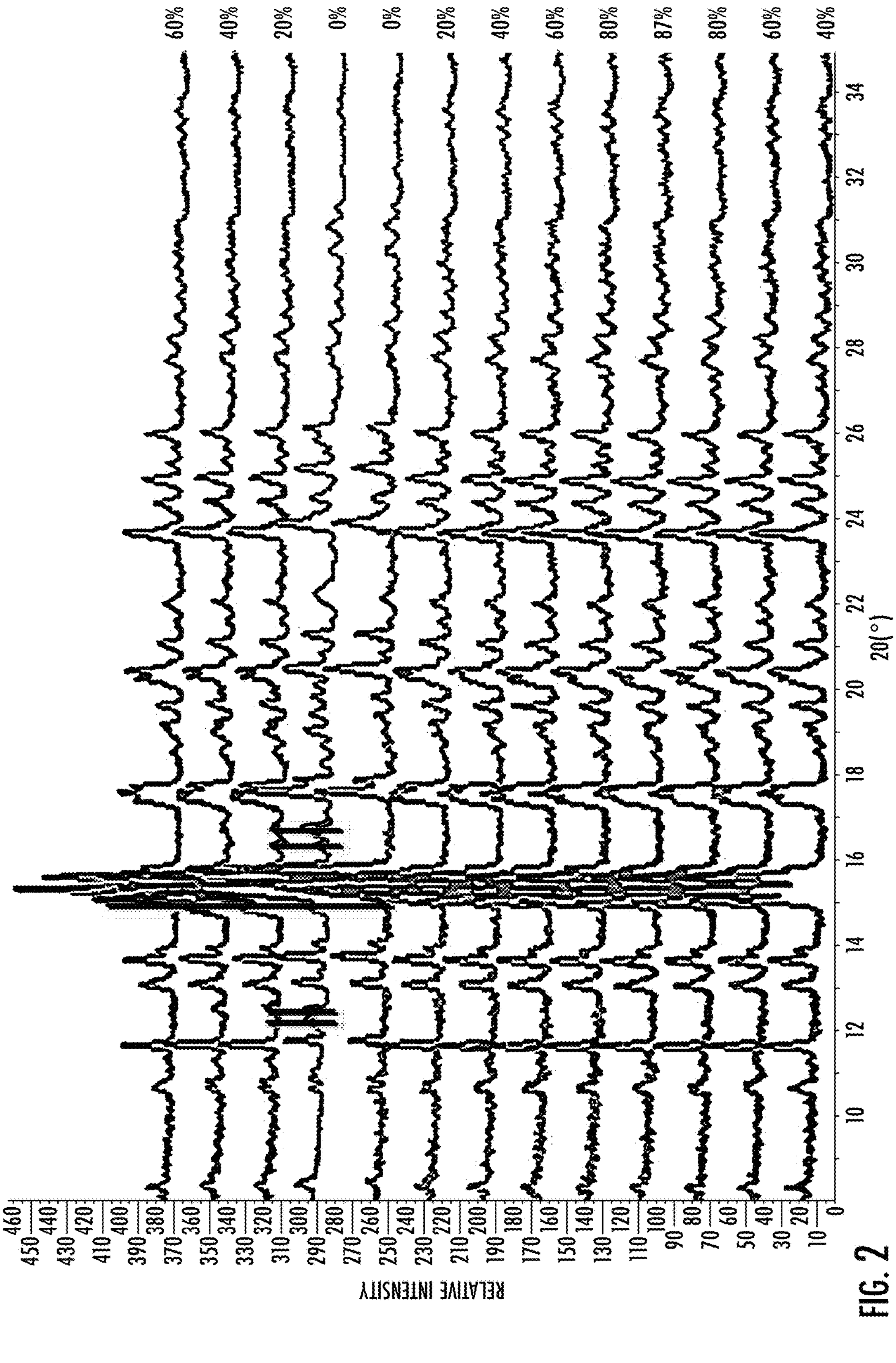
FIG. 2: Overlay of XRPD diffractograms collected during the exposure of Form A1 to variable RH levels (40→87→0→60%) at 30° C.
Figure 5:
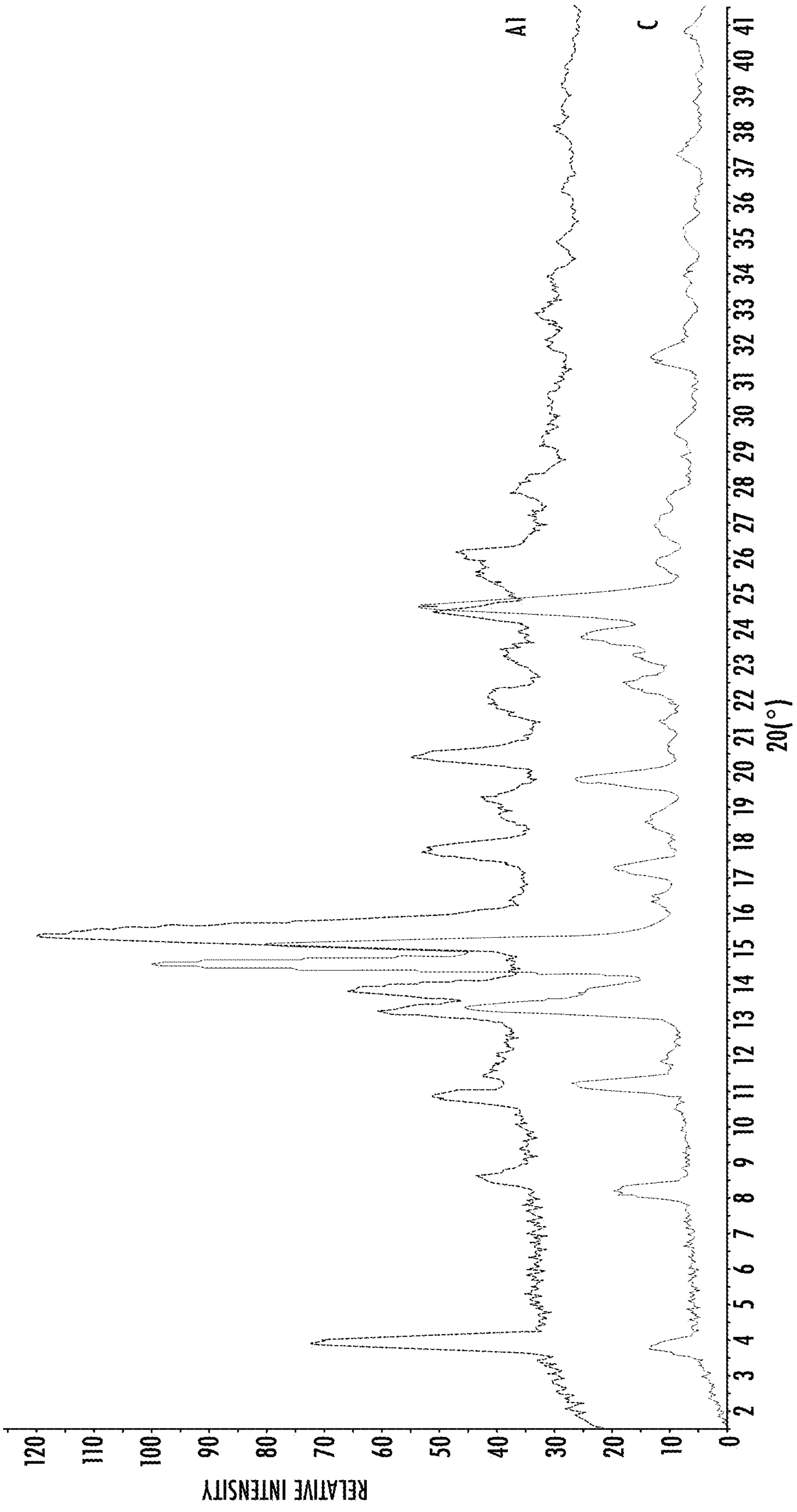
FIG. 5: Overlay of HT-XRPD patterns of Form C and the precursor material Form A1.

Polymorphic Form A1 of ENT-01 was characterized by High Throughput X-ray Powder Diffraction (HT-XRPD), High Resolution X-ray Powder Diffraction (HR-XRPD), and Variable Humidity X-ray Powder Diffraction. Both HT-XRPD and HR-XRPD spectra of Form A1 are overlaid in FIG. 1. VH-XRPD spectra for Form A1 are shown in FIG. 2. HT-XRPD spectra for Form C (overlayed with Form A1) is shown in FIG. 5.

I. High Throughput X-Ray Powder Diffraction

HT-XRPD patterns were obtained using the Crystallics T2 high-throughput XRPD set-up. The plates were mounted on a Bruker General Area Detector Diffraction System (GADDS) equipped with a VÅNTEC-500 gas area detector corrected for intensity and geometric variations. The calibration of the measurement accuracy (peaks position) was performed using NIST SRM1976 standard (Corundum).

Data collection was carried out at room temperature using monochromatic Cu Kα radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 s for each frame. No background subtraction or curve smoothing was applied to the XRPD patterns. The carrier material used during HT-XRPD analysis was transparent to X-rays and contributed only slightly to the background.

II. High Resolution X-Ray Powder Diffraction

The HR-XRPD data were collected on D8 Advance diffractometer using Cu $K_{\alpha 1}$ radiation (1.54056 Å) with germanium monochromator at RT. Diffraction data were collected in the 2θ range 2-41.5° 2θ. Detector scan on solid state LynxEye detector was performed using 0.016° per step with 15 sec/step scan speed. The samples were measured in 8 mm long glass capillary with 1 mm outer diameter. Experimental details and crystallographic data for forms A1 and C are reported in Table 1 below.

TABLE 1

Experimental details and crystallographic data for squalamine forms A1 and C

| EXP. ID<br>Polymorph | A1 | C |
|---|---|---|
| Empirical formula | $C_{34}H_{68}N_3O_5S^{2+}$ $HPO_4^{2-}$•4 $H_2O$ | $C_{34}H_{68}N_3O_5S^{2+}$ $HPO_4^{2-}$•5.5 $H_2O$ |
| Formula weight | 798.019 | 825.019 |
| T [K] | 296 | 296 |
| λ [Å] | 1.54056 | 1.54056 |
| Crystal system | Monoclinic | Monoclinic |
| Space group | P $2_1$ | P $2_1$ |
| a [Å] | 8.1708(3) | 7.924(2) |
| b [Å] | 11.6131(4) | 12.155(3) |
| c [Å] | 22.4252(12) | 23.257(5) |
| β [°] | 90.763(3) | 92.611(3) |
| V [$Å^3$] | 2127.7(15) | 2237.7(10) |
| Z (Z') | 2 | 2 |

TABLE 1-continued

Experimental details and crystallographic data for squalamine forms A1 and C

| EXP. ID<br>Polymorph | A1 | C |
|---|---|---|
| $D_c$ [g/cm$^3$] | 1.246 | 1.224 |
| Cap. Size [mm$^2$] | 0.5 × 8 | 1 × 8 |
| 2θ range [°] | 0.016 | 0.016 |
| No of steps | 2489 | 2489 |
| Time per step [s] | 15 | 10 |
| 2θ Step size [°] | 2-41.5 | 2-41.5 |
| Rexp | 2.05 | 1.96 |
| $R_{wp}$ | 2.95 | 2.51 |
| $R_p$ | 2.12 | 1.83 |
| GOF | 1.44 | 1.28 |
| $R_{Brag}$ | 0.89 | 0.09 |
| Impurities, other forms [%] | BDL | BDL |

The HR-XRPD diffractogram of Form A1 was indexed. Form A1 crystallized in the non-centrosymmetric monoclinic space group $P2_1$. The determined unit cell parameters were a=8.1708(3), b=11.6131(4), c=22.4252(12) Å, β=90.763(3)°, V=2127.7(15) $Å^3$, Z=2, $D_{calc}$=1.246 g/cm$^3$.

Cell parameters were obtained using LSI-Index indexing program. The atoms positions were placed into the cell obtained in the RT and used for Rietveld refinement. The following criteria of fit were used:

$Y_{o,m}$ and $Y_{c,m}$ are the observed and calculated data, respectively at data point m, M the number of data points, P the number of parameters, $w_m$ the weighting given to 8 data point m which for counting statistics is given by $w_m=1/\sigma(Y_{o,m})^2$ where $\sigma(Y_{o,m})$ is the error in $Y_{o,m}$.

$$R_{exp} = \sqrt{\frac{M-P}{\sum w_m Y_{o,m}^2}};\ R_{up} = \sqrt{\frac{\sum w_m (Y_{o,m} - Y_{c,m})^2}{\sum w_m Y_{o,m}^2}};$$

$$R_p = \sqrt{\frac{\sum |Y_{o,m} - Y_{c,m}|}{\sum Y_{o,m}}}$$

$$GOF = chi^2 = \frac{R_{up}}{R_{exp}} = \sqrt{\frac{\sum w_m (Y_{o,m} - Y_{c,m})^2}{M-P}}$$

III. Variable Humidity X-Ray Powder Diffraction

The powder data were collected on D8 Advance diffractometer using Cu $K_{\alpha 1}$ radiation (1.54056 Å) with germanium monochromator at 30° C. using the SYCOS H-HOT hot humid chamber produced by Ansyco GmbH. The data were collected in the Bragg-Brentano geometry (locked coupled) from 8 to 35° 2θ on the flat sample holder (without rotation) on solid state LynxEye detector with 0.018° per step with 1 sec/step scan speed. After reaching demanded humidity the sample was relaxed for 5 minutes before measurement. The sample was optionally measured with 2 seconds per step and in the last measurement at RH 0% the relaxation time was elongated to 30 min.

Variable Humidity XRPD (VH-XRPD) measurements were performed on Forms A1 and C to investigate the in-situ phase changes induced by exposure to variable RH levels. Diffractograms of Form A1 were collected at 30° C. with a RH profile of 40→87→0→60% (FIG. 2). Initially, the pattern of Form A1 was distinguished at 40% RH. By increasing the RH level up to 87%, no changes in the XRPD pattern were detected. Furthermore, no changes were observed by lowering the RH from 87% down to 20%.

When the RH level was decreased to 0%, no significant changes were initially noticed (only small shifts were identified which could indicate that the crystal cell shrinks due to the partial water lost). However, upon incubation at 0% RH for a longer period of time, additional diffraction peaks in the powder pattern of Form A1 were identified which could be attributed to a new solid form.

By increasing the RH level to 20%, the diffractogram of Form A1 was observed, although a small phase contamination was still detected. The contamination was observed also at 40% RH, whereas at 60% RH it completely disappeared.

In conclusion, Form A1 proved to be stable in the range 40→87→20% RH. Below 20% RH, a novel XRPD pattern was detected, indicating that by exposure to low RH levels Form A1 released water converting to a lower-degree hydrate (or anhydrous) phase. This novel phase reversibly converted to Form A1 when exposed to RH levels above 20%.

Diffractograms of Form C were collected at 30° C. with a RH profile of 40→85→0→60% (FIG. 24). No changes were detected in the XRPD pattern of Form C from 40 up to 85% RH. Similarly, the pattern of Form C was recorded without any significant change from 85% down to 40% RH.

Figure 12:
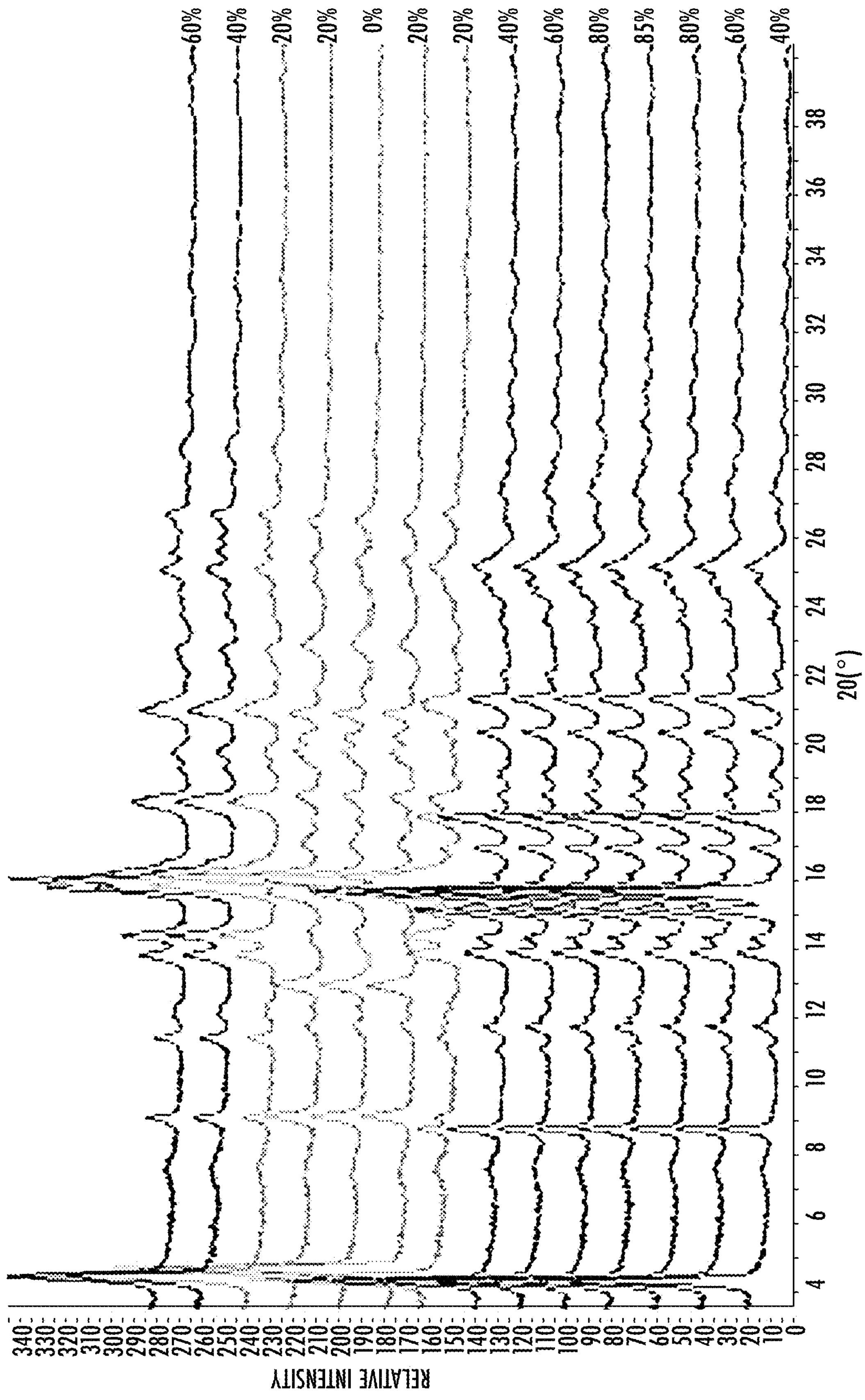
FIG. 12: Overlay of XRPD diffractograms collected during the exposure of Form C to variable RH levels (40→85→0→60%) at 30° C.

In contrast, at 20% RH the appearance of a novel XRPD pattern was observed (FIG. 12, 20% and 0% lines). Upon incubation at 20% RH for a longer period of time, full conversion of Form C to the novel crystalline phase was achieved. This novel phase was physically stable at 0% RH. By increasing the RH level to 20%, this novel pattern was still detected. However, by keeping the solid at 20% RH for longer time, the appearance of Form A1 was observed. The full conversion to Form A1 was achieved at 40% RH. Form A1 remained physically stable also at 60% RH.

TABLE 2

Peak Table for Form A1 (HR-XRPD measurement of SM).

| No | 2θ [°] | D value [Å] | Intensity [%] |
|---|---|---|---|
| 1 | 3.96 | 22.32 | 89 |
| 2 | 8.59 | 10.29 | 12 |
| 3 | 10.84 | 8.15 | 16 |
| 4 | 11.49 | 7.70 | 4 |
| 5 | 13.27 | 6.67 | 29 |
| 6 | 13.89 | 6.37 | 43 |
| 7 | 15.27 | 5.80 | 76 |
| 8 | 15.52 | 5.70 | 100 |
| 9 | 15.78 | 5.61 | 46 |
| 10 | 15.98 | 5.54 | 11 |
| 11 | 17.72 | 5.00 | 26 |
| 12 | 17.91 | 4.95 | 19 |
| 13 | 18.76 | 4.73 | 8 |
| 14 | 19.18 | 4.62 | 7 |
| 15 | 19.37 | 4.58 | 10 |
| 16 | 20.44 | 4.34 | 30 |
| 17 | 20.58 | 4.31 | 22 |
| 18 | 20.80 | 4.27 | 6 |
| 19 | 21.24 | 4.18 | 5 |
| 20 | 21.76 | 4.08 | 9 |
| 21 | 22.18 | 4.01 | 12 |
| 22 | 23.09 | 3.85 | 6 |
| 23 | 23.35 | 3.81 | 6 |
| 24 | 23.83 | 3.73 | 6 |
| 25 | 24.02 | 3.70 | 5 |
| 26 | 24.53 | 3.63 | 22 |
| 27 | 25.10 | 3.55 | 10 |
| 28 | 25.48 | 3.49 | 12 |
| 29 | 25.81 | 3.45 | 9 |

TABLE 2-continued

Peak Table for Form A1 (HR-XRPD measurement of SM).

| No | 2θ [°] | D value [Å] | Intensity [%] |
|---|---|---|---|
| 30 | 26.14 | 3.41 | 22 |
| 31 | 26.67 | 3.34 | 3 |

TABLE 3

Peak Table for Form B1 (HR-XRPD measurement of sample recovered after stability test at 80° C. for 24 hours).

| No | 2θ [°] | D value [Å] | Intensity [%] |
|---|---|---|---|
| 1 | 4.19 | 21.07 | 31 |
| 2 | 8.61 | 10.26 | 29 |
| 3 | 11.28 | 7.84 | 8 |
| 4 | 11.75 | 7.53 | 12 |
| 5 | 12.41 | 7.13 | 33 |
| 6 | 13.59 | 6.51 | 19 |
| 7 | 13.95 | 6.34 | 19 |
| 8 | 15.05 | 5.88 | 76 |
| 9 | 15.47 | 5.73 | 100 |
| 10 | 16.48 | 5.38 | 12 |
| 11 | 17.25 | 5.14 | 11 |
| 12 | 17.88 | 4.96 | 15 |
| 13 | 18.88 | 4.70 | 28 |
| 14 | 19.19 | 4.62 | 15 |
| 15 | 19.64 | 4.52 | 15 |
| 16 | 20.27 | 4.38 | 43 |
| 17 | 21.07 | 4.21 | 12 |
| 18 | 22.18 | 4.01 | 12 |
| 19 | 22.65 | 3.92 | 10 |
| 20 | 23.07 | 3.85 | 9 |
| 21 | 23.56 | 3.77 | 9 |
| 22 | 24.00 | 3.71 | 17 |
| 23 | 24.23 | 3.67 | 12 |
| 24 | 24.70 | 3.60 | 15 |
| 25 | 25.40 | 3.50 | 12 |
| 26 | 25.94 | 3.43 | 11 |
| 27 | 26.93 | 3.31 | 6 |
| 28 | 27.39 | 3.25 | 8 |
| 29 | 28.01 | 3.18 | 9 |

For B1, the unit cell belonged to the monoclinic space group $P2_1$. The unit cell parameters were a=7.8531(9), b=11.772(2), c=21.223(4) Å, β=94.890(8)°, V=1955.0(9) $Å^3$, Z=2, $D_{calc}$=1.266 g/$cm^3$.

TABLE 4

Peak Table for Form C (HR-XRPD measurement of Exp. ID SLP34).

| No | 2θ [°] | D value [Å] | Intensity [%] |
|---|---|---|---|
| 1 | 3.82 | 23.09 | 86 |
| 2 | 8.22 | 10.74 | 27 |
| 3 | 10.55 | 8.38 | 8 |
| 4 | 11.19 | 7.90 | 17 |
| 5 | 11.45 | 7.73 | 8 |
| 6 | 11.99 | 7.38 | 8 |
| 7 | 13.35 | 6.63 | 28 |
| 8 | 13.77 | 6.43 | 19 |
| 9 | 14.05 | 6.30 | 10 |
| 10 | 14.59 | 6.07 | 61 |
| 11 | 15.14 | 5.85 | 100 |
| 12 | 15.63 | 5.66 | 12 |
| 13 | 16.39 | 5.40 | 20 |
| 14 | 16.89 | 5.24 | 10 |
| 15 | 17.28 | 5.13 | 40 |

TABLE 4-continued

| Peak Table for Form C (HR-XRPD measurement of Exp. ID SLP34). | | | |
|---|---|---|---|
| No | 2θ [°] | D value [Å] | Intensity [%] |
| 16 | 17.94 | 4.94 | 13 |
| 17 | 18.57 | 4.77 | 12 |
| 18 | 18.92 | 4.69 | 9 |
| 19 | 19.39 | 4.57 | 9 |
| 20 | 19.75 | 4.49 | 27 |
| 21 | 20.71 | 4.28 | 26 |
| 22 | 21.16 | 4.20 | 10 |
| 23 | 21.45 | 4.14 | 14 |
| 24 | 21.99 | 4.04 | 10 |
| 25 | 22.49 | 3.95 | 12 |
| 26 | 22.98 | 3.87 | 12 |
| 27 | 23.26 | 3.82 | 14 |
| 28 | 23.79 | 3.74 | 18 |
| 29 | 24.11 | 3.69 | 20 |
| 30 | 24.59 | 3.62 | 30 |
| 31 | 24.91 | 3.57 | 18 |

TABLE 5

| Peak Table for Form A2 (HT-XRPD measurement of Exp. ID SLP4.2). | | | |
|---|---|---|---|
| No | 2θ [°] | D value [Å] | Intensity [%] |
| 1 | 4.07 | 21.69 | 70 |
| 2 | 8.65 | 10.22 | 17 |
| 3 | 10.89 | 8.12 | 14 |
| 4 | 11.43 | 7.73 | 9 |
| 5 | 11.76 | 7.52 | 14 |
| 6 | 13.29 | 6.66 | 25 |
| 7 | 13.82 | 6.40 | 27 |
| 8 | 15.38 | 5.76 | 100 |
| 9 | 17.61 | 5.03 | 24 |
| 10 | 19.13 | 4.64 | 13 |
| 11 | 20.33 | 4.36 | 26 |
| 12 | 22.09 | 4.02 | 10 |
| 1 | 4.07 | 21.69 | 70 |
| 13 | 23.47 | 3.79 | 9 |
| 14 | 24.49 | 3.63 | 15 |
| 15 | 25.68 | 3.47 | 12 |
| 16 | 26.08 | 3.41 | 15 |
| 17 | 27.97 | 3.19 | 7 |
| 18 | 32.91 | 2.72 | 6 |

TABLE 6

| Peak Table for Form B2 (HT-XRPD measurement of Exp. ID SLP21.2). | | | |
|---|---|---|---|
| No | 2θ [°] | D value [Å] | Intensity [%] |
| 1 | 4.14 | 21.31 | 60 |
| 2 | 8.70 | 10.15 | 27 |
| 3 | 10.99 | 8.05 | 9 |
| 4 | 11.85 | 7.46 | 20 |
| 5 | 12.54 | 7.05 | 20 |
| 6 | 13.64 | 6.49 | 16 |
| 7 | 15.22 | 5.82 | 100 |
| 8 | 17.49 | 5.07 | 26 |
| 9 | 19.15 | 4.63 | 16 |
| 10 | 20.15 | 4.40 | 33 |
| 11 | 22.70 | 3.91 | 8 |
| 12 | 23.46 | 3.79 | 8 |
| 13 | 24.89 | 3.57 | 11 |
| 14 | 25.79 | 3.45 | 8 |
| 15 | 33.08 | 2.71 | 5 |

TABLE 7

| Peak Table for Form D (HT-XRPD measurement of solid recovered after cDSC of SM). | | | |
|---|---|---|---|
| No | 2θ [°] | d value [Å] | Intensity [%] |
| 1 | 4.10 | 21.55 | 80 |
| 2 | 7.85 | 11.25 | 51 |
| 3 | 9.74 | 9.07 | 37 |
| 4 | 12.79 | 6.91 | 62 |
| 5 | 13.86 | 6.38 | 46 |
| 6 | 14.60 | 6.06 | 95 |
| 7 | 15.14 | 5.84 | 89 |
| 8 | 16.42 | 5.39 | 100 |
| 9 | 17.22 | 5.14 | 44 |
| 10 | 19.06 | 4.65 | 44 |
| 11 | 20.34 | 4.36 | 60 |
| 12 | 20.94 | 4.24 | 44 |
| 13 | 22.26 | 3.99 | 41 |
| 14 | 24.46 | 3.63 | 38 |

TABLE 8

| Peak Table for Form E (HT-XRPD measurement of Exp. ID TCP8.1). | | | |
|---|---|---|---|
| No | 2θ [°] | d value [Å] | Intensity [%] |
| 1 | 6.50 | 13.60 | 15 |
| 2 | 9.28 | 9.52 | 26 |
| 3 | 10.43 | 8.47 | 66 |
| 4 | 13.91 | 6.36 | 35 |
| 5 | 14.57 | 6.07 | 22 |
| 6 | 15.39 | 5.75 | 6 |
| 7 | 17.01 | 5.21 | 31 |
| 8 | 17.90 | 4.95 | 20 |
| 9 | 19.91 | 4.46 | 18 |
| 10 | 21.55 | 4.12 | 32 |
| 11 | 22.48 | 3.95 | 26 |
| 12 | 23.14 | 3.84 | 28 |

TABLE 9

| Peak Table for Form F (HT-XRPD measurement of Exp. ID TCP8.2). | | | |
|---|---|---|---|
| No | 2θ [°] | d value [Å] | Intensity [%] |
| 1 | 4.42 | 19.97 | 100 |
| 2 | 5.13 | 17.21 | 29 |
| 3 | 6.56 | 13.46 | 26 |
| 4 | 8.80 | 10.04 | 18 |
| 5 | 9.99 | 8.85 | 16 |
| 6 | 11.49 | 7.70 | 25 |
| 7 | 13.97 | 6.33 | 31 |
| 8 | 15.28 | 5.79 | 30 |
| 9 | 15.86 | 5.58 | 22 |
| 10 | 16.77 | 5.28 | 11 |
| 11 | 17.96 | 4.93 | 11 |
| 12 | 20.14 | 4.41 | 9 |
| 13 | 22.35 | 3.97 | 11 |
| 14 | 27.66 | 3.22 | 10 |
| 15 | 28.10 | 3.17 | 15 |

Example 3: TGA/SDTA and TGMS Analysis

Mass loss due to solvent or water loss from the crystals was determined by Thermogravimetric Analysis and. Simultaneous Difference Thermal Analysis (TGA/SDTA). Monitoring the sample weight, during heating in a TGA/DSC 3+ STARe system (Mettler-Toledo GmbH, Switzerland), resulted in a weight vs. temperature curve. The TGA/DSC 3+ was calibrated for temperature with samples of indium and aluminum. Samples (circa 2 mg) were weighed into 100 μL aluminum crucibles and sealed. The seals were pin-holed, and the crucibles heated in the TGA from 25 to 300° C. at a heating rate of 10° C. min-1. Dry $N_2$ gas was used for purging.

The gases coming from the TGA samples were analyzed by a mass spectrometer Omnistar GSD 301 T2 (Pfeiffer Vacuum GmbH, Germany). The latter is a quadrupole mass spectrometer, which analyzes masses in the temperature range of 0-200 amu.

Figure 3A:
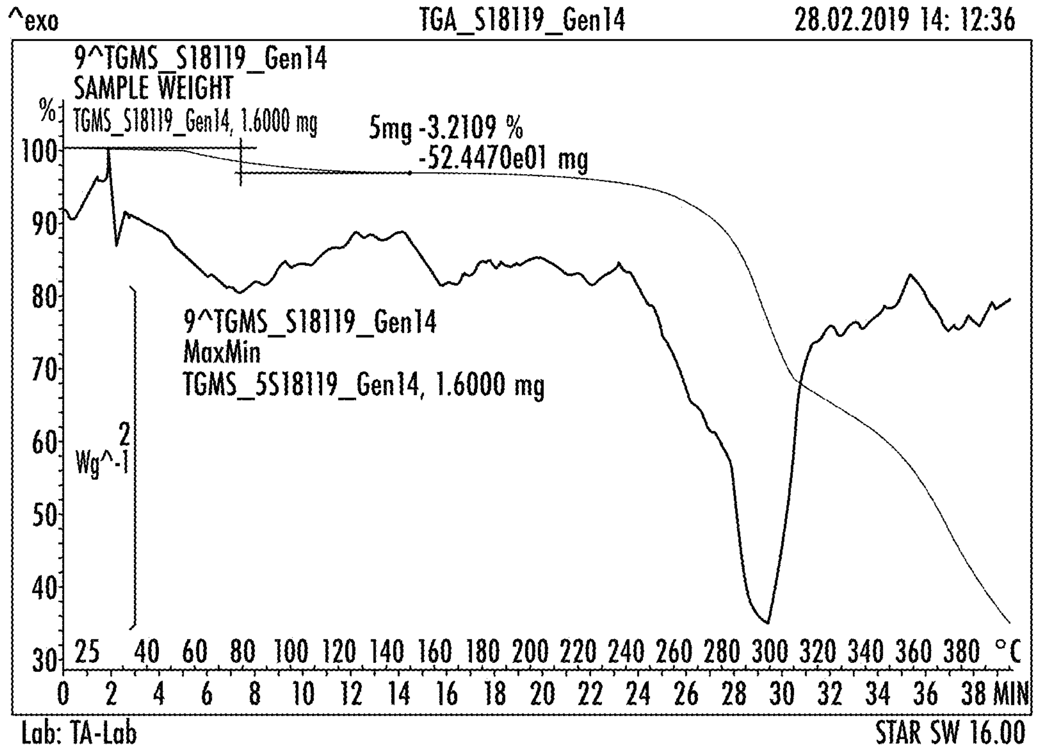
FIG. 3: Thermogravimetric Analysis and Simultaneous Difference Thermal Analysis (TGA/SDTA) and thermogravimetric analysis-mass spectrometry (TGMS) analysis (heating rate of 10° C./min) of ENT-01 Form A1. A mass loss of 8.3% was recorded in the range 40-220° C. that could be attributed to 4 water molecules per API molecule. Thermal decomposition started above 280° C.
Figure 3B:
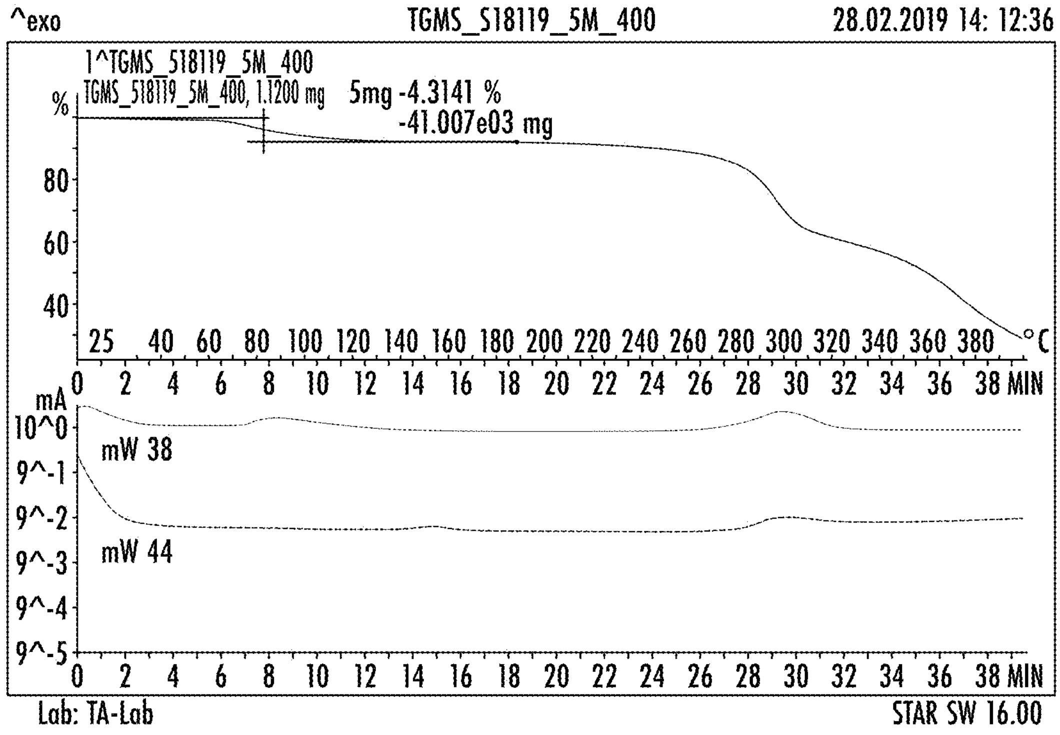

The Thermogravimetric Analysis/Mass Spectrometry (TGA-MS) analysis of ENT-01 (FIG. 3) showed a mass loss of 8.3% between 4° and 220° C., corresponding approximately to 4 water molecules per API molecule for Form A1. The thermal decomposition of the compound started above 300° C. The Karl Fisher analysis performed on the starting material showed a water content of 10.6%, corresponding to 4.6 water molecules per API molecule.

The TGMS analysis of the scaled-up Form C (FIG. 17) showed a mass loss of 12.6% in the range 40-200° C., attributed to 5.8 water molecules per API molecule. The Karl Fisher analysis of Form C showed a water content of 13.5% (w/w) corresponding to 6.3 water molecules per API molecule.

The TGMS analysis of Form A2 showed a mass loss of 2.7% recorded in the range 40-200° C. that could be attributed to water and ethanol. Thermal decomposition started above 260° C. The TGA/TGMS analysis of Form B2 showed a mass loss of 3.2% in the range 40-180° C., corresponding to 1.3 water molecules per API molecule. The TGA/TGMS analysis of Form D (FIG. 43) showed a mass loss of 3.9% in the range 40-160° C., corresponding to 1.3 water molecules per API molecule.

The TGA/MS analysis was performed both on the ambient-dried Form E and the vacuum-dried Form F. In the TGA curve of Form E a mass loss of 13.4% was recorded in the range 40-220° C. that could be attributed to both water and methanol, according to the MS signal. In the TGA curve of Form F a mass loss of 2.65 was detected in the range 40-180° C. that could be still attributed to both water and methanol, according to the MS signal.

Example 4: DSC Analysis

Melting properties were obtained from DSC thermograms, recorded with a heat flux DSC822e instrument (Mettler-Toledo GmbH, Switzerland). The DSC822e was calibrated for temperature and enthalpy with a small piece of indium (melting point at 156.6° C.; $\Delta H_f$=28.45 $J \cdot g^{-1}$). Samples were sealed in standard 40 μl aluminum pans, pin-holed or hermetically sealed and heated in the DSC from −20° C. to 300° C., at a heating rate of 2° C./$min^{-1}$, 5° C./$min^{-1}$, 10° C./$min^{-1}$ or 20° C./$min^{-1}$. Dry $N_2$ gas, at a flow rate of 50 mL/$min^{-1}$ was used to purge the DSC equipment during the measurement.

Figure 4:
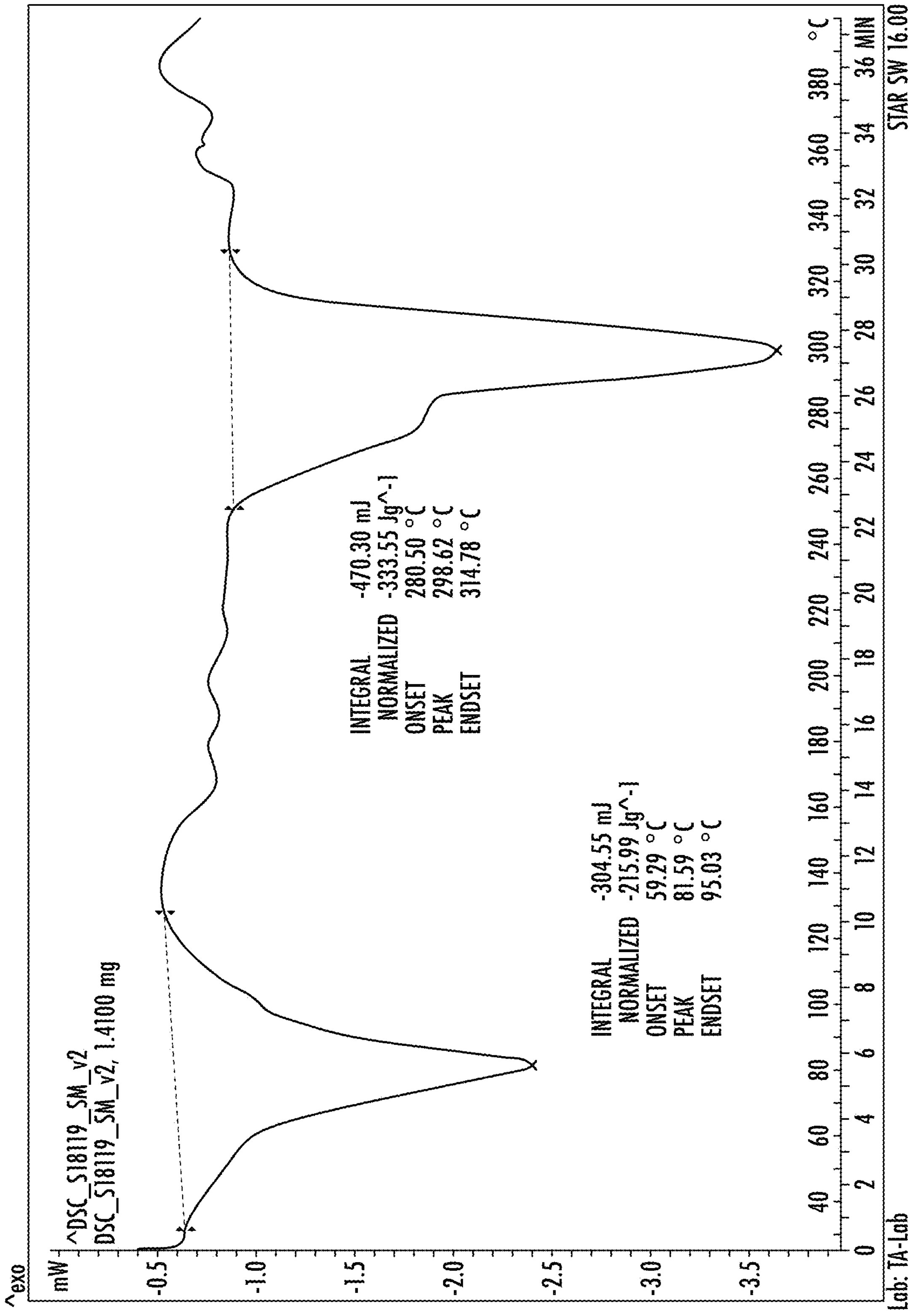
FIG. 4: Differential scanning calorimetry (DSC) analysis (heating rate of 10° C./min) of ENT-01 Form A1.

The DSC trace of Form A1 (FIG. 4) showed a broad endothermic event between 4° and 120° C., due to the water loss. Small endothermic events were also detected between 14° and 220° C. A broad endothermic event was recorded between 26° and 320° C. that could correspond to the thermal decomposition.

Figure 9:
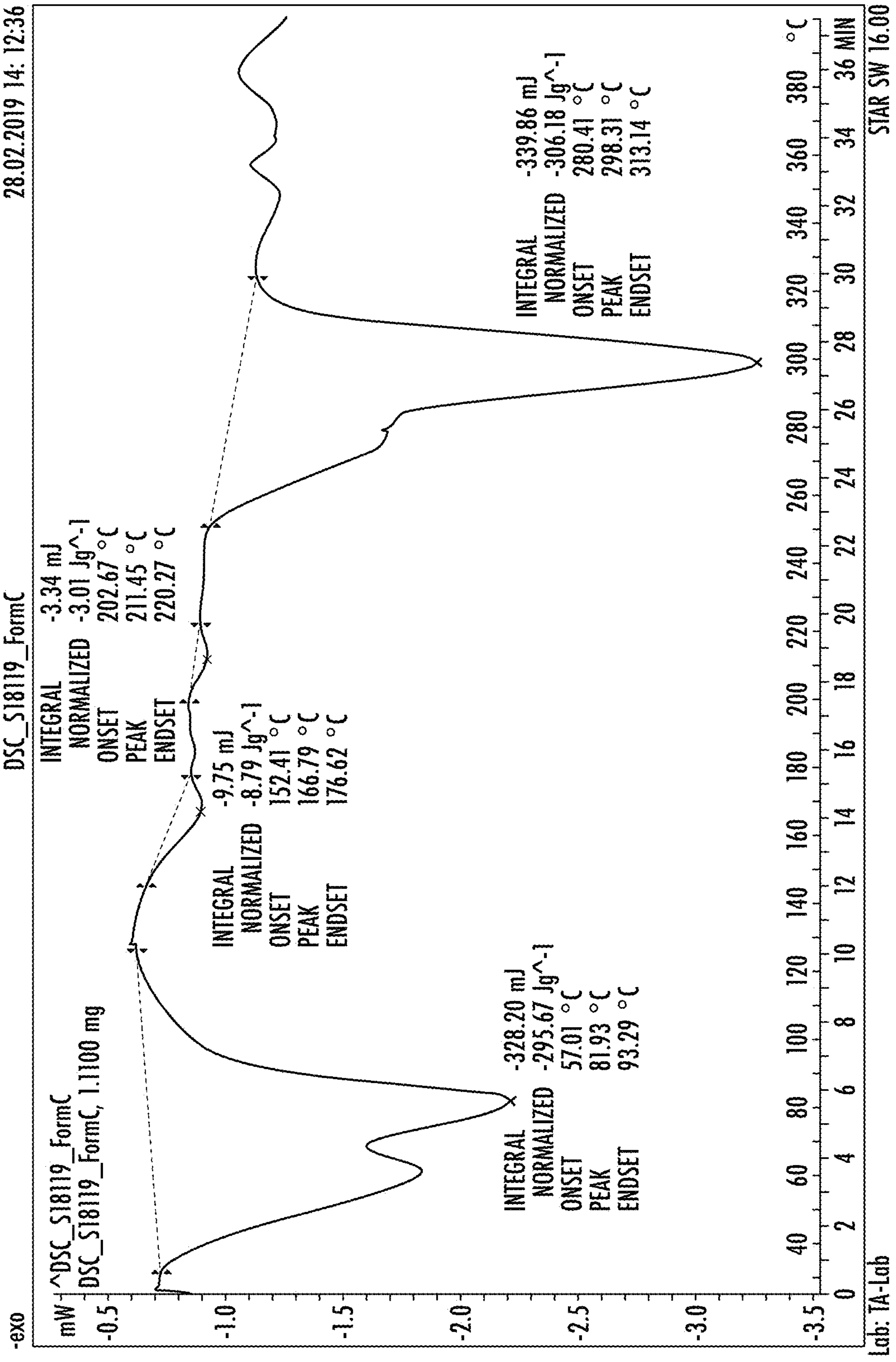
FIG. 9: DSC analysis (heating rate of 10° C./min) of Form C.

The DSC curve of Form C (FIG. 9) showed two overlapping broad events between 4° and 120° C. that could be associated to the water loss. Small broad endothermic events were also recorded between 14° and 220° C. The broad endothermic event observed between 25° and 330° C. that could correspond to the thermal decomposition.

The DSC analysis of Form A2 showed broad endothermic events between 4° and 110° C. that could be due to water/solvent loss. Other endothermic events were observed which nature was not further investigated. The broad endothermic event between 24° and 320° C. could be associated to melting and decomposition.

The TGA/TGMS analysis of Form B1 obtained by dehydration of Form A1, showed a mass loss of 3.3% in the range 40-140° C., corresponding to 1.5 water molecules per API molecule. The DSC curve of Form B2 showed a broad endothermic event in the range 40-110° C. that could be due to the water loss. Other broad endothermic events were detected between 15° and 220° C. The broad endothermic event recorded at 300° C. could be associated with the thermal decomposition.

The DSC curve of the vacuum-dried Form F showed a broad endothermic event in the range 40-80° C. that could be due to the water/solvent loss. A broad endothermic event was detected at 195.3° C. that could be due to melting. The broad endothermic event recorded between 24° and 320° C. could be associated with the thermal decomposition.

Example 5: Hydrate Screen and the Formation of Polymorph Form C

Figure 6:
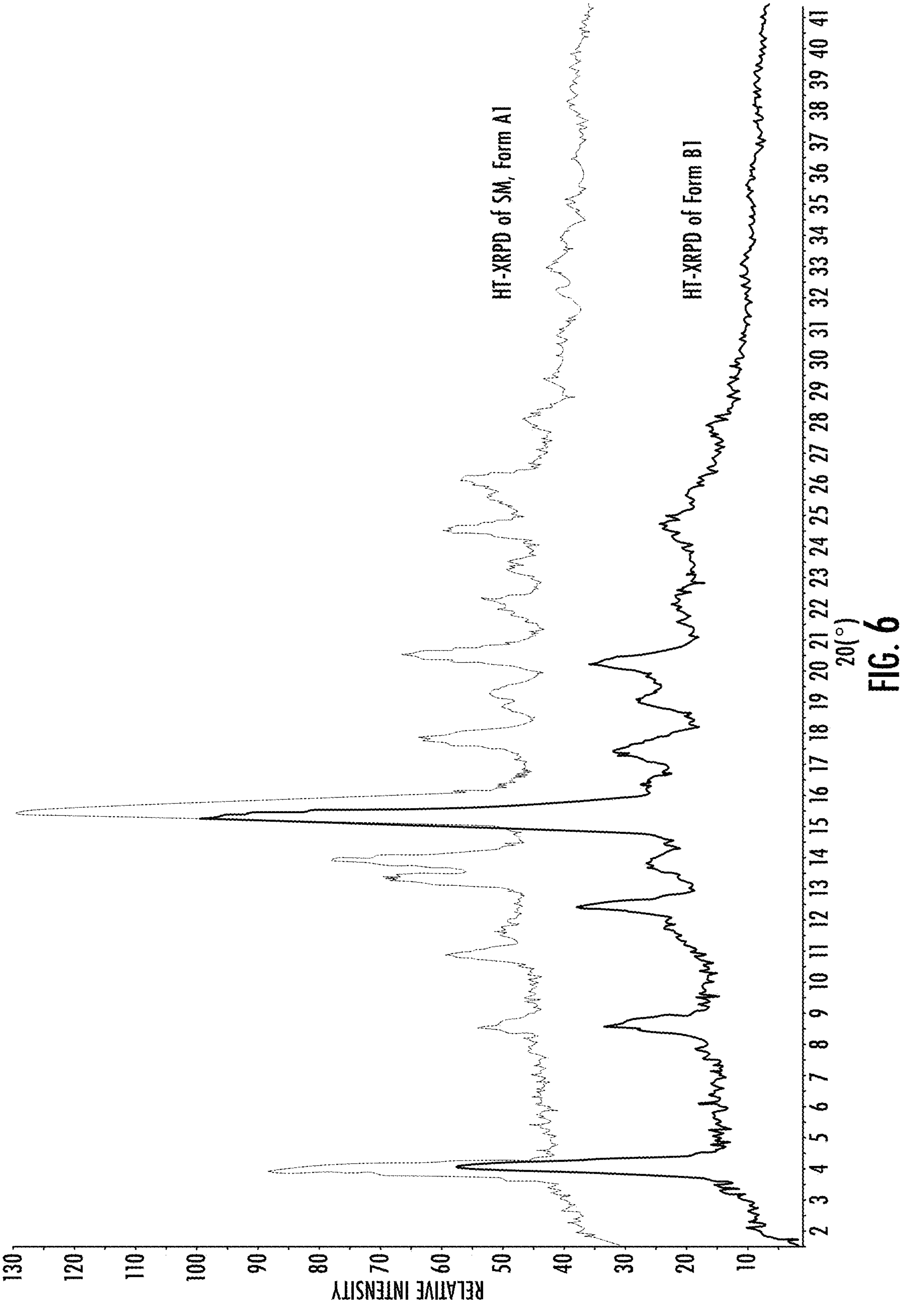
FIG. 6: Overlay of HT-XRPD patterns (blue and red line, respectively) of the received batch of ENT-01 (Form A1) and the material recovered after drying under vacuum at 50° C. overnight.

A polymorphic Form B1 was obtained by drying Form A1 under vacuum at 50° C. overnight. The recovered solid was analyzed by HT-XRPD, HR-XRPD and TGMS. The novel XRPD pattern of the dehydrated material was classified as Form B1 (FIG. 6). The XRPD peaks for Form B1 are tabulated in Table 3 above.

Form B1 was used as the starting material for the hydrate screen. The aim of the hydrate screen was to evaluate the crystallization dependency of ENT-01 on the water activity of the solvent system ($a_w$) and temperature.

For this hydrate screen, the lower-hydrate Form B1 was suspended in ethanol/water mixtures with $a_w$ ranging from 0 to 1. The solvent equilibration experiments were carried out at three different temperatures: 5, 25 and 50° C. The solid phase composition was evaluated after 1-week incubation. The liquid phases were analyzed by Karl Fisher to estimate the water content (and calculate the $a_w$). The experimental details are reported in section § 5.1.3, on page 29.

Figure 7:
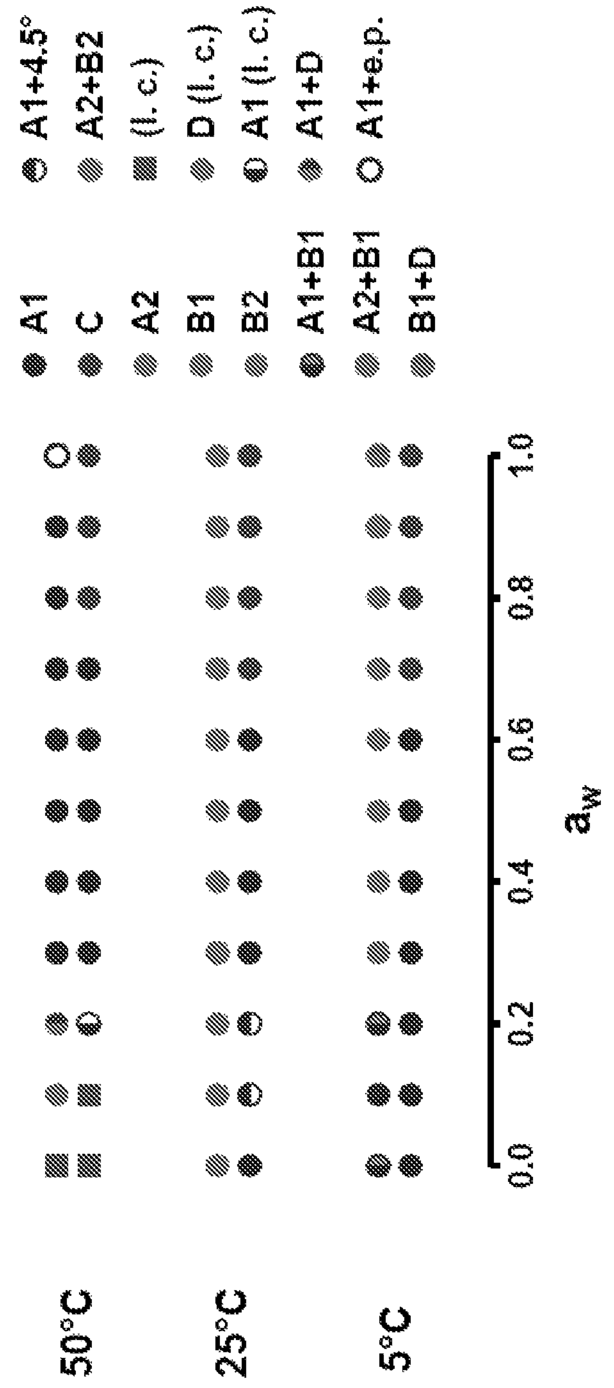
FIG. 7: Results of the hydrate screen experiments performed in ethanol/water mixtures at 5, 25 and 50° C. Solids were analyzed by HT-XRPD, both dried at ambient conditions and under vacuum (5 mbar/50° C./overnight for the experiments at 5 and 25° C. and 5 mbar/25° C./overnight for the experiments at 50° C.). The bottom rows indicate the solid phase composition of the ambient-dried solids, whereas the top rows indicate the forms identified in the vacuum-dried solid. "A1+4.5°" is used for a solid that resembled the powder pattern of Form A1 with an extra peak at 4.5° 2θ. "A1+e.p" is used for a Form A1 with extra peaks not belonging to any of the identified phases.
Figure 8A:
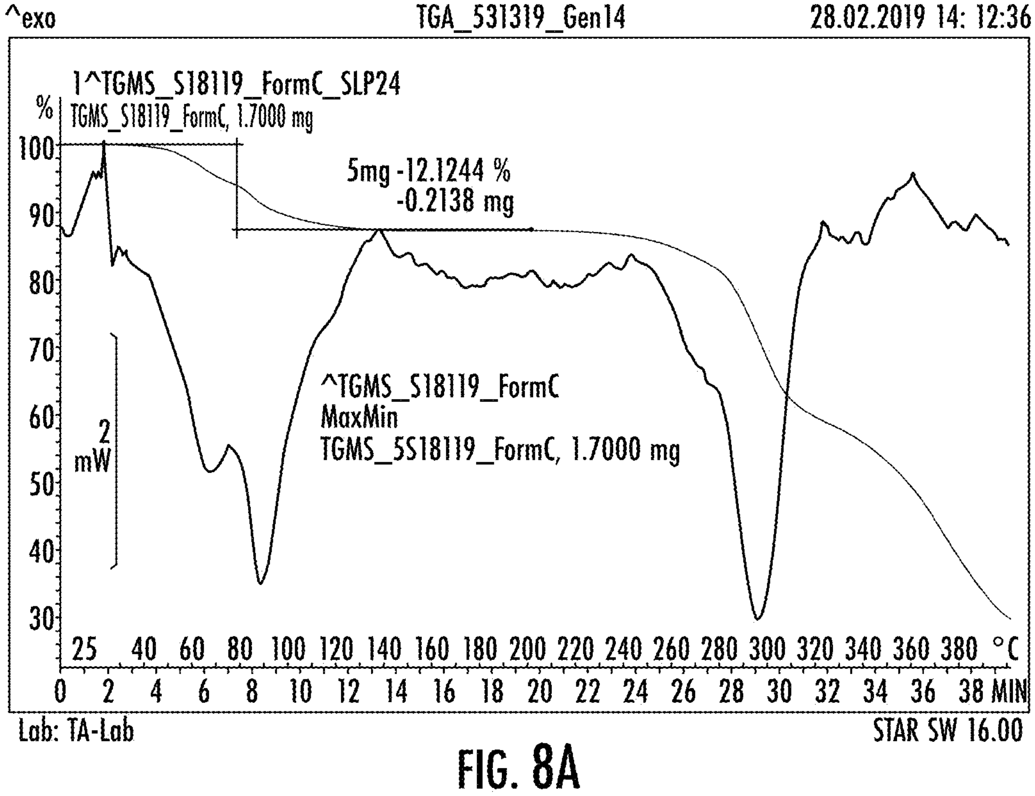
FIG. 8: TGA/SDTA (FIG. 8A) and TGMS (FIG. 8B) analysis (heating rate of 10° C./min) of Form C. A mass loss of 12.6% was recorded in the range 40-200° C., attributed to 5.8 water molecules per API molecule. Thermal decomposition started above 280° C.
Figure 8B:
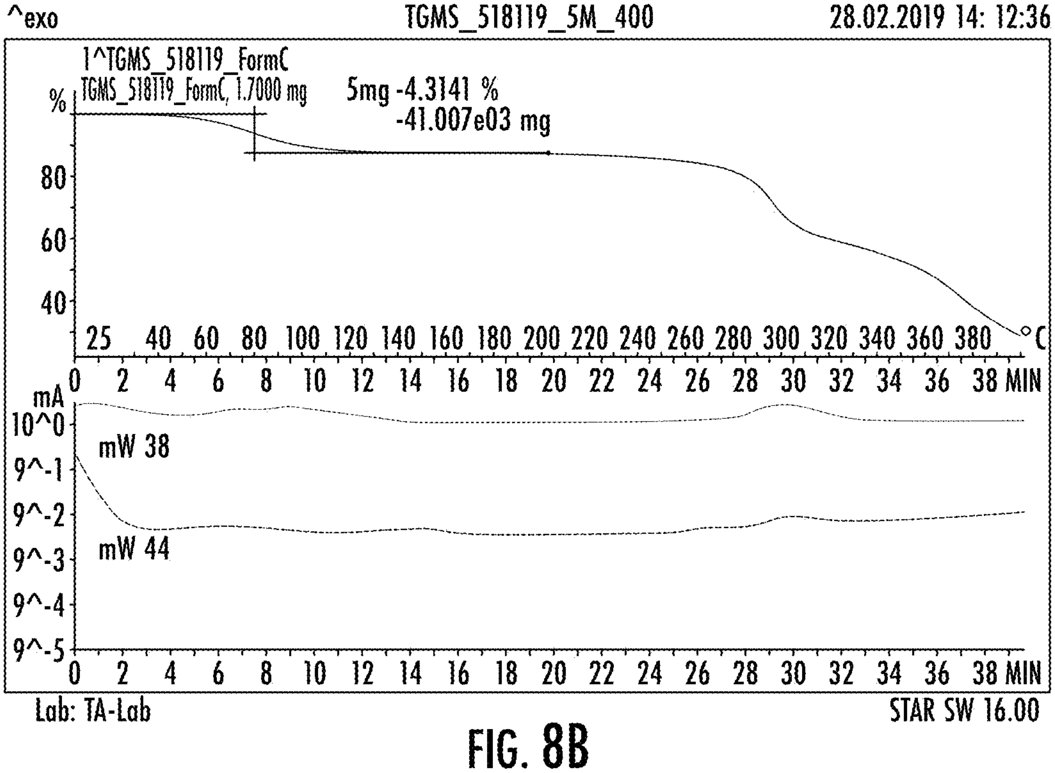

The results of the hydrate screen are shown in FIG. 7. In the ambient-dried solids, Form A1 was identified in the range of $a_w$ 0-0.6 both at 5 and 25° C. A small contamination from an unknown crystalline phase was detected at 25° C. in the solids recovered from the solvent mixtures with $a_w$ 0.1 and 0.2. A novel XRPD pattern was identified in the ambient-dried solids recovered from the experiments performed in solvent mixtures with aw in the range 0.7 and 1. This pattern was designated as Form C (FIG. 5). The TGMS analysis of Form C revealed that this crystalline phase contained approximately 6 water molecules per API molecule.

In the vacuum-dried solids, a novel pattern very similar to Form A1 but with shifted peaks was identified. This phase was designated Form A2 (see Table 2) and characterized by HT-XRPD. The TGMS characterization of Form A2 revealed that this phase contained approximately 3% of solvent (both water and ethanol), being most likely a mixed hydrate/solvate. Form A2 was identified in several vacuum-dried solids recovered from the hydrate screen experiments. The experimental conditions where Form A2 was identified are reported in Table 5. Form A2 was physically unstable upon exposure to AAC (40° C./75% RH) for 2 days, since in most of the cases it converted to Form A1.

TABLE 10

| EXPERIMENTAL CONDITIONS LEADING TO THE CRYSTALLIZATION OF FORM A2 | | | | | | |
|---|---|---|---|---|---|---|
| | | | HT-XRPD | | | |
| EXP. ID | CRYSTALIZATION METHOD | SOLVENT | AMBIENT-DRIED SOLID | AMBIENT-DRIED SOLID (AAC) | VACUUM-DRIED SOLID | VACUUM-DRIED SOLID (AAC) |
| SLP2 | EQUILIBRATION AT 5° C. | ETHANOL/WATER 98.6/1.4 | A1 | A1 | B1 | A2 |
| SLP3 | EQUILIBRATION AT 5° C. | ETHANOL/WATER 96.9/3.1 | A1 | A2 | A1 + B1 | A1 |
| SLP4 | EQUILIBRATION AT 5° C. | ETHANOL/WATER 94.7/5.3 | A1 | A1 | A2 | A1 |
| SLP5 | EQUILIBRATION AT 5° C. | ETHANOL/WATER 91.8/8.2 | A1 | A1 | A2 | A1 |
| SLP6 | EQUILIBRATION AT 5° C. | ETHANOL/WATER 88/12 | A1 | A1 | A2 | A1 |
| SLP7 | EQUILIBRATION AT 5° C. | ETHANOL/WATER 83/17 | A1 | A1 | A2 | A1 |
| SLP13 | EQUILIBRATION AT 25° C. | ETHANOL/WATER 98.6/1.4 | A2 | A2 | B1 | A2 |
| SLP15 | EQUILIBRATION AT 25° C. | ETHANOL/WATER 94.7/5.3 | A1 | A1 | A2 + B2 | A2 |

However, often mixtures of crystalline phases were identified in the vacuum-dried solids. In some cases, the hydrates Forms A1 and C converted to the mixed hydrate/solvate Form A2, or to the low-degree hydrates B1 and B2 (see Tables 3 and 6). Such conversions indicated that the drying conditions were critical for the crystalline phase stability.

In the experiments performed at 50° C., only poorly crystalline materials were recovered in the ambient-dried solids with $a_w$<0.2. Form A1 was isolated in the ambient-dried solids recovered from the ethanol/water mixtures with 0.2<$a_w$<0.7. Form C crystallized in solvent mixtures with aw>0.7. In this set of experiments the drying under vacuum was performed at 25° C. and not at 50° C. By applying such a drying condition, the structure of Form A1 was physically stable. On the contrary, Form C converted to Form A1. The appearance of Form D (see Table 7) was noticed after vacuum-drying the solids obtained from solvent systems with $a_w$ 0.1-0.2.

Form B1 was initially generated by drying form A1 under vacuum at 50° C. overnight. However, Form B1 was also identified in some vacuum-dried solids recovered from the hydrate screen experiments. The experimental conditions where Form B1 was identified are reported in Table 11. Form B1 was physically unstable upon exposure to AAC (40° C./75% RH) for 2 days, since it converted to Form A1.

TABLE 11

| EXPERIMENTAL CONDITIONS LEADING TO THE CRYSTALLIZATION OF FORM B1. | | | | | | |
|---|---|---|---|---|---|---|
| | | | HT-XRPD | | | |
| EXP. ID | CRYSTALIZATION METHOD | SOLVENT | AMBIENT-DRIED SOLID | AMBIENT-DRIED SOLID (AAC) | VACUUM-DRIED SOLID | VACUUM-DRIED SOLID (AAC) |
| SLP8 | EQUILIBRATION AT 5° C. | ETHANOL/WATER 75.7/24.3 | C | B1 | A1 + C | A1 |
| SLP12 | EQUILIBRATION AT 25° C. | ETHANOL ABSOLUTE | A1 | B1 | A1 | A1 |
| SLP13 | EQUILIBRATION AT 25° C. | ETHANOL/WATER 98.6/1.4 | A1 + 4.5° | B1 (l.c.) | A2 | A2 |
| SLP19 | EQUILIBRATION AT 25° C. | ETHANOL/WATER 75.7/24.3 | C | B1 | A1 + C | A1 |
| SLP20 | EQUILIBRATION AT 25° C. | ETHANOL/WATER 64.6/35.4 | C | B1 | A1 + C | A1 |
| SLP22 | EQUILIBRATION AT 25° C. | WATER | C | B1 | C | A1 |

Form B2 was identified in several vacuum-dried solids recovered from the thermocycling and hydrate screen experiments. The experimental conditions where Form B2 was identified are reported in Table 12. Form B2 was physically unstable upon exposure to AAC (40° C./75% RH) for 2 days, since it converted to Form A1.

TABLE 12

| EXPERIMENTAL CONDITIONS LEADING TO THE CRYSTALLIZATION OF FORM B2 | | | | | | |
|---|---|---|---|---|---|---|
| | | | HT-XRPD | | | |
| EXP. ID | CRYSTALIZATION METHOD | SOLVENT | AMBIENT-DRIED SOLID | AMBIENT-DRIED SOLID (AAC) | VACUUM-DRIED SOLID | VACUUM-DRIED SOLID (AAC) |
| SLP9 | EQUILIBRATION AT 5° C. | ETHANOL/WATER 64.6/35.4 | C | A1 + C | B2 | A1 |
| SLP14 | EQUILIBRATION AT 25° C. | ETHANOL/WATER 96.9/3.1 | A1 | A1 | B2 | A1 |
| SLP16 | EQUILIBRATION AT 25° C. | ETHANOL/WATER 91.8/8.2 | A1 | A1 | B2 | A1 |
| SLP17 | EQUILIBRATION AT 25° C. | ETHANOL/WATER 88/12 | A1 | A1 | B2 | A1 |

TABLE 12-continued

EXPERIMENTAL CONDITIONS LEADING TO THE CRYSTALLIZATION OF FORM B2

| EXP. ID | CRYSTALIZATION METHOD | SOLVENT | HT-XRPD AMBIENT-DRIED SOLID | AMBIENT-DRIED SOLID (AAC) | VACUUM-DRIED SOLID | VACUUM-DRIED SOLID (AAC) |
|---|---|---|---|---|---|---|
| SLP18 | EQUILIBRATION AT 25° C. | ETHANOL/WATER 83/17 | A1 | A1 | B2 | A1 |
| SLP21 | EQUILIBRATION AT 25° C. | ETHANOL/WATER 38.3/61.8 | C | A1 + C | B2 | A1 |
| TCP7 | THERMOCYCLING | ETHYL ACETATE, EXTRA DRY | B2 | A1 | A1 + D | A1 |
| TCP9 | THERMOCYCLING | 1-PROPANOL, EXTRA DRY | B2 | A1 | B2 | A1 |
| TCP10 | THERMOCYCLING | THF, EXTRA DRY | B2 | A1 | B2 | A1 |

Form D was identified in the solid recovered after cycling DSC of Form A1 up to 140° C. The pattern of form D was also distinguished in the vacuum-dried solid recovered from the hydrate screen experiment (ethanol/water 98.6/1.4). Form D was physically unstable upon exposure to AAC (40° C./75% RH) for 2 days, since it converted to a mixture containing Form A1 and an unknown phase.

Form E was identified in the ambient-dried solid recovered by thermocycling in methanol. Upon drying under vacuum (5 mbar/50° C./overnight), Form E converted to Form F. The HT-XRPD are tabulated in the tables above. Both phases were physically unstable upon exposure to AAC (40° C./75% RH) for 2 days, since they converted to Form A1.

The results of the screen for the various crystal forms is summarized in Table 13.

TABLE 13

RESULTS OF THE THERMAL ANALYSIS OF THE CRYSTALLINE PHASES.

| SOLID PHASE | EXP. ID | MASS LOSS (%) | SOLVENT | API: WATER RATIO | CLASSIFICATION |
|---|---|---|---|---|---|
| A1 | SM | 8.3 | WATER | 1:3.7 | TETRAHYDRATE |
| A2 | SLP4 | 2.7 | WATER/ETHANOL | — | MIXED HYDRATE/SOLVATE |
| B1 | GEN14 | 3.3 | WATER | 1:1.5 | SESQUIHYDRATE |
| B2 | TCP9 | 3.2 | WATER | 1:1.3 | HYDRATE |
| C | SLP9 | 12.7 | WATER | 1:5.9 | HEXAHYDRATE |
| D | — | 3.9 | WATER | 1:1.6 | HYDRATE |
| E | TCP8 | 13.3 | WATER/METHANOL | — | MIXED HYDRATE/SOLVATE |
| F | TCP8 | 2.6 | WATER/METHANOL | — | MIXED HYDRATE/SOLVATE |

Example 6: Scale-Up Preparation of Form C

For the scale up of Form C, approximately 2 grams of dehydrated Form B1 were suspended in 65 mL of water overnight at RT. Afterwards, the solid was isolated by filtration and dried at ambient conditions overnight. The obtained solid showed the XRPD pattern of Form C. Form C was analyzed by HR-XRPD and the diffractogram was indexed. The unit cell belonged to the monoclinic space group $P2_1$. The unit cell parameters were a=7.924(2), b=12.155(3), c=23.257(5) Å, β=92.611(3)°, V=2237.7(10) $Å^3$, Z=2, $D_{calc}$=1.224 g/$cm^3$.

Example 7: Dynamic Vapor Sorption Measurements of Forms A1 and C

Dynamic Vapor Sorption (DVS) measurements were performed on Forms A1 and C to investigate their hygroscopic behavior. The DVS analysis consisted of a sorption-desorption-sorption cycle between 45-90-0-45% RH.

Figure 10A:
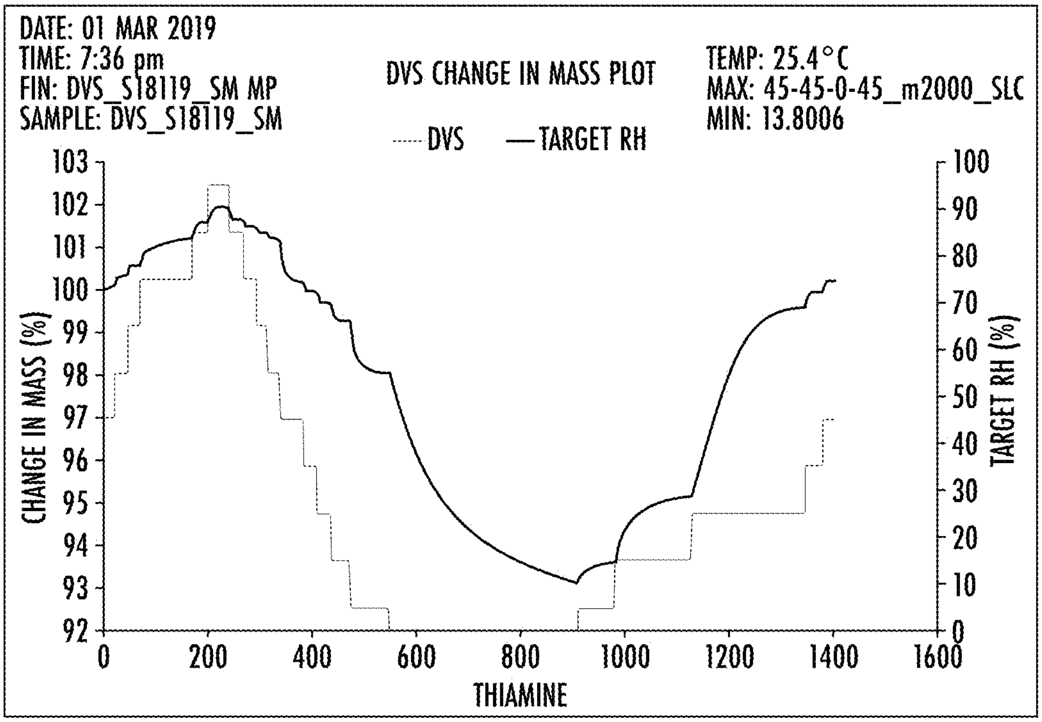
FIG. 10: Change in mass (FIG. 10A) and isotherm (FIG. 10B) resulting from dynamic vapor sorption (DVS) measurement performed on Form A1. The DVS analysis consisted of a sorption-desorption-sorption cycle between 45-90-45-0% relative humidity (RH). The diamond line represents the change in mass during the sorption cycle between 40-95% RH, the square line represents the change in mass during the desorption cycle between 95-0% RH, and the triangle line represents the change in mass during the sorption cycle between 0-45% RH.
Figure 10B:
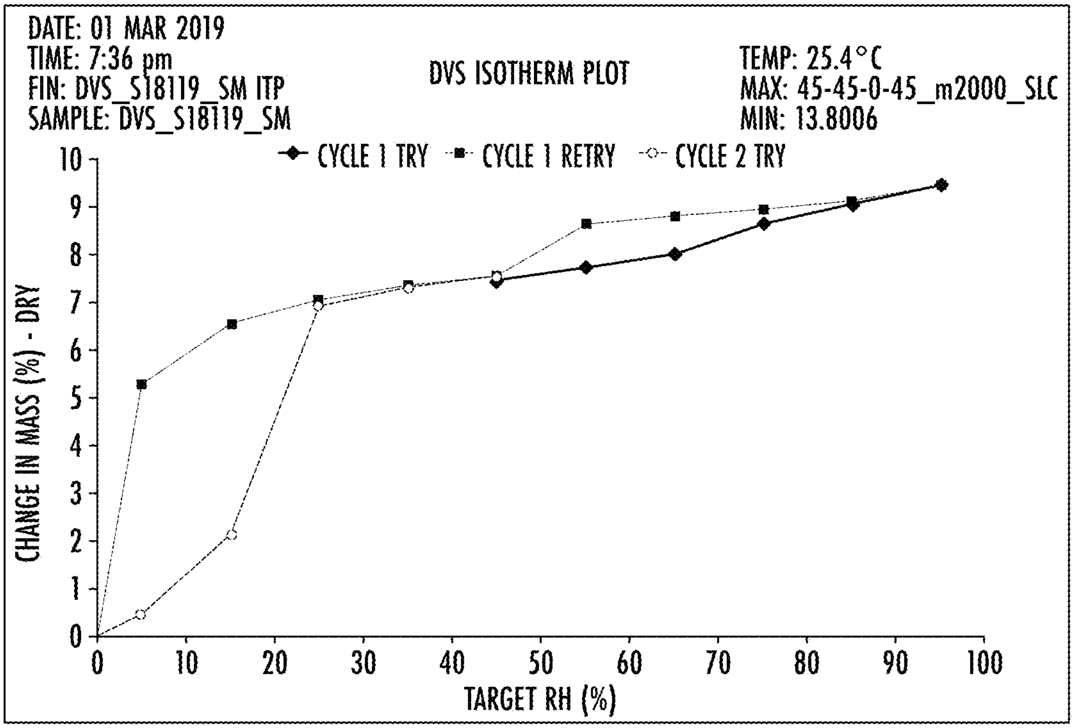

The results of the DVS measurement performed on Form A1 are shown in FIG. 10. In the first sorption cycle, the change in mass due to water vapor uptake was 2.1% between 45 and 95% RH (corresponding to approximately 0.9 water molecules per API molecule), with the steepest variation between 65 and 75% RH (diamond line, FIG. 10B).

Upon desorption (square line, FIG. 10B), the change in mass was 0.9% in the range 95-55% RH, 1% between 55 and 45% RH, 0.6% between 45 and 25% RH, 1.7% between 25 and 5% RH (corresponding to 0.7 water molecules per API molecule) and 5.3% between 5 and 0% RH (corresponding to 2.3 water molecules per API molecule).

In the last sorption cycle (triangle line, FIG. 10B), the change in mass was 7% in the range 0-25% RH (corresponding to approximately 3 water molecules per API molecule) while between 25 and 45% RH, the water vapor uptake was 0.6%.

Figure 11A:
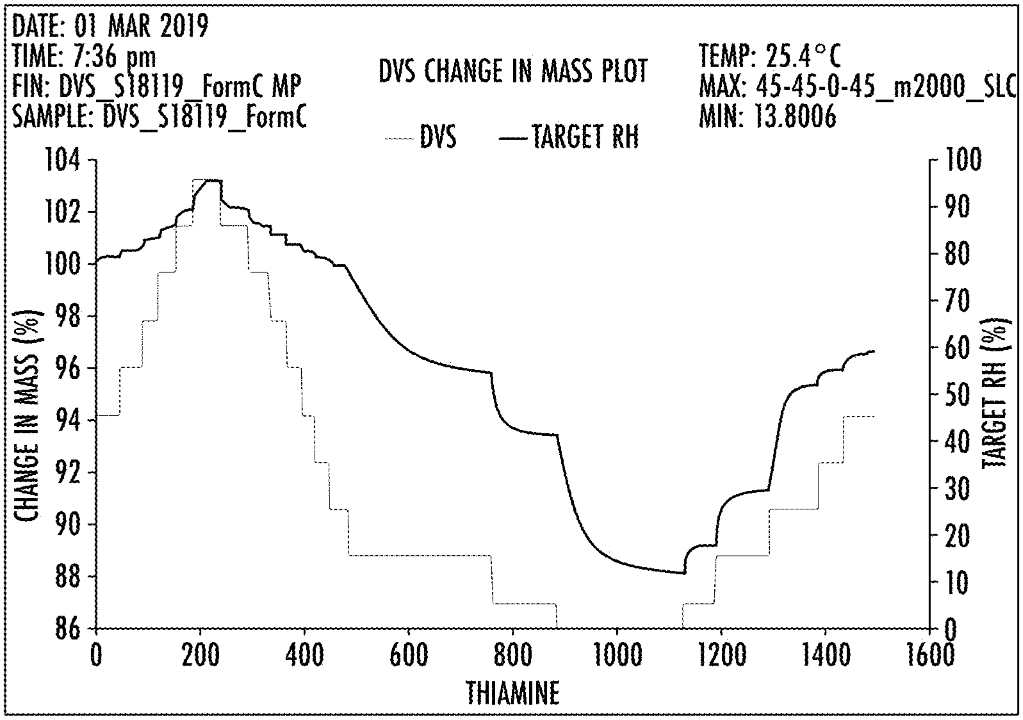
FIG. 11: Change in mass (FIG. 11A) and isotherm (FIG. 11B) resulting from DVS measurement performed on Form C. The DVS analysis consisted of a sorption-desorption-sorption cycle between 45-90-45-0% RH. The diamond line represents the change in mass during the sorption cycle between 40-95% RH, the square line represents the change in mass during the desorption cycle between 95-0% RH, and the triangle line represents the change in mass during the sorption cycle between 0-45% RH.
Figure 11B:
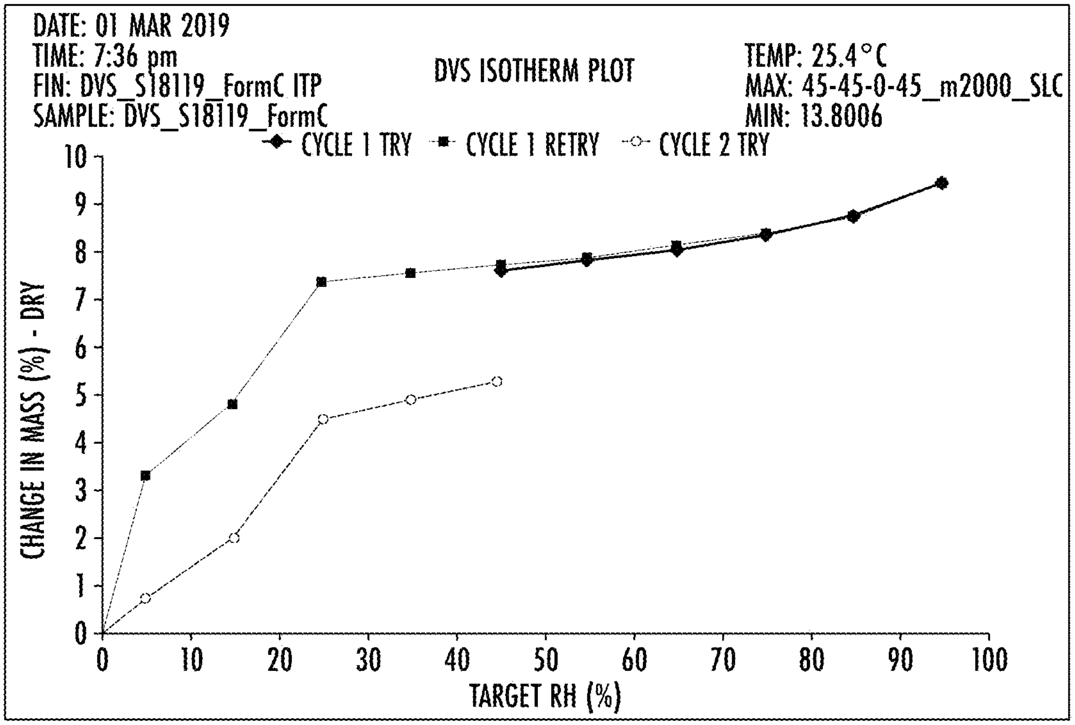

The DVS measurement of Form A1 showed that this phase was slightly hygroscopic, since it gradually absorbed approximately 1 water molecule between 40 and 95% RH level. Below 25% RH Form A1 released water, probably converting to a low-degree hydrate (or anhydrous) phase. However, the water was quickly absorbed from 0 to 25% RH, and eventually conversion to Form A1 was observed. The gradual change in mass observed between 35 to 65% RH (0.7%) suggested that Form A1 could be a non-stoichiometric hydrate, meaning that the ratio API:H2O is not exactly 1:4, but could vary depending on the environment RH level The results of the DVS measurement performed on Form C are shown in FIG. 11. In the first sorption cycle (diamond line, FIG. 11B), a gradual water uptake of 3.1% was recorded between 45 and 95% RH (corresponding to approximately 1.3 water molecules per API molecule).

Upon desorption (square line, FIG. 11B), a gradual water release was observed. From 95 to 25% RH the change in mass was 3.7% (corresponding to approximately 1.6 water molecules per API molecule) while below 25% RH a change in mass of 7.3% occurred between 25 and 5% RH (corresponding to approximately 3.2 water molecules per API molecule), whereas between 5 and 0% RH the change in mass was 6% (corresponding to approximately 2.6 water molecules per API molecule).

In the last sorption cycle (triangle line, FIG. 11B), the change in mass was 8.1% in the range 0-25% RH (corresponding to approximately 3.6 water molecules per API molecule) and 1.4% between 25 and 45% RH (corresponding to approximately 0.6 water molecules per API molecule).

From the DVS analysis performed on Form C, it turned out that this high-degree hydrate was also slightly hygroscopic, since absorption of 1.3 water molecules occurred gradually from 40 to 95% RH. However, no phase change appeared to occur between 25 to 95% RH, despite the change in mass of about 3.7%; therefore, it appeared that also Form C is a not-stoichiometric hydrate physically stable in this relative humidity range. Below 25% RH, Form C released water and probably conversion to a low-degree hydrate (or anhydrous) phase occurred. Upon sorption to 45% RH, the low-degree hydrate (or anhydrous phase) quickly absorbs water and converts to Form A1.

Form C appeared to be physically stable in the range 40→85→40% RH. When exposed to RH levels <20%, Form C released water and converted to a novel unknown phase. This crystalline phase was stable only at very low RH levels. By increasing the RH up to 20%, conversion to Form A1 was detected.

Example 8: Solubility in Biorelevant Media

The solubility of Forms A1 and C was determined in three simulated biorelevant media FaSSGF, FaSSIF and FeSSIF at 37° C. The experiments were performed in triplicate. Approximately 30 mg of API were weighed in the 8 mL glass vials and an aliquot of media was added (see Table 14 for details). The suspensions in FaSSIF and FeSSIF were equilibrated at 37° C. for 3 hours, in FaSSGF for 1 hour, since gel formation was observed for longer equilibration times. Upon completion of the equilibration time, the solids were separated from the liquid phases by centrifugation. The mother liquors were filtered using 0.2 m PTFE filters and injected at the HPLC to determine the API concentration in solution. The pH was recorded after 3 hours (1 hour for FaSSGF). The recovered ambient-dried solids were analyzed by HT-XRPD.

TABLE 14

Procedures for Preparation of Biorelevent Media

| Solution | Recipe |
|---|---|
| FaSSGF (pH 1.6) | 199.9 mg sodium chloride diluted to 100 mL with water and pH was adjusted to 1.6 with HCl. SIF powder (6.0 mg) added to the solution. |
| Blank FaSSIF (pH 6.5) | 1547.6 mg sodium chloride, 93.9 mg sodium hydroxide, 1186.7 mg sodium dihydrogen phosphate dihydrate powder diluted to 250 mL with water. pH adjusted to 6.5. |
| FaSSIF (pH 6.5) | 56.2 mg FaSSIF/FeSSIF/FaSSGF powder weighed, blank FeSSIF buffer added to 25 mL. Rested 2 hours before use. |
| Blank FeSSIF (pH 5.0) | 390.0 mg sodium hydroxide, 1183.8 sodium chloride 865 mg acetic acid and 280 mg SIF powder diluted to 100 mL with water. |
| FeSSIF (pH 5.0) | 56.1 mg FaSSIF/FeSSIF/FaSSGF powder weighed, blank FeSSIF buffer added to 5.0 mL. |

The solubility was determined by the shake-flask method where suspensions of Form A1 or Form C were prepared in the three biorelevant media at 37° C. In FaSSIF and FeSSIF the suspensions were incubated for 3 hours, whereas those in FaSSGF were equilibrated for 1 hour, since gel formation was observed for longer equilibration times.

Figure 13:
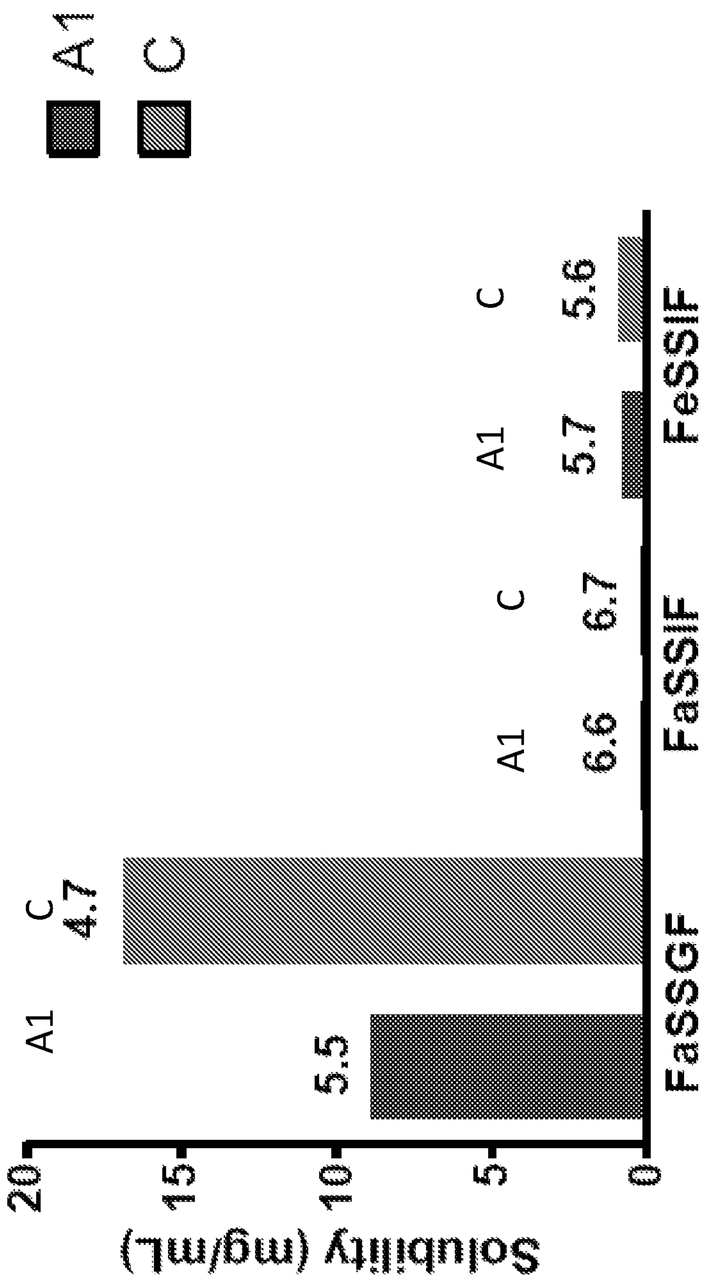
FIG. 13: Plot of solubility determine in biorelevant media for Forms A1 and C. On top of each bar the pH value measured at the end of the experiment is indicated.

The results of the solubility determination are summarized in Table 13 and FIG. 13. Forms A1 and C were practically insoluble in FaSSIF (pH 6.5). No change in pH was detected.

TABLE 15

RESULTS FOR SOLUBILITY OF FORMS A1 AND C IN BIORELEVANT MEDIA

| SOLID FORM | SIMULATED BIORELEVANT MEDIUM | INITIAL MEDIUM pH | SUSPENSION pH $t_0$ | ML pH | AMBIENT DRIED SOLID | SOLUBILITY (mg/mL) |
|---|---|---|---|---|---|---|
| A1 | FaSSIF | 6.5 | 6.5 | 6.6 | A2 | <0.1 |
| C | FaSSIF | 6.5 | 6.6 | 6.7 | C | <0.1 |
| Al | FeSSIF | 5.1 | 5.7 | 5.8 | I.c. (15.1°) | 0.8 |
| C | FaSSIF | 5.1 | 5.6 | 5.7 | I.c. (15.1°) | 0.9 |
| A1 | FaSSGF | 1.6 | 5.5 | 5.5 | I.c. (15.1°) | 8.9 |
| C | FaSSGF | 1.6 | 4.8 | 4.7 | I.c. (15.1°) | 16.9 |

Solubility close to 1 mg/mL was determined when Forms A1 and C were suspended in FeSSIF (pH 1.5). A slight increase in the pH of the medium was detected. The solids dried at ambient conditions were poorly crystalline and showed only a peak at 15.1° 2θ.

In FaSSGF (pH 1.6), higher solubility values were determined. The solubility was 9 mg/mL in the experiments started with Form A1 while Form C had a solubility around 17 mg/mL. The poorly crystalline phase with a unique diffraction peak at 15.1° 2θ was identified in the ambient-dried solids recovered from both experiments.

Forms A1 and C were practically insoluble in FaSSIF and slightly soluble (~11 mg/mL) in FeSSIF. The highest solubility values were determined in FaSSGF; in particular, for Form C were a solubility of ~17 mg/mL was determined. An actual comparison of the solubility of the two forms cannot be achieved, since both solid phases converted to a very poorly crystalline phase characterized by a unique diffraction peak at 15° 2θ. Furthermore, the solubility determined in FaSSGF was not determined at the actual pH of the medium (pH 1.6), since after 1 hour incubation the pH changed to 5.5 and 4.7, respectively.

Example 9: Intrinsic Dissolution Rate Determination in FaSSGF

The intrinsic dissolution rate of Forms A1 and C was determined in FaSSGF. For preparation of the tablets, 10 mg of Form A1 and Form C were pressed in the cylindrical hole of a passivated stainless-steel die, to a uniform, flat surface, with an exposed area of 0.071 $cm^2$. The pressure applied was approximately 40 bar for 2 minutes. The two tablets were placed in 30 mL vials and afterwards the FaSSGF solution pre-warmed at 37° C. (pH 1.6) was added.

After FaSSGF addition, stirring was started. The medium (20 mL) was added to vessels containing tablets of Forms A1 and C. The tablets were kept at 37° C. under continuous stirring. Aliquots of liquid phases (50 μL) were taken from each vial after 3, 10, 20, 30, 45 and 60 minutes and measured by HPLC with ELSD detector.

Figure 14:
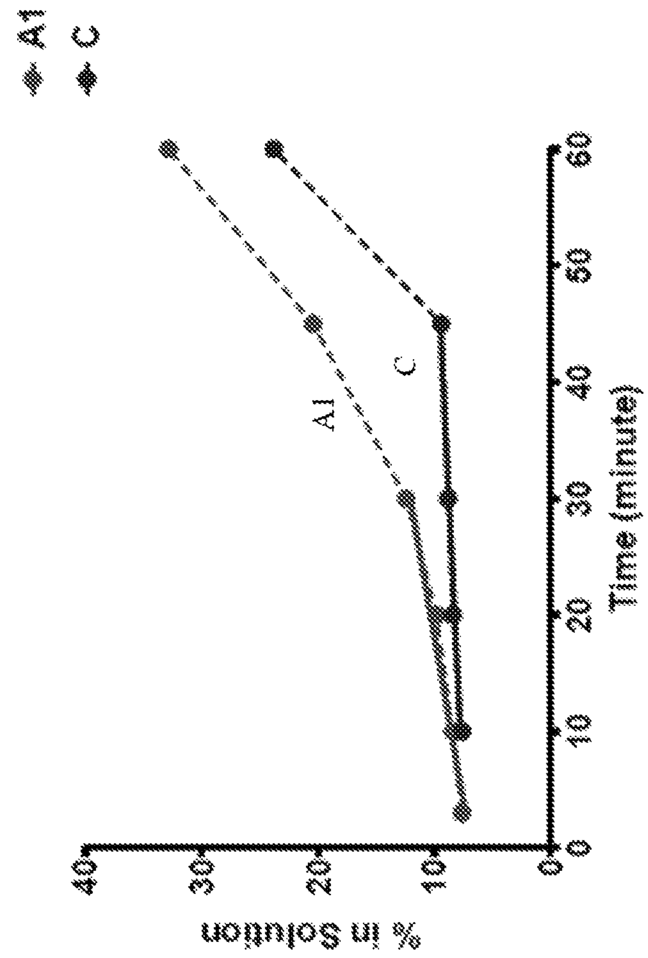
FIG. 14: Plot of API concentration in solution (%) against the time. Small aliquots (50 μL) of solutions were taken after 3, 10, 20, 30, 45 and 60 minutes and analyzed by HPLC.

In the plot shown in FIG. 14, the % concentration of the API in solution is plotted against the time. The dissolution rate (Table 16) was calculated in the interval between 3 and 30 minutes for the experiment started with Form A1, and in the range 10-45 minutes for the experiment started with Form C.

TABLE 16

Dissolution Rates

| Solid phase | IDR ($mg/min/cm^2$) |
|---|---|
| A1 | 0.049 |
| C | 0.014 |

Based on the dissolution profiles recorded, it appeared that within the first 30 minutes Form A1 had a slightly faster dissolution rate than Form C. After 45 minutes, the API concentration in solution was almost 20% for the experiment started with Form A1, whereas with Form C, the API concentration in solution was still below 10%. After 60 minutes, the API concentration in solution was above 30% for Form A1, whereas with Form C the API concentration in solution was slightly above 20%.

Example 10: Physical Stability

Solid samples of Forms A1, B1 and C were incubated at three different conditions to test their physical stability: 80° C., closed vial, 24 hours; 60° C./29% RH, open vial, 48 hours; and 40° C./75% RH, open vial, 48 hours. The solids recovered after the stability studies were analyzed by HR-XRPD, TGMS and DSC. The results of the analytical characterization are reported in Table 17.

TABLE 17

Physical Stability of Polymorphs

| Solid Form | Tested conditions | Solid Phase Composition | Mass loss (%) | Endo/water Loss (° C.) | Endo/ Decomp. (° C.) |
|---|---|---|---|---|---|
| A1 | 80° C., closed vial, 24 h | A1 | 9.1 | 68-106 | 282-310 |
| A1 | 60° C./29% RH, open vial, 48 h | A1 | 8.5 | 68-104 | 282-304 |
| A1 | 40° C./75% RH, open vial, 48 h | A1 | 9.2 | 60-106 | 283-314 |
| B1 | 80° C., closed vial, 24 h | B1 | 1.8 | 90-120 | 282-315 |
| B1 | 60° C./29% RH, open vial, 48 h | A1 | 9.0 | 67-105 | 284-306 |
| B1 | 40° C./75% RH, open vial, 48 h | A1 | 8.9 | 64-107 | 281-315 |
| C | 80° C., closed vial, 24 h | A1 | 8.8 | 70-99 | 281-304 |
| C | 60° C./29% RH, open vial, 48 h | A1 | 8.7 | 65-97 | 280-316 |
| C | 40° C./75% RH, open vial, 48 h | C | 12.6 | 40-110 | 280-312 |

Form A1 was physically stable in all the tested conditions. Form B1 was physically stable only in closed vial at 80° C., whereas it converted to Form A1 upon exposure to 60° C./29% RH and 40° C./75% RH. Form C converted to Form A1 both at 80° C. in closed vial within 24 hours and when exposed at 60° C./29% RH for 2 days. Form C was physically stable upon exposure to 40° C./75% RH for 2 days. The results of the physical stability test indicate that while Form A1 is physically stable under a broad range of temperature and RH conditions, Forms B1 and C are more sensitive to the storage conditions. The dehydrated Form B1 absorbs water already at 29% RH converting to A1, and the hexahydrate Form C releases water at low RH levels or at elevated temperatures, converting to Form A1.

While certain embodiments have been illustrated and described, it should be understood that changes and modifications can be made therein in accordance with ordinary skill in the art without departing from the technology in its broader aspects as defined in the following claims.

The embodiments illustratively described herein may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

REFERENCES (a) Braak et al., "Idiopathic Parkinson's disease: possible routes by which vulnerable neuronal types may be subject to neuroinvasion by an unknown pathogen," *J. Neural. Transm.* (*Vienna*), 110:517-36 (2003).

(b) Braak et al., "Staging of brain pathology related to sporadic Parkinson's disease," *Neurobiol. Aging,* 24:197-211 (2003).

McKhann, et al., "The diagnosis of dementia due to Alzheimer's disease: recommendations from the National Institute on Aging-Alzheimer's Association workgroups on diagnostic guidelines for Alzheimer's disease," *Alzheimer's Dement.,* 2011 May; 7(3):263-9.

Zasloff, et al., "A spermine-coupled cholesterol metabolite from the shark with potent appetite suppressant and antidiabetic properties," *Int J Obes Relat Metab Disord.,* 2001 May; 25(5):689-97.

Zhao et al., "A comparative study of the amount of α-synuclein in ischemic stroke and Parkinson's disease," *Neurol. Sci.,* 37(5):749-54 (2016).

The invention claimed is:

1. A crystalline phosphate hydrate of Compound I:

Compound I

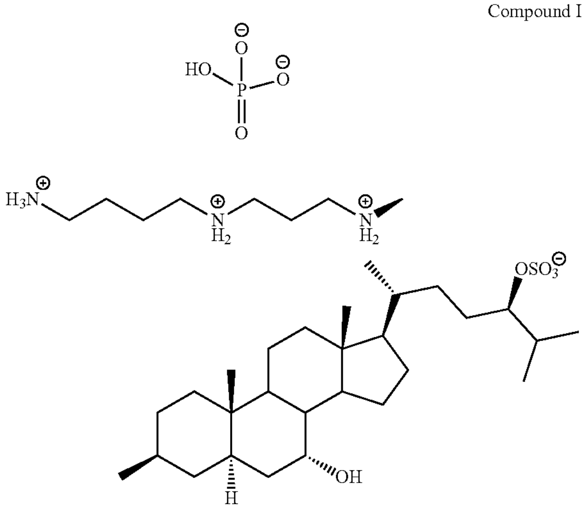

wherein the crystalline phosphate hydrate comprises Form A1 and/or Form C, wherein:

a) Form A1 is characterized by an X-ray powder diffraction (XRPD) pattern having peaks (Cu $K_{\alpha 1}$ radiation) at 3.96°, 8.59°, 10.84°, 11.49°, 13.27°, 13.89°, 15.27°, 15.52°, 15.78°, 15.98°, 17.72°, 17.91°, 18.76°, 19.18°, 19.37°, 20.44°, 20.58°, 20.80°, 21.24°, 21.76°, 22.18°, 23.09°, 23.35°, 23.83°, 24.02°, 24.53°, 25.10°, 25.48°, 25.81°, 26.14°, and 26.67° (each ±0.01°2θ); and b) Form C is characterized by an X-ray powder diffraction (XRPD) pattern having peaks (Cu $K_{\alpha 1}$ radiation) at 3.82°, 8.22°, 10.55°, 11.19°, 11.45°, 11.99°, 13.35°, 13.77°, 14.05°, 14.59°, 15.14°, 15.63°, 16.39°, 16.89°, 17.28°, 17.94°, 18.57°, 18.92°, 19.39°, 19.75°, 20.71°, 21.16°, 21.45°, 21.99°, 22.49°, 22.98°, 23.26°, 23.79°, 24.11°, 24.59°, and 24.91° (each ±0.01°2θ).

2. The crystalline phosphate hydrate of claim 1:

wherein the crystalline phosphate hydrate comprises Form A1; and wherein:

(a) the crystalline phosphate hydrate is a tetrahydrate; and/or (b) has a differential scanning calorimetry thermogram comprising an endotherm at about 40° C. to about 120° C.

3. The crystalline phosphate hydrate of claim 1:

wherein the crystalline phosphate hydrate comprises Form C; and wherein:

(a) the crystalline phosphate hydrate is a hexahydrate; and/or (b) has a differential scanning calorimetry thermogram comprising an endotherm at about 40° C. to about 120° C.

4. A composition comprising the crystalline phosphate hydrate of claim 1.

5. The composition of claim 4, comprising one or more of the following:

(a) an aqueous carrier;

(b) a buffer;

(c) a sugar; and/or (d) a polyol compound.

6. The composition of claim 4, wherein the composition further comprises at least one additional active agent.

7. The composition of claim 4, wherein the composition is formulated:

(a) for administration selected from the group consisting of oral, pulmonary, rectal, colonic, parenteral, intracisternal, intravaginal, intraperitoneal, intravenous, subcutaneous, intramuscular, nebulization, inhalation, ocular, otic, local, buccal, nasal, and topical administration;

(b) into a dosage form selected from the group consisting of liquid dispersions, gels, aerosols, ointments, creams, lyophilized formulations, tablets, and capsules;

(c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

8. The composition of claim 4, formulated:

(a) for oral administration; and/or (b) as an oral tablet or capsule; and/or (c) for intranasal administration.

9. A method of preparing the crystalline phosphate hydrate of claim 1, comprising contacting Compound II:

(b) the ratio of water to ethanol is about 1 to about 1; and/or (c) the water and ethanol further comprise sodium hydroxide (NaOH).

13. A method of treating a subject in need having a condition susceptible to treatment with an aminosterol, comprising administering a therapeutically effective amount of the composition according to claim 4, and optionally wherein the condition is correlated with abnormal alpha-synuclein pathology and/or dopaminergic dysfunction.

14. A method of treating, preventing, and/or slowing the onset or progression of a condition or disorder, or a related symptom, correlated with abnormal alpha-synuclein pathology and/or dopaminergic dysfunction, in a subject in need, comprising administering a therapeutically effective amount of a composition according to claim 4.

15. The method of claim 14, wherein:

(a) the symptom is selected from the group consisting of constipation, hallucinations, cognitive impairment, and inflammation;

(b) the symptom is correlated with a synucleopathy, a neurodegenerative disease, a neurological disease or disorder, a psychological and/or behavior disorder, or a cerebral or general ischemic disorder or condition; or (c) the condition or disorder is a synucleopathy, neurodegenerative disease, or neurological disease or disorder;

(d) the condition or disorder is a psychological and/or behavior disorder; or

Compound II

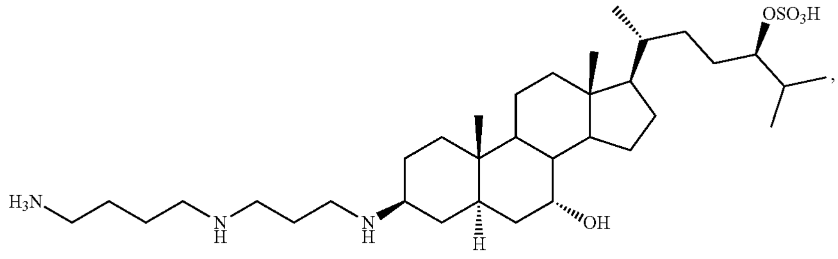

, or a pharmaceutically acceptable salt thereof, with phosphoric acid to form the crystalline phosphate hydrate.

10. The method of claim 9, wherein the pharmaceutically acceptable of Compound II is a lactate salt of Compound II.

11. The method of claim 10, wherein the lactate salt of Compound II has the formula:

(e) the condition or disorder is a cerebral or general ischemic disorder or condition.

16. The method of claim 15, wherein:

(a) the synucleopathy, neurodegenerative disease, or neurological disease or disorder is selected from the group consisting of Parkinson's disease, Alzheimer's disease,

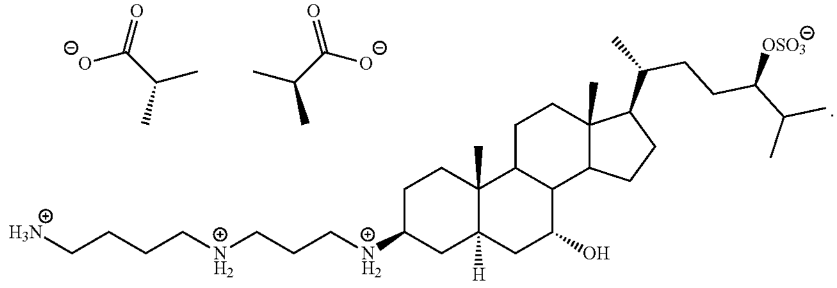

.

12. The method of claim 9, wherein:

(a) Compound II, or a pharmaceutically acceptable salt thereof, is in water and ethanol prior to contacting with phosphoric acid; and/or schizophrenia, multiple system atrophy, Lewy body dementia, dementia with Lewy bodies, Huntington's Disease, Multiple Sclerosis, Amyotorphic Lateral Sclerosis, Friedreich's ataxia, vascular dementia, spinal muscular atrophy, supranuclear palsy, progressive nuclear palsy, frontotemporal dementia, progressive nuclear palsy, Guadeloupian Parkinsonism, spinocerebellar ataxia, parkinsonism, traumatic brain injury, degenerative processes associated with aging, and dementia of aging;

(b) the psychological or behavior disorder is selected from the group consisting of depression, autism, autism spectrum disorder, Down syndrome, Gaucher's disease, Krabbe's disease, lysosomal conditions affecting glycosphingolipid metabolism, ADHD, agitation, anxiety, delirium, irritability, illusion and delusions, amnesia, apathy, bipolar disorder, disinhibition, aberrant motor and obsessive-compulsive behaviors, addiction, cerebral palsy, epilepsy, major depressive disorder, and sleep disorders such as REM sleep behavior disorder (RBD), sleep fragmentation, REM behavior disorder, circadian rhythm dysfunction, sleep apnea, and cognitive impairment; or (c) the cerebral or general ischemic disorder or condition is selected from the group consisting of microangiopathy, intrapartum, cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects, high blood pressure, low blood pressure, and pulmonary edema.

17. A method of treating, preventing, and/or slowing the onset or progression of a cerebral or general ischemic disorder and/or a related symptom, correlated with abnormal alpha-synuclein pathology and/or dopaminergic dysfunction, in a subject in need, comprising administering a therapeutically effective amount of a composition according to claim 4.

18. The method of claim 17, wherein the cerebral or general ischemic disorder and/or a related symptom is selected from the group consisting of microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, low blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, cardiac conduction defects (CCDs) and/or a related symptom, and pulmonary edema.

19. A method of inhibiting protein tyrosine phosphatase 1B (PTP1B) in a subject, the method comprising administering to the subject a therapeutically effective amount of a composition according to claim 4.

20. The method of claim 13, wherein:

(a) the method of administration comprises oral, nasal, sublingual, buccal, rectal, vaginal, intravenous, intra-arterial, intradermal, intraperitoneal, intrathecal, intramuscular, epidural, intracerebral, intracerebroventricular, transdermal, or any combination thereof, and/or (b) the method of administration is nasal administration, oral administration, or a combination thereof.

21. The method of claim 13, wherein:

(a) the therapeutically effective amount of the composition comprises:
  (i) about 0.1 to about 20 mg/kg body weight of the subject;
  (ii) about 0.1 to about 15 mg/kg body weight of the subject;
  (iii) about 0.1 to about 10 mg/kg body weight of the subject;
  (iv) about 0.1 to about 5 mg/kg body weight of the subject; or
  (v) about 0.1 to about 2.5 mg/kg body weight of the subject; and/or (b) the therapeutically effective amount of the composition comprises:
  (i) about 0.001 to about 500 mg/day;
  (ii) about 0.001 to about 250 mg/day;
  (iii) about 0.001 to about 125 mg/day;
  (iv) about 0.001 to about 50 mg/day;
  (v) about 0.001 to about 25 mg/day;
  (vi) about 0.001 to about 10 mg/day;
  (vii) about 0.001 to about 6 mg/day;
  (viii) about 0.001 to about 4 mg/day; or
  (ix) about 0.001 to about 2 mg/day; and/or (c) the method of administration comprises oral administration and wherein the therapeutically effective amount of the composition comprises:
  (i) about 1 to about 300 mg/day; or
  (ii) about 25 to about 500 mg/day.

22. The method of claim 13, wherein:

(a) the composition is administered in combination with at least one additional active agent to achieve either an additive or synergistic effect; and/or (b) the composition is administered in combination with at least one additional active agent to achieve either an additive or synergistic effect and wherein the additional active agent is administered via a method selected from the group consisting of:
  (i) concomitantly;
  (ii) as an admixture;
  (iii) separately and simultaneously or concurrently; and
  (iv) separately and sequentially; and/or (c) the composition is administered in combination with at least one additional active agent to achieve either an additive or synergistic effect, and wherein the additional active agent is a second aminosterol having a different structure from Compound I.

23. The method of claim 13, wherein:

(a) administration of the composition comprises administration on an empty stomach, optionally within two hours of the subject waking; and/or (b) no food is consumed by the subject after about 60 to about 90 minutes from administration of the composition.

24. The method of claim 13, wherein the composition comprises a pharmaceutically acceptable grade of the crystalline phosphate hydrate of Compound I.

25. The method of claim 13, wherein the subject is a mammal, and optionally wherein the subject is a human.

26. The method of claim 13, further comprising:
(a) determining a dosage of the composition for the subject, wherein the composition dosage is determined based on the effectiveness of the composition dosage in improving or resolving a symptom being evaluated,
(b) followed by administering the composition dosage to the subject for a period of time, wherein the method comprises:
(i) identifying a symptom to be evaluated, wherein the symptom is susceptible to treatment with an aminosterol;
(ii) identifying a starting dosage of composition for the subject; and
(iii) administering an escalating composition dosage to the subject over a period of time until an effective dosage for the symptom being evaluated is identified, wherein the effective dosage is composition dosage where improvement or resolution of the symptom is observed, and fixing the composition dosage at that level for that particular symptom in that particular subject, and
optionally wherein improvement or resolution of the symptom is measured using a clinically recognized scale or tool.

27. The method of claim 26, wherein:
(a) the composition is administered orally and:
(i) the starting composition dosage ranges from about 10 mg up to about 150 mg/day;
(ii) the dosage of the composition for the subject following escalation is fixed at a range of from about 25 mg up to about 500 mg/day; and/or
(iii) the dosage of composition is escalated in about 25 mg increments; or
(b) the composition is administered intranasally and:
(i) the starting composition dosage ranges from about 0.001 mg to about 3 mg/day;
(ii) the dosage of the composition for the subject following escalation is fixed at a range of from about 0.001 mg up to about 6 mg/day;
(iii) the dosage of the composition for the subject following escalation is a dosage which is subtherapeutic when given orally or by injection; and/or
(iv) the dosage of the composition is escalated in increments of about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

28. The method of claim 26, wherein:
(a) the dosage of the composition is escalated every about 3 to about 5 days; and/or
(b) the starting composition dosage is higher if the symptom being evaluated is severe; and/or
(c) the symptom is correlated with abnormal alpha-synuclein pathology and/or dopaminergic dysfunction; and/or
(d) the symptom to be evaluated is selected from the group consisting of:
(i) at least one non-motor aspect of experiences of daily living as defined by Part I of the Unified Parkinson's Disease Rating Scale selected from the group consisting of cognitive impairment, hallucinations and psychosis, depressed mood, anxious mood, apathy, features of dopamine dysregulation syndrome, sleep problems, daytime sleepiness, pain, urinary problems, constipation problems, lightheadedness on standing, and fatigue;
(ii) at least one motor aspect of experiences of daily living as defined by Part II of the Unified Parkinson's Disease Rating Scale selected from the group consisting of speech, saliva and drooling, chewing and swallowing, eating tasks, dressing, hygiene, handwriting, turning in bed, tremors, getting out of a bed, a car, or a deep chair, walking and balance, and freezing;
(iii) at least one motor symptom identified in Part III of the Unified Parkinson's Disease Rating Scale selected from the group consisting of speech, facial expression, rigidity, finger tapping, hand movements, pronation-supination movements of hands, toe tapping, leg agility, arising from chair, gait, freezing of gait, postural stability, posture, body bradykinesia, postural tremor of the hands, kinetic tremor of the hands, rest tremor amplitude, and constancy of rest tremor;
(iv) at least one motor complication identified in Part IV of the Unified Parkinson's Disease Rating Scale selected from the group consisting of time spent with dyskinesias, functional impact of dyskinesias, time spent in the off state, functional impact of fluctuations, complexity of motor fluctuations, and painful off-state dystonia;
(v) constipation;
(vi) depression;
(vii) cognitive impairment;
(viii) sleep problems or sleep disturbances;
(ix) circadian rhythm dysfunction;
(x) hallucinations;
(xi) fatigue;
(xii) REM disturbed sleep;
(xiii) REM behavior disorder;
(xiv) erectile dysfunction;
(xv) apnea;
(xvi) postural hypotension;
(xvii) correction of blood pressure or orthostatic hypotension;
(xviii) nocturnal hypertension;
(xix) regulation of temperature;
(xx) improvement in breathing or apnea;
(xxi) correction of cardiac conduction defect;
(xxii) amelioration of pain;
(xxiii) restoration of bladder sensation and urination;
(xxiv) urinary incontinence; and/or
(xxv) control of nocturia.

29. The method of claim 28, wherein the symptom to be evaluated is constipation, and wherein:
(a) the fixed escalated composition dosage for constipation is defined as the composition dosage that results in a complete spontaneous bowel movement (CSBM) within 24 hours of dosing on at least 2 of 3 days at a given dosage;
(b) if average complete spontaneous bowel movement (CSBM) or average spontaneous bowel movement (SBM) is greater than or equal to 1 per week, then the starting composition dosage prior to escalation is 75 mg/day; and/or
(c) if average CSBM or SBM is less than 1 per week, then the starting composition dosage prior to escalation is 150 mg/day.

30. A method of increasing gene transcription in the gut of a subject, comprising administering to the subject a therapeutically effective amount of a crystalline phosphate hydrate according to claim 1.

31. The method of claim 30, wherein:

(a) the increase in gene transcription is for one or more genes selected from the group consisting of caspase 14, collagen type XVII alpha 1, corneodesmosin, cornifelin, cystatin E/M, dermokine, desmocollin 1, desmoglein 1 beta, filaggrin, gap junction protein beta 4, gap junction protein beta 6, H19 imprinted maternally expressed transcript, hornerin, kallikrein related-peptidase 7 chymotryptic stratum, keratin 1, keratin 10, keratinocyte differentiation associated protein, keratinocyte expressed proline-rich, late cornified envelope 1A1, late cornified envelope 1A2, late cornified envelope 1B, late cornified envelope 1C, late cornified envelope 1E, late cornified envelope 1F, late cornified envelope 1G, late cornified envelope 1H, late cornified envelope 1I, late cornified envelope 1J, late cornified envelope 1L, late cornified envelope 1M, late cornified envelope 3C, late cornified envelope 3E, late cornified envelope 3F, lectin galactose binding soluble 7, loricrin, sciellin, myoglobin, myosin binding protein C slow-type, myosin heavy polypeptide 1 skeletal muscle, myosin heavy polypeptide 8 skeletal muscle, myosin light chain phosphorylatable fast ske, myosin light polypeptide 3, myozenin 1, myozenin 2, and titin-cap; and/or (b) the increase in gene transcription is selected from about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, about 250% to about 300%, about 300% to about 350%, about 350% to about 400%, about 400% to about 450%, about 500% to about 600%, about 600% to about 700%, about 700% to about 800%, about 800% to about 900%, about 900% to about 1000%, or about 1000% to about 1500%.

* * * * *